US009650657B2

(12) United States Patent
Chundawat et al.

(10) Patent No.: US 9,650,657 B2
(45) Date of Patent: May 16, 2017

(54) METHODS FOR PRODUCING EXTRACTED AND DIGESTED PRODUCTS FROM PRETREATED LIGNOCELLULOSIC BIOMASS

(75) Inventors: Shishir Chundawat, Madison, WI (US); Leonardo Da Costa Sousa, Lansing, MI (US); Albert M. Cheh, Bethesda, MD (US); Venkatesh Balan, East Lansing, MI (US); Bruce Dale, Mason, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 13/642,052

(22) PCT Filed: Apr. 19, 2011

(86) PCT No.: PCT/US2011/033079
§ 371 (c)(1),
(2), (4) Date: Dec. 17, 2012

(87) PCT Pub. No.: WO2011/133571
PCT Pub. Date: Oct. 27, 2011

(65) Prior Publication Data
US 2013/0217073 A1  Aug. 22, 2013

Related U.S. Application Data

(60) Provisional application No. 61/325,560, filed on Apr. 19, 2010.

(51) Int. Cl.
| | | |
|---|---|---|
| C12P 19/14 | (2006.01) | |
| C13K 1/02 | (2006.01) | |
| C08H 7/00 | (2011.01) | |
| C08B 15/02 | (2006.01) | |
| C08B 37/00 | (2006.01) | |
| C12P 19/20 | (2006.01) | |
| C12P 7/10 | (2006.01) | |
| C08H 8/00 | (2010.01) | |

(52) U.S. Cl.
CPC ............. *C12P 19/14* (2013.01); *C08B 15/02* (2013.01); *C08B 37/0003* (2013.01); *C08B 37/0057* (2013.01); *C08H 6/00* (2013.01); *C08H 8/00* (2013.01); *C12P 7/10* (2013.01); *C12P 19/20* (2013.01); *C13K 1/02* (2013.01); *C12P 2201/00* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 2,017,779 A | 10/1935 | Vosburgh | |
| 2,220,624 A | 11/1940 | Sherrard et al. | |
| 2,548,192 A | 4/1951 | Berg | |
| 3,259,501 A | 7/1966 | Ulrey | |
| 3,306,006 A | 2/1967 | Urban | |
| 3,707,436 A | 12/1972 | O'Connor | |
| 3,920,419 A | 11/1975 | Schroeder et al. | |
| 3,951,734 A * | 4/1976 | DeHaas et al. | 162/72 |
| 4,064,276 A | 12/1977 | Conradsen et al. | |
| 4,153,435 A | 5/1979 | Fischer | |
| 4,263,744 A | 4/1981 | Stoller | |
| 4,287,162 A | 9/1981 | Scheibel | |
| 4,356,196 A | 10/1982 | Hultquist | |
| 4,370,351 A | 1/1983 | Harper | |
| 4,461,648 A | 7/1984 | Foody | |
| 4,526,791 A | 7/1985 | Young | |
| 4,581,044 A | 4/1986 | Uno et al. | |
| 4,589,334 A | 5/1986 | Andersen | |
| 4,594,131 A | 6/1986 | Maier | |
| 4,600,590 A | 7/1986 | Dale | |
| 4,624,805 A | 11/1986 | Lawhon | |
| 4,644,060 A | 2/1987 | Chou | |
| 4,848,026 A | 7/1989 | Dunn-Coleman et al. | |
| 4,871,370 A | 10/1989 | Yatsu et al. | |
| 4,986,835 A | 1/1991 | Uno et al. | |
| 4,995,888 A | 2/1991 | Beaupre et al. | |
| 5,025,635 A | 6/1991 | Rockenfeller et al. | |
| 5,037,663 A | 8/1991 | Dale | |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Gibson LJ (2012). The hierarchical structure and mechanics of plant materials. The Journal of the Royal Society Interface, v9, p. 2749-2766.*
Wahlco Inc (2006). "Ammonia Systems for SCR Applications" Internet article, 3 pages.*
Karrsson et al. (2002). Enzymatic properties of the low molecular mass endoglucanases Cel12A (EG III) and Cel45A (EG V) of Trichoderma reesei. Journal of Biotechnology, v99, p. 63-78.*
Qin et al. (2008). Purification and characterization of recombinant endoglucanase of Trichoderma reesei expressed in *Saccharomyces cerevisiae* with higher glycosylation and stability. Protein Expression and Purification, v58, p. 162-167.*
Iyer et al. (1996). Ammonia Recycled Percolation Process for Pretreatment of Herbaceous Biomass. Applied Biochemistry and Biotechnology, v57/58, p. 121-132.*
Kim et al. (Aug. 2009, Ch. 6 and p. 79-91 in "Biofuels, Methods and Protocols." Methods in Molecular Biology, v581, ISSN: 1064-3745.*
Sousa et al. (2016). Next-generation ammonia pretreatment enhances cellulosic biofuel production. Energy Environ. Sci., v9, p. 1215-1223.*

(Continued)

*Primary Examiner* — Scott Long
*Assistant Examiner* — Sean C Barron
(74) *Attorney, Agent, or Firm* — Clark IP Law, PLC

(57) ABSTRACT

Methods for producing extracted and digested products from pretreated lignocellulosic biomass are provided. The methods include converting native cellulose $I_\beta$ to cellulose $III_I$ by pretreating the lignocellulosic biomass with liquid ammonia under certain conditions, and performing extracting or digesting steps on the pretreated/converted lignocellulosic biomass.

28 Claims, 21 Drawing Sheets

(56) References Cited

U.S. PATENT DOCUMENTS

| | | |
|---|---|---|
| 5,047,332 A | 9/1991 | Chahal |
| 5,114,694 A | 5/1992 | Grotz, Jr. |
| 5,171,592 A | 12/1992 | Holtzapple et al. |
| 5,370,999 A | 12/1994 | Stuart |
| 5,473,061 A | 12/1995 | Bredereck et al. |
| 5,660,603 A | 8/1997 | Elliot et al. |
| 5,736,032 A | 4/1998 | Cox et al. |
| 5,865,898 A | 2/1999 | Holtzapple et al. |
| 5,939,544 A | 8/1999 | Karstens et al. |
| 6,027,552 A | 2/2000 | Ruck et al. |
| 6,106,888 A | 8/2000 | Dale et al. |
| 6,176,176 B1 | 1/2001 | Dale et al. |
| 6,255,505 B1 | 7/2001 | Bijl et al. |
| 6,416,621 B1 | 7/2002 | Karstens |
| 6,425,939 B1 | 7/2002 | Moreau et al. |
| 6,444,437 B1 | 9/2002 | Sporleder et al. |
| 6,524,848 B2 | 2/2003 | McNelly |
| 6,585,807 B2 | 7/2003 | Umino et al. |
| 6,620,292 B2 | 9/2003 | Wingerson |
| 6,872,296 B2 | 3/2005 | Kim |
| 6,893,484 B2 | 5/2005 | Thomas |
| 7,049,485 B2 | 5/2006 | Sticklen et al. |
| 7,187,176 B2 | 3/2007 | Lim et al. |
| 7,250,074 B2 | 7/2007 | Tonkovich et al. |
| 7,371,926 B2 | 5/2008 | Sticklen et al. |
| 7,371,962 B2 | 5/2008 | Zuppero et al. |
| 7,494,675 B2 | 2/2009 | Abbas et al. |
| 7,494,792 B2 | 2/2009 | Warzywoda et al. |
| 7,537,744 B2 | 5/2009 | Benderly et al. |
| 7,585,652 B2 | 9/2009 | Foody et al. |
| 7,771,565 B2 | 8/2010 | Kirov et al. |
| 7,910,338 B2 | 3/2011 | Hennessey et al. |
| 7,910,675 B2 | 3/2011 | Funk et al. |
| 7,915,017 B2 | 3/2011 | Dale |
| 7,937,851 B2 | 5/2011 | Rajagopalan et al. |
| 8,020,342 B2 | 9/2011 | Karpik |
| 8,030,030 B2 | 10/2011 | Varanasi et al. |
| 8,367,378 B2 | 2/2013 | Balan et al. |
| 8,394,177 B2 | 3/2013 | Campbell et al. |
| 8,394,611 B2 | 3/2013 | Dale et al. |
| 8,419,900 B2 | 4/2013 | Baba et al. |
| 8,444,925 B2 | 5/2013 | Baba |
| 8,551,549 B2 | 10/2013 | Zeeck |
| 8,651,403 B2 | 2/2014 | Camp et al. |
| 8,673,031 B2 | 3/2014 | Dale et al. |
| 8,771,425 B2 | 7/2014 | Dale |
| 8,846,123 B2 | 9/2014 | Zeeck |
| 8,945,245 B2 | 2/2015 | Bals et al. |
| 8,968,515 B2 | 3/2015 | Balan et al. |
| 2003/0044951 A1 | 3/2003 | Sporleder et al. |
| 2005/0064577 A1 | 3/2005 | Berzin |
| 2005/0233423 A1 | 10/2005 | Berka et al. |
| 2006/0014260 A1 | 1/2006 | Fan et al. |
| 2006/0130396 A1 | 6/2006 | Werner |
| 2006/0177917 A1 | 8/2006 | Warzywoda et al. |
| 2007/0029252 A1 | 2/2007 | Dunson, Jr. et al. |
| 2007/0031918 A1 | 2/2007 | Dunson et al. |
| 2007/0037259 A1 | 2/2007 | Hennessey et al. |
| 2007/0113736 A1 | 5/2007 | Bandosz |
| 2007/0192900 A1 | 8/2007 | Sticklen |
| 2007/0202214 A1 | 8/2007 | Lewis et al. |
| 2007/0227063 A1 | 10/2007 | Dale et al. |
| 2007/0287795 A1 | 12/2007 | Huda et al. |
| 2008/0008783 A1 | 1/2008 | Dale |
| 2008/0057555 A1 | 3/2008 | Nguyen |
| 2008/0087165 A1 | 4/2008 | Wright et al. |
| 2008/0115415 A1 | 5/2008 | Agrawal et al. |
| 2008/0171297 A1 | 7/2008 | Reynolds et al. |
| 2008/0229657 A1 | 9/2008 | Senyk et al. |
| 2008/0256851 A1 | 10/2008 | Lumb |
| 2008/0264254 A1 | 10/2008 | Song et al. |
| 2008/0280236 A1 | 11/2008 | Wright |
| 2009/0011474 A1 | 1/2009 | Balan et al. |
| 2009/0042259 A1 | 2/2009 | Dale et al. |
| 2009/0049748 A1 | 2/2009 | Day et al. |
| 2009/0053770 A1 | 2/2009 | Hennessey et al. |
| 2009/0053771 A1 | 2/2009 | Dale et al. |
| 2009/0061486 A1 | 3/2009 | Edwards et al. |
| 2009/0087898 A1 | 4/2009 | Haase et al. |
| 2009/0093027 A1 | 4/2009 | Balan et al. |
| 2009/0099079 A1 | 4/2009 | Emalfarb et al. |
| 2009/0123361 A1 | 5/2009 | Johannessen et al. |
| 2009/0178671 A1 | 7/2009 | Ahring et al. |
| 2009/0221042 A1 | 9/2009 | Dale et al. |
| 2009/0230040 A1 | 9/2009 | Limcaco |
| 2009/0313976 A1 | 12/2009 | Johannessen et al. |
| 2009/0318670 A1 | 12/2009 | Dale et al. |
| 2010/0159521 A1 | 6/2010 | Cirakovic et al. |
| 2010/0267999 A1 | 10/2010 | Lau et al. |
| 2010/0279361 A1 | 11/2010 | South et al. |
| 2011/0192559 A1 | 8/2011 | Venkatesh et al. |
| 2011/0201091 A1 | 8/2011 | Dale |
| 2011/0290114 A1 | 12/2011 | Campbell et al. |
| 2011/0300269 A1 | 12/2011 | Dale et al. |
| 2012/0064574 A1 | 3/2012 | Tokuyasu et al. |
| 2012/0071308 A1 | 3/2012 | Sekar |
| 2012/0085505 A1 | 4/2012 | Sabourin |
| 2012/0125548 A1 | 5/2012 | Cohen |
| 2012/0125551 A1 | 5/2012 | Cohen et al. |
| 2012/0187228 A1 | 7/2012 | Camp et al. |
| 2012/0325202 A1 | 12/2012 | Dale |
| 2013/0196398 A1 | 8/2013 | Bals et al. |
| 2013/0244293 A1 | 9/2013 | Balan et al. |
| 2013/0247456 A1 | 9/2013 | Dale et al. |
| 2013/0280762 A1 | 10/2013 | Dale et al. |
| 2013/0289268 A1 | 10/2013 | Teymouri et al. |
| 2014/0038243 A1 | 2/2014 | Balan et al. |
| 2014/0227757 A1 | 8/2014 | Jin et al. |

FOREIGN PATENT DOCUMENTS

| | | |
|---|---|---|
| CA | 2573046 A1 | 1/2006 |
| CA | 2610797 A1 | 12/2006 |
| CA | 2752604 A1 | 8/2010 |
| CA | 2762985 C | 7/2013 |
| CA | 2650860 C | 9/2013 |
| CA | 2737704 C | 11/2013 |
| CN | 100999740 A | 7/2007 |
| CN | 101223273 A | 7/2008 |
| CN | 102597247 A | 7/2012 |
| CN | 102939388 A | 2/2013 |
| DE | 20301645 U1 | 4/2003 |
| EP | 0144930 A2 | 6/1985 |
| EP | 0144930 A3 | 1/1987 |
| EP | 1247781 A2 | 10/2002 |
| EP | 1533279 A1 | 5/2005 |
| EP | 1690944 A1 | 8/2006 |
| GB | 1310835 A | 3/1973 |
| GB | 1381728 A | 1/1975 |
| GB | 2122864 A | 1/1984 |
| IN | 249187 | 10/2011 |
| IN | 9645/DELNP/2011 A | 2/2013 |
| JP | 2008161125 A | 7/2008 |
| JP | 2008-535664 A | 9/2008 |
| JP | 2011160753 A | 8/2011 |
| RU | 2215755 C1 | 11/2003 |
| WO | 850133 A1 | 1/1985 |
| WO | 00/61858 A1 | 10/2000 |
| WO | 01/32715 A1 | 5/2001 |
| WO | 0237981 A2 | 5/2002 |
| WO | 03/066577 A1 | 8/2003 |
| WO | 2004/033920 A1 | 4/2004 |
| WO | 2005/091418 A2 | 9/2005 |
| WO | 2006/055362 A1 | 5/2006 |
| WO | 2006/128304 A1 | 12/2006 |
| WO | 2007005918 A2 | 1/2007 |
| WO | 2007005918 A3 | 1/2007 |
| WO | 2007/130337 A1 | 11/2007 |
| WO | 2008020901 A2 | 2/2008 |
| WO | 2008/020901 A3 | 7/2008 |
| WO | 2008/114139 A2 | 9/2008 |
| WO | 2008/114139 A3 | 12/2008 |
| WO | 2009/045527 A1 | 4/2009 |
| WO | 2010/098408 A1 | 9/2010 |

(56) References Cited

FOREIGN PATENT DOCUMENTS

| WO | 2010098409 A1 | 9/2010 |
|---|---|---|
| WO | 2010/121348 A1 | 10/2010 |
| WO | 2010/135679 A1 | 11/2010 |
| WO | 2010147218 A1 | 12/2010 |
| WO | 2011028543 A2 | 3/2011 |
| WO | 2011/046818 A2 | 4/2011 |
| WO | 2011/028543 A3 | 6/2011 |
| WO | 2011/080154 A1 | 7/2011 |
| WO | 2011/125056 A1 | 10/2011 |
| WO | 2011133571 A3 | 10/2011 |
| WO | 2012/012594 A1 | 1/2012 |
| WO | 2012/071312 A2 | 5/2012 |
| WO | 2012/088429 A2 | 6/2012 |
| WO | 2013/106113 A2 | 7/2013 |
| WO | 2013/131015 A1 | 9/2013 |
| WO | 2013/106113 A3 | 10/2013 |
| WO | 2013/163571 A2 | 10/2013 |
| WO | 2013/163571 A3 | 3/2014 |

OTHER PUBLICATIONS

U.S. Appl. No. 11/729,632, NonFinal Rejection Mailed on May 6, 2009.
U.S. Appl. No. 11/729,632, Response Filed Sep. 11, 2009 to Non Final Rejection Mailed on May 6, 2009.
U.S. Appl. No. 11/729,632, Response Filed Oct. 30, 2009 to Non Final Rejection Mailed on May 6, 2009.
U.S. Appl. No. 11/729,632, Notice of Allowance Mailed on Nov. 16, 2009.
U.S. Appl. No. 11/897,119, Restriction Requirement Mailed on Sep. 30, 2011.
U.S. Appl. No. 12/226,763, Office Action Mailed on Aug. 22, 2011.
U.S. Appl. No. 12/226,763, Response Filed Dec. 21, 2011 to Office Action Mailed on Aug. 22, 2011.
U.S. Appl. No. 12/226,763, Final Rejection Mailed on Jan. 10, 2012.
U.S. Appl. No. 12/226,763, Notice of Allowance Mailed on May 29, 2012.
U.S. Appl. No. 12/226,763, Notice of Allowance Mailed on Oct. 1, 2012.
U.S. Appl. No. 12/226,763, Notice of Allowance Mailed on Jan. 22, 2013.
U.S. Appl. No. 12/229,225, NonFinal Rejection Mailed on Aug. 16, 2011.
U.S. Appl. No. 12/229,225, Response Filed Nov. 15, 2011 to NonFinal Rejection Mailed on Aug. 16, 2011.
U.S. Appl. No. 12/229,225, Final Rejection Mailed on Jan. 6, 2012.
U.S. Appl. No. 12/286,913, Response Filed Dec. 28, 2011 to Office Action Mailed on Sep. 28, 2011.
U.S. Appl. No. 12/286,913, NonFinal Rejection Mailed on Mar. 1, 2012.
U.S. Appl. No. 12/286,913, Notice of Allowance Mailed on Oct. 3, 2012.
U.S. Appl. No. 12/763,102, Restriction Requirement Mailed on Sep. 17, 2012.
U.S. Appl. No. 12/763,102, Response Filed Oct. 17, 2012 to Restriction Requirement Mailed on Sep. 17, 2012.
U.S. Appl. No. 12/763,102, Office Action Mailed on Dec. 24, 2012.
U.S. Appl. No. 12/791,703, Response Filed Oct. 11, 2012 to Office Action Mailed on Jul. 27, 2012.
U.S. Appl. No. 12/976,344, Notice of Allowance Mailed on Feb. 23, 2012.
U.S. Appl. No. 12/976,344, Notice of Allowance Mailed on Mar. 27, 2012.
U.S. Appl. No. 13/202,011, NonFinal Rejection Mailed on Sep. 27, 2012.
U.S. Appl. No. 13/202,011, Response file Dec. 21, 2012 to NonFinal Rejection Mailed on Sep. 27, 2012.
U.S. Appl. No. 13/591,092, NonFinal Rejection Mailed on Dec. 13, 2012.

Australian Application No. 2010249409, Examination Report Mailed on Aug. 30, 2012.
Australian Application No. 2010289797, Examination Report Mailed on Oct. 30, 2012.
Australian Application No. 2011201768, Examination Report Mailed on Jun. 21, 2012.
Brazilian Application No. PI0722418-4, Office Action Jan. 14, 2013.
Canadian Application No. 2,650,860, Office Action Mailed on Oct. 24, 2011.
Canadian Application No. 2,650,860, Response Filed Apr. 23, 2012 to Office Action Mailed on Oct. 24, 2011.
Canadian Application No. 2,650,860, Office Action Mailed on Jun. 18, 2012.
Canadian Application No. 2,650,860, Response Filed Dec. 13, 2012 to Office Action Mailed on Jun. 18, 2012.
Canadian Application No. 2,737,704, Office Action Mailed on Jun. 4, 2012.
Canadian Application No. 2,737,704, Response Filed Aug. 22, 2012 to Office Action Mailed on Jun. 4, 2012.
Canadian Application No. 2,737,704, Office Action Mailed on Nov. 5, 2012.
Canadian Application No. 2,737,704, Response Filed Jan. 30, 2013 to Office Action Mailed on Nov. 5, 2012.
Canadian Application No. 2,737,704, Office Action Mailed on Feb. 21, 2013.
Canadian Application No. 2,760,840, Office Action Mailed on Mar. 28, 2012.
Canadian Application No. 2,760,840, Response Filed Jun. 27, 2012 to Office Action mailed on Mar. 28, 2012.
Canadian Application No. 2,760,840, Office Action Mailed on Aug. 6, 2012.
Canadian Application No. 2,760,840, Response Filed Nov. 6, 2012 to Office Action Mailed on Aug. 6, 2012.
Canadian Application No. 2,760,840, Office Action Mailed on Jan. 3, 2013.
Canadian Application No. 2,762,985, Office Action Mailed on Mar. 13, 2012.
Canadian Application No. 2,762,985, Response Filed Jun. 12, 2012 to Office Action Mailed on Mar. 13, 2012.
Canadian Application No. 2,762,985, Office Action Mailed on Jul. 6, 2012.
Canadian Application No. 2,762,985, Response Filed on Oct. 5, 2012 to Office Action Mailed on Jul. 6, 2012.
Canadian Application No. 2,762,985, Notice of Allowance Mailed on Oct. 29, 2012.
Chinese Application No. 200780025394.4, Office Action Mailed Oct. 13, 2011.
Chinese Application No. 200780025394.4, Office Action Mailed Oct. 30, 2012.
Chinese Application No. 200780025394.4, Response Filed Jan. 14, 2013 to Office Action Mailed Oct. 30, 2012.
Chinese Application No. 201110097994.X, Office Action Mailed on Jul. 30, 2012.
European Application No. 07776479.3, Office Action Mailed on May 30, 2012.
European Application No. 07776479.6, Response Filed Sep. 30, 2012 to Office Action Mailed on May 30, 2012.
European Application No. 07776479.3, Office Action Mailed on Dec. 5, 2012.
European Application No. 10778488.6, Office Action Mailed on Dec. 30, 2011.
European Application No. 10814256.3, Search Report Mailed on Jan. 23, 2013.
European Application No. 11162906.9, Response Filed on Jul. 5, 2012 to Office Action Mailed on Jan. 16, 2012.
European Application No. 11772569.7, Office Action Mailed on Nov. 30, 2012.
Indian Application No. 5933/CHENP/2008, Examination Report Mailed on Oct. 29, 2010.
International Application No. PCT/US07/10415, International Search Report Mailed on Oct. 11, 2007.

(56) References Cited

OTHER PUBLICATIONS

International Application No. PCT/US07/10415, Written Opinion Mailed on Oct. 11, 2007.
International Application No. PCT/US2010/046525, International Preliminary Report on Patentability Mailed on Mar. 8, 2012.
International Application No. PCT/US2010/046525, International Search Report Mailed on Apr. 29, 2011.
International Application No. PCT/US2010/046525, Written Opinion Mailed on Apr. 29, 2011.
International Application No. PCT/US2011/061617, International Search Report Mailed on Jun. 8, 2012.
International Application No. PCT/US2011/066868, International Search Report Mailed on Sep. 19, 2012.
International Application No. PCT/US2011/066868, Written Opinion Mailed on Sep. 19, 2012.
Mexican Application No. MX/a/2011/012357, Office Action.
Adapa, Phani et al., "Compression Characteristics of Selected Ground Agricultural Biomass", Agricultural Engineering International: the CIGR Ejournal. Manuscript 1347, vol. XI, Jun. 2009, 19 pgs.
Alizadeh, Hasan et al., "Pretreatment of Switchgrass by Ammonia Fiber Explosion (AFEX)", Applied Biochemistry and Biotechnology, vol. 121-124, 2005, 9 pgs.
Bergner, Hans., "Archives of Animal Nutrition", Arch. Tierernahr., vol. 30, 1980, 19 pgs.
Carolan, Joseph E. et al., "Technical and Financial Feasibility Analysis of Distributed Bioprocessing Using Regional Biomass Pre-Processing Centers", Journal of Agricultural & Food Industrial Organization, vol. 5 Issue 2, 2007, 29 pgs.
Cen, Peilin et al., "Production of Cellulase by Solid-State Fermentation", Advances in Biochemical Engineering/ Biotechnology, vol. 65, 1999, 24 pgs.
Chahal, D. S., "Bioconversion of Hemicelluloses into Useful Products in an Integrated Process for Food/Feed and Fuel (Ethanol) Production from Biomass", Biotechnology and Bioengineering Symp. No. 14, 1984, 9 pgs.
Chahal, Parminder S. et al., "Production of Cellulase in Solid-State Fermentation with Trichoderma reesei MCG 80 on Wheat Straw", Applied Biochemistry and Biotechnology, vol. 57/58, 1996, 10 pgs.
Chang, Shu-Ting, "The World Mushroom Industry: Trends and Technological Development", International Journal of Medicinal Mushrooms, vol. 8, 2006, pp. 297-314.
Chinedu Nwodo, S et al., "Xylanase Production of Aspergillus niger and Penicillium chrysogenum from Ammonia Pretreated Cellulosic Waste", Research Journal of Microbiology, vol. 3(4), 2008, 246-253.
Deshusses, Marc A, "Biological Waste Air Treatment in Biofilters", Current Opinion in Biotechnology, vol. 8, 1997, pp. 335-339.
Kaliyan, N et al., "Roll Press Briquetting and Pelleting of Corn Stover and Switchgrass", American Society of Agricultural and Biological Engineers, vol. 52(2), 2009, pp. 543-555.
Kumar, Parveen et al., "Methods for Pretreatment of Lignocellulosic Biomass for Efficient Hydrolysis and Biofuel Production", Ind. Eng. Chem. Res., Mar. 20, 2009, 18 pgs.
Lynd, Lee R et al., "Microbial Cellulose Utilization: Fundamentals and Biotechnology", Microbiology and Molecular Biology Reviews, Sep. 2002, p. 506-577.
Miller, Norman G., "Phase I Biomass Enhanced Refined Lignite Demonstration Project", ComPAKco, LLC, 2008, 24 pgs.
Mosier, Nathan et al., "Features of Promising Technologies for Pretreatment of Lignocellulosic Biomass", Bioresource Technology, vol. 96, 2005, pp. 673-686.
Perry, John H, "Reactor Design", Chemical Engineers Handbook, 1963, 6 pgs.
Sheridan, B.A. et al., "Assessment of the Influence of Media Particle Size on the Filtration of Odorous Exhause Ventilation Air from a Piggery Facility", Bioresource Technology, vol. 84, 2002, pp. 129-143.
Singhania, Reeta Rani et al., "Advancement and Comparative Profiles in the Production Technologies Using Solid-State and Submerged Fermentation for Microbial Cellulases", Enzyme and Microbial Technology, vol. 46, 2010, pp. 541-549.
Sulbaran De Ferrer et al., "NR 06. Sugar Production From Rice Straw", Arch. Latinoam. Prod. Anim. 5(Supl. 1), 1997, pp. 112-114.
Teymouri, Farzaneh et al., "Optimization of the Ammonia Fiber Explosion (AFEX) Treatment Parameters for Enzymatic Hydrolysis of Corn Stover", Bioresource Technology, vol. 96, 2005, pp. 2014-2018.
Topic 3 R&D on Processes for Solid, Liquid and Gaseous Fuels From Biomass, 20th EU BC&E.
Warzywoda, Michel et al., "Production and Characterization of Cellulolytic Enzymes from Trichoderma reesei Grown on Various Carbon Sources", Bioresource Technology, vol. 39, 1992, pp. 125-130.
Wilson, Jonathan, "A Cost Analysis for the Densification and Transportation of Cellulosic Biomass for Ethanol Production", Kansas State University, 2011, 86 pgs.
Patent Examination Report received for Australian Patent Application No. 2011242896, issued on Oct. 30, 2013, 4 pages.
First Office Action received for Chinese Patent Application No. 201180026819.X, mailed on Mar. 14, 2014, 11 pages of English Translation and 11 pages of the Official.
Alvira et al., "Pretreatment Technologies for an Efficient Bioethanol Production Process Based on Enzymatic Hydrolysis: A Review", Bioresource Technology, vol. 101, No. 13, Jul. 2010, pp. 4851-4861.
Chundawat, "Ultrastructural and Physicochemical Modifications within Ammonia Treated Lignocellulosic Cell Walls and their Influence on Enzymatic Digestibility", Dissertation for Michigan State University, ProQuest, UMI Dissertation Publishing, vol. 1, 2010, 230 pages.
Merino et al., "Progress and Challenges in Enzyme Development for Biomass Utilization", Advances in Biochemical Engineering/ Biotechnology, vol. 108, 2007, pp. 95-120.
Moniruzzaman et al., "Enzymatic Hydrolysis of High-Moisture Corn Fiber Pretreated by AFEX and Recovery and Recycling of the Enzyme Complex", Applied Biochemistry and Biotechnology, vol. 67, No. 1-2, 1997, pp. 113-126.
Extended European Search Report received for European Patent Application No. 11772569.7, mailed on Sep. 19, 2013, 10 pages.
International Search Report and Written Opinion received for PCT Application No. PCT/US2011/033079, mailed on Nov. 22, 2011, 8 pages.
Extended European Search Report received for European Patent Application No. 07776479.3, mailed on May 26, 2010, 6 pages.
Office Action received for European Patent Application No. 10814256.3, mailed on Sep. 6, 2013, 4 pages.
Non-Final Office Action received for U.S. Appl. No. 11/719,158, mailed on Apr. 1, 2009, 6 pages.
Final Office Action received for U.S. Appl. No. 11/719,158, mailed on Aug. 4, 2010, 7 pages.
Notice of Allowance received for U.S. Appl. No. 11/719,158, mailed on Jan. 6, 2011, 4 pages.
Non Final Office Action received for U.S. Appl. No. 11/901,336, mailed on Apr. 27, 2010, 10 pages.
Notice of Allowance received for U.S. Appl. No. 11/901,336, mailed on Aug. 24, 2010, 5 pages.
Partial European Search Report received for EP Patent Application No. 11162906.9, mailed on Aug. 23, 2011, 9 pages.
Extended European Search Report received for European Patent Application No. 11162906.9, mailed on Dec. 13, 2011, 14 pages.
Office Action received for European Patent Application No. 11162906.9, mailed on Jan. 16, 2012, 2 pages.
Office Action received for European Patent Application No. 11162906.9, mailed on Mar. 6, 2013, 5 pages.
Extended European Search Report for European Patent Application No. 11850707.8, mailed on Jul. 3, 2014, 8 pages.
Non Final Office Action received for U.S. Appl. No. 12/214,687, mailed on Jun. 2, 2011, 5 pages.
Restriction Requirement received for U.S. Appl. No. 12/226,850, mailed on Jun. 30, 2011, 4 pages.
Non Final Office Action received for U.S. Appl. No. 12/286,913, mailed on Sep. 28, 2011, 7 pages.

(56) References Cited

OTHER PUBLICATIONS

Final Office Action received for U.S. Appl. No. 12/763,102, mailed on Aug. 5, 2013, 12 pages.
Non-Final Office Action received for U.S. Appl. No. 12/791,703, mailed on Jul. 27, 2012, 7 pages.
Notice of Allowance received for U.S. Appl. No. 12/791,703, mailed on Nov. 8, 2012, 8 pages.
Non-Final Office Action received for U.S. Appl. No. 12/976,344, mailed on Apr. 5, 2013, 12 pages.
Non-Final Office Action received for U.S. Appl. No. 12/976,344, mailed on Apr. 1, 2014, 19 pages.
Restriction Requirement received for U.S. Appl. No. 13/202,011, mailed on Jul. 17, 2012, 6 pages.
Notice of Allowance received for U.S. Appl. No. 13/202,011, mailed on Apr. 9, 2013, 9 pages.
Notice of Allowance received for U.S. Appl. No. 13/202,011, mailed on Nov. 8, 2013, 7 pages.
Notice of Allowance received for U.S. Appl. No. 13/458,830, mailed on Jul. 9, 2014, 8 pages.
Advisory Action received for U.S. Appl. No. 13/591,092, mailed on Jun. 6, 2013, 3 pages.
Final Office Action received for U.S. Appl. No. 13/591,092, mailed on Mar. 25, 2013, 22 pages.
Notice of Allowance received for U.S. Appl. No. 13/591,092, mailed on Feb. 21, 2014, 11 pages.
Non-Final Office Action received for U.S. Appl. No. 13/886,021, mailed on Jun. 30, 2014, 37 pages.
Office Action received for Canadian Patent Application No. 2,650,860, mailed on May 12, 2011, 2 pages.
Notice of Allowance received for Canadian Patent Application No. 2,650,860, mailed on Apr. 2, 2013, 1 page.
Office Action received for Canadian Patent Application No. 2,760,840, mailed on Jul. 30, 2013, 4 pages.
Office Action received for Australian Patent Application No. 2007248736, mailed on Dec. 1, 2009, 2 pages.
Office Action received for Chinese Patent Application No. 201110097994.X, mailed on Jul. 30, 2012, 14 pages of English Translation & 11 pages of Official.
Examination Report received for Australian Patent Application No. 2011348161, mailed on Feb. 21, 2014, 4 pages.
Office Action received for Chinese Patent Application No. 201210287568.7, mailed on Jul. 26, 2013, 3 pages English Translation.
Examination Report received for Australian Patent Application No. 2013205681, mailed on Jun. 27, 2013, 4 pages.
International Preliminary Report on Patentability received for PCT Patent Application No. PCT/US2007/010410, mailed on Dec. 12, 2008, 5 pages.
International Search Report and Written Opinion received for PCT Patent Application No. PCT/US2007/010410, mailed on Jun. 10, 2008, 5 pages.
International Preliminary Report on Patentability received for PCT Patent Application No. PCT/US2007/010415, mailed on Aug. 5, 2008, 6 pages.
International Search Report and Written Opinion received for PCT Patent Application No. PCT/US2008/011488, mailed on Jan. 8, 2009, 6 pages.
International Search Report and Written Opinion received for PCT Application No. PCT/US2010/046525, mailed on Apr. 29, 2011, 9 pages.
International Search Report and Written Opinion received for PCT Patent Application No. PCT/US2011/038524, mailed on Feb. 9, 2012, 7 pages.
International Preliminary Report on Patentability received for PCT Patent Application No. PCT/US2011/066868, mailed on Jul. 4, 2013, 5 pages.
International Search Report and Written Opinion received for PCT Patent Application No. PCT/US2012/059898, mailed on Jul. 26, 2013, 11 pages.
International Search Report and Written Opinion received for PCT Patent Application No. PCT/US2013/028689, mailed on Jun. 4, 2013, 5 pages.
International Search Report received for PCT Patent Application No. PCT/US2013/037935, mailed on Jul. 19, 2013, 4 pages.
Adapa et al., "Pelleting Characteristics of Selected Biomass With and Without Steam Explosion Pretreatment", International Journal of Agricultural and Biological Engineering, vol. 3, No. 3, Sep. 2010, pp. 62-79.
Allan et al., "Replacement of Fish Meal in Diets for Australian Silver Perch, Bidyanus bidyanus: I. Digestibility of Alternative Ingredients", Aquaculture, vol. 186, No. 3-4, Jun. 2000, pp. 293-310.
Viable Herbal Solutions, "Production Techniques to Produce Herbal Extracts", available Online at <http://viablehealth.com/herb/herbs42.html>, Prior to Dec. 17, 2012, 4 pages.
Zhu et al., "Cocurrent Downflow Circulating Fluidized Bed (Downer) Reactors—A State of the Art Review", The Canadian Journal of Chemical Engineering, vol. 73, No. 5, pp. 662-677.
Bagga et al., "Evidence for the Occurrence of Polyamine Oxidase in the Dicotyledonous Plant *Medicago sativa* L. (alfalfa)", Plant Cell Reports, ISSN: 0721-77141991, pp. 550-554.
Balan et al., "Lignocellulosic Biomass Pretreatment Using AFEX", Biofuels: Methods and Protocols, Methods in Molecular Biology, vol. 581, Chapter 5, 2009, pp. 61-77.
Balan et al., "Mushroom Spent Straw: A Potential Substrate for an Ethanol-Based Biorefinery", Journal of Industrial Microbiology and Biotechnology, vol. 35, No. 5, 2008, pp. 293-301.
Baldrian et al., "Variability of Laccase Activity in the White-Rot Basidiomycete Pleurotus ostreatus", Folia Microbiologica, vol. 47, No. 4, 2002, pp. 385-390.
Bals et al., "Enzymatic Hydrolysis of Distiller's Dry Grain and Solubles (DDGS) Using Ammonia Fiber Expansion Pretreatment", Energy & Fuels, vol. 20, No. 6, American Chemical Society, Oct. 2006, pp. 2732-2736.
Bals et al., "Evaluating the Impact of Ammonia Fiber Expansion (AFEX) Pretreatment Conditions on the Cost of Ethanol Production", Bioresource Technology, vol. 102, 2011, pp. 1277-1283.
Beale et al., "Leaf Photosynthesis in the C4-Grass Miscanthus X giganteus, Growing in the Cool Temperate Climate of Southern England", Journal of Experimental Botany, vol. 47, No. 295, Feb. 1996, pp. 267-273.
Belyea et al., "Element Concentrations of Dry-Grind Corn-Processing Streams", Applied Biochemistry and Biotechnology, vol. 134, No. 2, 2006, pp. 113-128.
Betschart et al., "Extractability and Solubility of Leaf Protein", J. Agr. Food Chem., vol. 21, No. 1, 1973, pp. 60-65.
Boluk, Yaman, "Acid-Base Interactions and Swelling of Cellulose Fibers in Organic Liquids", Cellulose, vol. 12, No. 6, Dec. 2005, pp. 577-593.
Bothast et al., "Biotechnological Processes for Conversion of Corn into Ethanol", Appl Microbiol Biotechnol, vol. 67, No. 1, Apr. 2005, pp. 19-25.
Christian et al., "Degradation of Xenobiotic Compounds by Lignin-Degrading White-Rot Fungi: Enzymology and Mechanisms Involved", Indian Journal of Experimental Biology, vol. 43, Apr. 2005, pp. 301-312.
Chundawat et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.
Chundawat et al., "Multi-scale Visualization and Characterization of Lignocellulosic Plant Cell Wall Deconstruction During Thermochemical Pretreatment", Energy & Environmental Science, vol. 4, The Royal Society of Chemistry, 2011, pp. 973-984.
Clifton-Brown et al., "Performance of 15 Miscanthus Genotypes at Five Sites in Europe", Agronomy Journal, vol. 93, No. 5, 2001, pp. 1013-1019.
Cohen et al., "Biotechnological Applications and Potential of Wood-Degrading Mushrooms of the Genus Pleurotus", Appl Microbial Biotechnol, vol. 58, Feb. 2002, pp. 582-591.
Cosgrove, Daniel J., "Growth of the Plant Cell Wall", Nature Reviews, Molecular Cell Biology, Nov. 6, 2005, pp. 850-861.

(56) References Cited

OTHER PUBLICATIONS

Dale et al., "Fermentation of Lignocellulosic Materials Treated by Ammonia Freeze-Explosion", Developments in Industrial Microbiology, vol. 26, The Society for Industrial Microbiology, 1985, pp. 223-233.

Eggeman, T., "Boundary Analysis for H2 Production by Fermentation", NREL National Renewal Energy Laboratory, Subcontract Report NREL/SR-560-36129, May 2005, 17 pages.

El-Adawy et al., "Nutritional Potential and Functional Properties of Sweet and Bitter Lupin Seed Protein Isolates", Food Chemistry, vol. 74, No. 4, 2001, pp. 455-462.

"Energy Policy Act of 2005", Public Law 109-58, 119 Stat. 1067, Aug. 8, 2005, 11 pages.

Erickson, David R., "Edible Fats and Oils Processing: Basic Principles and Modern Practices", AOCS Press, Netherlands, 1990, 6 pages.

RFA Renewal Fuels Association, "Ethanol Biorefinery Locations—U.S. Fuel Ethanol Industry Biorefineries and Production Capacity" available online at <http://www.ethanolrfa.org/industry/locations>, Prior to Dec. 17, 2012, 4 pages.

Felix et al., "In Vitro and In Vivo Digestibility of Soya-Bean Straw Treated with Various Alkalis", Animal Production, vol. 51, No. 1, British Society of Animal Production, 1990, pp. 47-59.

Fernandez et al., "Protein Extraction from Atriplex lampa Leaves: Potential Use as Forage for Animals used for Human Diets", Plant Foods for Human Nutrition, vol. 54, 1999, pp. 251-259.

Ferrer et al., "Increasing Nutrient Availability of Feather Meal for Ruminants and Non-Ruminants Using an Ammonia Pressurisation/ Depressurisation Process", Journal of the Science of Food and Agriculture, vol. 79, 1999, pp. 828-832.

Ferrer et al., "Optimizing Ammonia Pressurization/Depressurization Processing Conditions to Enhance Enzymatic Susceptibility of Dwarf Elephant Grass", Applied Biochemistry and Biotechnology, vol. 84-86, No. 1-9, Mar. 2000, pp. 163-179.

Fernandez et al., "Pilot Plant Production of an Edible Alfalfa Protein Concentrate", Journal of Food Science, vol. 46, No. 5, Sep. 1981, pp. 1514-1517.

Foster et al., "Enzymatic Hydrolysis of Ammonia-Treated Sugar Beet Pulp", Applied Biochemistry and Biotechnology, vol. 91-93, 2001, pp. 269-282.

Fulks et al., "A Review of Solid Materials as Alternative Ammonia Sources for Lean NOx Reduction with SCR", Technical Paper No: 2009-01-0907, SAE International, 2009, 13 pages.

Gao et al., "Mixture Optimization of Six Core Glycosyl Hydrolases for Maximizing Saccharification of Ammonia Fiber Expansion (AFEX) Pretreated Corn Stover", Bioresource Technology, vol. 101, Issue 8, Apr. 2010, pp. 2770-2781.

Gollapalli et al., "Predicting Digestibility of Ammonia Fiber Explosion (AFEX)-Treated Rice Straw", Applied Biochemistry and Biotechnology, vol. 98-100, 2002, pp. 23-35.

Gray et al., "Bioethanol", Current Opinion in Chemical Biology, vol. 10, 2006, pp. 141-146.

Greene et al., "Growing Energy: How Biofuels Can Help End America's Oil Dependence", Natural Resources Defense Council, Dec. 2004, 86 pages.

Hahn-Hagerdal et al., "Bio-Ethanol—The Fuel of Tomorrow from the Residues of Today", Trends in Biotechnology, vol. 24, No. 12, Dec. 2006, pp. 549-556.

Hanchar et al., "Separation of Glucose and Pentose Sugars by Selective Enzyme Hydrolysis of AFEX-Treated Corn Fiber", Applied Biochemistry and Biotechnology, vol. 137-140, No. 1-12, 2007, pp. 313-326.

Heaton et al., "A Quantitative Review Comparing the Yields of Two Candidate C4 Perennial Biomass Crops in Relation to Nitrogen, Temperature and Water", Biomass and Bioenergy, vol. 27, No. 1, Jul. 2004, pp. 21-30.

Heaton et al., "Miscanthus for Renewable Energy Generation: European Union Experience and Projections for Illinois", Mitigation and Adaptation Strategies for Global Change, vol. 9, No. 4, Oct. 2004, pp. 433-451.

Holtzapple et al., "The Ammonia Freeze Explosion (AFEX) Process: A Practical Lignocellulose Pretreatment", Applied Biochemistry and Biotechnology, vol. 28-29, No. 1, 1991, pp. 59-74.

Houghton et al., "Fungal Upgrading of Wheat Straw for Straw-Thermoplastics Production", Applied Biochemistry and Biotechnology, vol. 113-116, 2004, pp. 71-93.

Israilides et al., "Bio-technologies of Recycling Agro-Industrial Wastes for the Production of Commercially Important Fungal Polysaccharides and Mushrooms", Biotechnology and Genetic Engineering Reviews, vol. 20, Dec. 2003, pp. 247-259.

Jain et al., "Effect of Ammonia Pretreatment on Switchgrass for Production of Cellulase using Trichoderma reesei Rut C-30", The 31st Symposium on Biotechnology for Fuels and Chemicals, May 4, 2009, 1 page.

Jeoh et al., "Cooperative and Competitive Binding in Synergistic Mixtures of Thermobifida fusca Cellulases Ce15A, Ce16B, and Ce19A", Biotechnol. Prog., vol. 18, No. 4, American Chemical Society and American Institute of Chemical Engineers, 2002, pp. 760-769.

Jin et al., "A Novel Integrated Biological Process for Cellulosic Ethanol Production Featuring High Ethanol Productivity, Enzyme Recycling and Yeast Cells Reuse", Energy & Environmental Science, No. 5, The Royal Society of Chemistry, 2012, 8 pages.

Jin et al., "Two-Step SSCF to Convert AFEX-Treated Switchgrass to Ethanol using Commercial Enzymes and Saccharomyces cerevisiae 424A (LNH-ST)", Bioresource Technology, vol. 101, No. 21, 2010, pp. 8171-8178.

Kamm et al., "Principles of Biorefineries", Applied Microbiology and Biotechnology, vol. 64, No. 2, Apr. 2004, pp. 137-145.

Karunanandaa et al., "Botanical Fractions of Rice Straw Colonized by White-Rot Fungi: Changes in Chemical Composition and Structure", Animal Feed Science Technology, vol. 55, 1995, pp. 179-199.

Kawasaki et al., "Deodorization of Ammonia by Coffee Grounds", Journal of Oleo Science, vol. 55, No. 1, 2006, pp. 31-35.

Keller et al., "Microbial Pretreatment of Biomass—Potential for Reducing Severity of Thermochemical Biomass Pretreatment", Applied Biochemistry and Biotechnology, vol. 105-108, 2003, pp. 27-41.

Kim et al., "Pretreatment of Corn Stover by Aqueous Ammonia", Bioresource Technology, vol. 90, Oct. 2003, pp. 39-47.

Sarikaya et al., "Solid-State Fermentation of Lignocellulosic Plant Residues from Brassica napus by Pleurotus ostreatus", Applied Biochemistry and Biotechnology, vol. 82, No. 1, Oct. 1999, pp. 1-15.

Selig et al., "Enzymatic Saccharification of Lignocellulosic Biomass", National Renewable Energy Laboratory, Technical Report, NREL/TP-510-42629, Mar. 21, 2008, 8 pages.

Sendich et al., "Recent Process Improvements for the Ammonia Fiber Expansion (AFEX) Process and Resulting Reductions in Minimum Ethanol Selling Price", Bioresource Technology, vol. 99, 2008, pp. 8429-8435.

Singh et al., "Composting of a Crop Residue through Treatment with Microorganisms and Subsequent Vermicomposting", Bioresource Technology, vol. 85, No. 2, Nov. 2002, pp. 107-111.

Sluiter et al., "Determination of Structural Carbohydrates and Lignin in Biomass", National Renewable Energy Laboratory, Laboratory Analytical Procedure (LAP), Apr. 25, 2008, 17 pages.

Sokhansanj et al., "Biomass Densification—Cubing Operation and Costs for Corn Stover", Applied Engineering in Agriculture, vol. 20, No. 4, American Society of Agricultural Engineers, 2004, pp. 495-499.

Somerville et al., "Toward a Systems Approach to Understanding Plant Cell Walls", Science, vol. 306, No. 570524 Dec. 24, 2004, pp. 2206-2211.

Steele et al., "Enzyme Recovery and Recycling Following Hydrolysis of Ammonia Fiber Explosion—Treated Corn Stover", Applied Biochemistry and Biotechnology, vol. 121-124, No. 1-3, 2005, pp. 901-910.

Sukumaran et al., "Cellulase Production Using Biomass Feed Stock and its Application in Lignocellulose Saccharification for Bio-Ethanol Production", Renewable Energy, vol. 34, No. 2, Feb. 2009, pp. 421-424.

(56) References Cited

OTHER PUBLICATIONS

Sulbaran-De-Ferrer et al., "Enzymatic Hydrolysis of Ammonia-Treated Rice Straw", Applied Biochemistry and Biotechnology, vol. 105-108, 2003, pp. 155-164.
SunOpta Bioprocess Group, "SunOpta BioProcess Solutions", Customer Manual, Prior to May 2, 2013, 20 pages.
Suto et al., "Induction and Catabolite Repression Mechanisms of Cellulase in Fungi", Journal of Bioscience and Bioengineering, vol. 92, No. 4, 2001, pp. 305-311.
Tabil et al., "Biomass Feedstock Pre-Processing—Part 1: Pre-Treatment", Chapter 18, Biofuel's Engineering Process Technology, Aug. 2011, pp. 411-438.
Taniguchi et al., "Evaluation of Pretreatment with Pleurotus ostreatus for Enzymatic Hydrolysis of Rice Straw", Journal of Bioscience and Bioengineering, vol. 100, No. 6, Dec. 2005, pp. 637-643.
Tanner Industries, Inc., "Anhydrous Ammonia", Customer Manual, Dec. 2006, 17 pages.
Teymouri et al., "Hydrolysis of Ground and Unground AFEX Treated Corn Stover with Different Combinations of Cellulase and Xylanase", 27th Symposium on Biotechnology for Fuels and Chemicals, May 1-4, 2005, 21 pages.
Theerarattananoon et al., "Effects of the Pelleting Conditions on Chemical Composition and Sugar Yield of Corn Stover, Big Bluestem, Wheat Straw, and Sorghum Stalk Pellets", Bioprocess Biosyst. Eng., vol. 35, No. 4, May 2012, pp. 615-623.
Tolan Jeffrey S., "Iogen's Demonstration Process for Producing Ethanol from Cellulosic Biomass", Fuel-oriented Biorefineries, Chapter 9, Biorefineries—Industrial Processes and Products, 2006, pp. 193-208.
Turner et al., "Disruption of Forage Structure with an Ammonia Fiber Explosion Process", Proceedings Western Section, American Society of Animal Science, vol. 41, 1990, pp. 494-497.
Uraki et al., "Body Temperature-Responsive Gels Derived from Hydroxypropylcellulose Bearing Lignin II: Adsorption and Release Behavior", Cellulose, vol. 13, No. 3, Jun. 2006, pp. 225-234.
Urribarri et al., "Leaf Protein from Ammonia-Treated Dwarf Elephant Grass (*Pennisetum purpureum Schum* cv. *Mott*)" Applied Biochemistry and Biotechnology, vol. 121-124, 2005, pp. 721-730.
Van Horn et al., "Complete Rations for Growing Dairy Replacements Utilizing By-Product Feed stuffs", Journal of Dairy Science, vol. 63, 1980, pp. 1465-1474.
Vrije et al., "Pretreatment of Miscanthus for Hydrogen Production by Thermotoga elfii", International Journal of Hydrogen Energy, vol. 27, No. 11-12, 2002, pp. 1381-1390.
Waiss et al., "Improving Digestibility of Straws for Ruminant Feed by Aqueous Ammonia", Journal of Animal Science, vol. 35, No. 1, 1972, pp. 109-112.
Walter, A., "Industrial Uses of Biomass Energy: New Technologies for Modern Biomass Energy Carriers", Taylor & Francis, Chapter 9, edited by Rosillo-Calle F., Bajay SV, Rothman H., 2000, pp. 200-253.
Wang et al., "Cost Estimates and Sensitivity Analyses for the Ammonia Fiber Explosion Process", Applied Biochemistry and Biotechnology, vol. 70-72, No. 1, 1998, pp. 51-66.
Wheals et al., "Fuel Ethanol after 25 Years", Trends in Biotechnology, vol. 17, No. 12, Dec. 1999, pp. 482-487.
Williams et al., "An Initial Assessment of Spent Mushroom Compost as a Potential Energy Feedstock", Bioresource Technology, vol. 79, No. 3, Sep. 2001, pp. 227-230.
Wyman et al., "Comparative Sugar Recovery Data From Laboratory Scale Application of Leading Pretreatment Technologies to Corn Stover", Bioresource Technology, vol. 96, No. 18, 2005, pp. 2026-2032.
Wyman et al., "Coordinated Development of Leading Biomass Pretreatment Technologies", Bioresource Technology, vol. 96, No. 18, 2005, pp. 1959-1966.
Ye et al., "Improving Accessibility and Reactivity of Cellulose of Annual Plants for the Synthesis of Methylcellulose", Cellulose, vol. 12, No. 5, Oct. 2005, pp. 507-515.

Yoon et al., "Ammonia-Recycled Percolation Process for Pretreatment of Biomass Feedstock", Applied Biochemistry and Biotechnology, vol. 51/52, 1995, pp. 5-19.
Zhang et al., "A Transition from Cellulose Swelling to Cellulose Dissolution by o-Phosphoric Acid: Evidence from Enzymatic Hydrolysis and Supramolecular Structure", Biomacromolecules, vol. 7, No. 2, Feb. 2006, pp. 644-648.
Zhang et al., "Oyster Mushroom Cultivation with Rice and Wheat Straw", Bioresource Technology, vol. 82, No. 3, May 2002, pp. 277-284.
Zhang et al., "Effect Effect of Different Treatment Conditions on Biomass Binder Preparation for Lignite Briquette", Fuel Processing Technology, vol. 73, 2001, pp. 185-196.
Zhang et al., "Toward an Aggregated Understanding of Enzymatic Hydrolysis of Cellulose: Noncomplexed Cellulase Systems", Biotechnology and Bioengineering, vol. 88, No. 7, Dec. 30, 2004, pp. 797-824.
Zhao et al., "Organosolv Pretreatment of Lignocellulosic Biomass for Enzymatic Hydrolysis", Applied Microbiology and Biotechnology, Vo. 82, 2009, pp. 815-827.
Zhong et al., "Optimization of Enzymatic Hydrolysis and Ethanol Fermentation from AFEX-Treated Rice Straw", Applied Microbiology and Biotechnology, vol. 84, No. 4, Springer-Verlag, Sep. 2009, pp. 667-676.
Zhou et al., "Gene Integration and Expression and Extracellular Secretion of Erwinia chrysanthemi Endoglucanase CelY (celY) and CelZ (celZ) in Ethanologenic Klebsiella oxytoca P2†", Applied and Environmental Microbiology, vol. 67, No. 1, American Society for Microbiology, 2001, pp. 6-14.
Kim et al., "Enhancement of the Enzymatic Digestibility of Waste Newspaper Using Tween", Applied Biochemistry and Biotechnology, vols. 129-132, Humana Press Inc., 2006, pp. 486-495.
Kim et al., "Lime Pretreatment and Enzymatic Hydrolysis of Corn Stover", Bioresource Technology, vol. 96, No. 18, Dec. 2005, pp. 1994-2006.
Kim et al., "Pretreatment and Fractionation of Corn Stover by Ammonia Recycle Percolation Process", Bioresource Technology, vol. 96, No. 18, 2005, pp. 2007-2013.
Kim et al., "Pretreatment of Corn Stover by Low-Liquid Ammonia Recycle Percolation Process", Applied Biochemistry and Biotechnolology, vol. 133, Apr. 2006, pp. 41-57.
Knauf et al., "Lignocellulosic Biomass Processing: A Perspective", International Sugar Journal, vol. 106, No. 1263, 2004, pp. 147-150.
Kudra et al., "Advanced Drying Technologies: Superheated Steam Drying", Marcel Dekker, Inc., 2002, pp. 81-111.
Kumar et al., "Does Densification Influence the Steam Pretreatment and Enzymatic Hydrolysis of Softwoods to Sugars?", Bioresource Technology, vol. 121, Oct. 2012, pp. 190-198.
Ladisch et al., "Building a Bridge to the Ethanol Industry—Follow-Up Project", National Renewable Energy Laboratory, Apr. 2003, 36 pages.
Lau et al, "Cellulosic Ethanol Production from AFEX-treated Corn Stover Using *Saccharomyces cerevisiae* 424A(LNH-ST)", PNAS, vol. 106, No. 5, Feb. 3, 2009, pp. 1368-1373.
Lau et al., "Comparing the Fermentation Performance of *Escherichia coli* KO11, *Saccharomyces cerevisiae* 424A(LNH-ST) and Zymomonas mobilis AX101 for Cellulosic Ethanol Production", Biotechnology for Biofuels, vol. 3, No. 11, 2010, 10 pages.
Lau et al., "Ethanol Fermentation of *E. coli* KO11 in Hydrolysate from AFEX-treated Corn Stover" Biomass Conversion Research Laboratory, Department of Chemical Engineering and Materials Science, Prior to May 2, 2013, 1 page.
Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, 2009, 11 pages.
Laureano-Perez et al., "Understanding Factors That Limit Enzymatic Hydrolysis of Biomass—Characterization of Pretreated Corn Stover", Applied Biochemistry and Biotechnology, vol. 121-124, 2005, pp. 1081-1099.
Lin et al., "Ethanol Fermentation From Biomass Resources: Current State and Prospects", Applied Microbiology and Biotechnology, vol. 69, No. 6, Feb. 2006, pp. 627-642.

(56) References Cited

OTHER PUBLICATIONS

Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.
Lloyd et al., "Combined Sugar Yields for Dilute Sulfuric Acid Pretreatment of Corn Stover Followed by Enzymatic Hydrolysis of the Remaining Solids", Bioresource Technology, vol. 96, No. 18, Dec. 2005, pp. 1967-1977.
Lovrien et al., "Assays for Total Protein", Current Protocols in Protein Science, John Wiley & Sons, Inc., 1995, 24 pages.
Lu et al., "Cellulase Adsorption and an Evaluation of Enzyme Recycle During Hydrolysis of Steam-Exploded Softwood Residues", Applied Biochemistry and Biotechnology, vol. 98-100, 2002, pp. 641-654.
Madakadze et al., "Cutting Frequency and Nitrogen Fertilization Effects on Yield and Nitrogen Concentration of Switchgrass in a Short Season Area", Crop Science, vol. 39, No. 2, Mar.-Apr. 1999, pp. 552-557.
Mani et al., "Economics of Producing Fuel Pellets from Biomass", Applied Engineering in Agriculture, vol. 22, No. 3, pp. 421-426.
Mani et al., "Grinding Performance and Physical Properties of Wheat and Barley Straws, Corn Stover, and Switchgrass", Biomass and Bioenergy, vol. 27, No. 4, Oct. 2004, pp. 339-352.
Mantanis et al., "Swelling of Compressed Cellulose Fiber Webs in Organic Liquids", Cellulose, vol. 2, No. 1, 1995, pp. 1-22.
Marshall et al., "Complete Rations for Dairy Cattle. II. Sugarcane Bagasse Pellets as Roughage in Blended Rations for Lactating Cows", Journal of Dairy Science, vol. 58, No. 6, Jun. 1975, pp. 896-900.
Martinez et al., "Biodegradation of Lignocellulosics: Microbial, Chemical, and Enzymatic Aspects of the Fungal Attack of Lignin", International Microbiology, vol. 8, 2005, pp. 195-204.
Mellerowicz et al., "Unravelling Cell Wall Formation in the Woody Dicot Stem", Plant Molecular Biology, vol. 47, 2001, pp. 239-274.
Mohan et al., "Pyrolysis of Wood/Biomass for Bio-Oil: A Critical Review", Energy Fuels, vol. 20, No. 3, 2006, pp. 848-889.
Mosier et al., "Optimization of pH Controlled Liquid Hot Water Pretreatment of Corn Stover", Bioresource Technology, vol. 96, 2005, pp. 1986-1993.
Nenkova et al., "Production of Phenol Compounds by Alkaline Treatment of Technical Hydrolysis Lignin and Wood Biomass", Chemistry of Natural Compounds, vol. 44, No. 2, 2008, pp. 182-185.
Obodai et al., "Comparative Study on the Growth and Yield of Pleurotus ostreatus Mushroom on Different Lignocellulosic By-Products", Journal of Industrial Microbiology and Biotechnology, vol. 30, No. 3, 2003, pp. 146-149.
O'Connor, James J., "Ammonia Explosion Pulping : A New Fiber Separation Process", Tappi, vol. 55, No. 3, Mar. 1972, pp. 353-358.
Ohara, H., "Biorefinery", Applied Microbiology and Biotechnology, vol. 62, No. 5-6, Oct. 2003, pp. 474-477.
Ordonez et al., "Obtaining a Protein Concentrate From Integral Defatted Sunflower Flour", Bioresource Technology, vol. 78, No. 2, 2001, pp. 187-190.
Ozturk et al., "Splitting Tendency of Cellulosic Fibers. Part 2: Effects of Fiber Swelling in Alkali Solutions", Cellulose, vol. 13, No. 4, Aug. 2006, pp. 403-409.
Pandey et al., "Economic Utilization of Crop Residues for Value Addition: A Futuristic Approach", Journal of Scientific & Industrial Research, vol. 59, Jan. 2000, pp. 12-22.
Park et al., "Investigation and Optimization of the Factors Influencing Sorghum Protein Extraction", Journal of Agricultural and Food Chemistry, vol. 51, No. 24, American Chemical Society, Oct. 2003, pp. 7050-7054.
Paul et al., "Liquid-Vapor Interfacial Properties of Water-Ammonia Mixtures: Dependence on Ammonia Concentration", The Journal of Chemical Physics, vol. 123, No. 17, 2005, 10 pages.
Piva et al., "Detoxification Methods of Aflatoxins. A Review", Nutrition Research, vol. 15, No. 5, May 1995, pp. 767-776.
Poppe, J., "Use of Agricultural Waste Materials in the Cultivation of Mushrooms", Science and Cultivation of Edible Fungi, vol. 1-2, 2000, pp. 3-23.
Prévot-D'Alvise et al., "Development of a Pilot Process for the Production of Alfalfa Peptide Isolate", Journal of Chemical Technology and Biotechnology, vol. 78, Issue 5, May 2003, pp. 518-528.
Ragauskas et al., "The Path Forward for Biofuels and Biomaterials", Science, vol. 311, No. 5760, Jan. 27, 2006, pp. 484-489.
Rajagopalan et al., "Enhancing Profitability of Dry Mill Ethanol Plants", Applied Biochemistry and Biotechnology, vol. 120, No. 1, 2005, pp. 37-50.
Rausch et al., "The Future of Coproducts from Corn Processing", Applied Biochemistry and Biotechnology, vol. 128, 2006, pp. 47-86.
Renewable Fuels Association, "From Niche to Nation: Ethanol Industry", Outlook, Renewable Fuels Association, Washington DC, 2006, 24 pages.
Rijal et al., "Combined Effect of Pelleting and Pretreatment on Enzymatic Hydrolysis of Switchgrass", Bioresource Technology, vol. 116, 2012, pp. 36-41.
Rollin et al., "Increasing Cellulose Accessibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 1, 2011, pp. 22-30.
Roman-Ponce et al., "Complete Rations for Dairy Cattle. V. Interaction of Sugarcane Bagasse Quantity and Form with Soybean Meal, Urea, and Starea", Journal of Dairy Science, vol. 58, No. 9, Sep. 1975, pp. 1320-1327.
Rosa et al., "Integrated Production of Ethanol Fuel and Protein From Coastal Bermudagrass", Applied Biochemistry and Biotechnology, vol. 45-46, No. 1, 1994, pp. 483-497.
Saha Badal C., "Hemicellulose Bioconversion", Journal of Industrial Microbiology and Biotechnology, vol. 30, No. 5, May 2003, pp. 279-291.
Sanchez et al., "Biodegradation of Viticulture Wastes by Pleurotus: A Source of Microbial and Human Food and Its Potential Use in Animal Feeding", Journal of Agriculture and Food Chemistry, vol. 50, No. 9, Apr. 24, 2002, pp. 2537-2542.
Sanderson et al., "Switchgrass as a Sustainable Bioenergy Crop", Bioresource Technology, vol. 56, No. 1, Apr. 1996, pp. 83-93.
Advisory Action received for U.S. Appl. No. 12/763,102, mailed on Dec. 6, 2013, 3 pages.
Office Action received for Canadian Patent Application No. 2,797,193, mailed on Jan. 8, 2014, 3 pages.
Dale et al., "Extrusion Processing for Ammonia Fiber Explosion (AFEX)", Applied Biochemistry and Biotechnology, vols. 77-79, 1999, pp. 35-45.
Eriksson et al., "A Model Explaining Declining Rate in Hydrolysis of Lignocellulose Substrates with Cellobiohydrolase I (Cel7A) and Endoglucanase I (Cel7B) of Trichoderma Reesei", Applied Biochemistry and Biotechnology, vol. 101, No. 1, Apr. 2002, pp. 41-60.
Habibi et al., "Optimization of Cellouronic Acid Synthesis by TEMPO-Mediated Oxidation of Cellulose III from Sugar Beet Pulp", Cellulose, vol. 15, No. 1, Feb. 2008, pp. 177-185. (Abstract).
Igarashi et al., "Activation of Crystalline Cellulose-To-Cellulose III Results in Efficient Hydrolysis by Cellobiohydrolase", FEBS Journal, vol. 274, No. 7, Apr. 2007, pp. 1785-1792.
Ishikawa et al., "Determination of Parameters in Mechanical Model for Cellulose III Fibre", Polymer, vol. 39, No. 10, May 1998, pp. 1875-1878.
Klemm et al., "General Considerations on Structure and Reactivity of Cellulose", Chapter 2.1-2.1.4, Comprehensive Cellulose Chemistry: Fundamentals and Analytical Methods, vol. 1, 2004, pp. 9-29.
Lewin et al., "Effect Effect of Liquid Anhydrous Ammonia in the Structure and Morphology of Cotton Cellulose", Journal of Polymer Science Part C: Polymer Symposia, vol. 36, No. 1, 1971, pp. 213-229.
Owen et al., "An Infrared Study of the Effect of Liquid Ammonia on Wood Surfaces", Journal of Molecular Structure, vol. 198, Jul. 1989, pp. 435-449.
Perez et al., "TEMPO-Mediated Oxidation of Cellulose III", Biomacromolecules, vol. 4, No. 5, Sep.-Oct. 2003, pp. 1417-1425.

(56) References Cited

OTHER PUBLICATIONS

Sun et al., "Hydrolysis of Lignocellulosic Materials for Ethanol Production: A Review", Bioresource Technology, vol. 83, No. 1, 2002, pp. 1-11.
Sarko et al., "Packing Analysis of Carbohydrates and Polysaccharides. 7. Crystal Structure of Cellulose IIII and Its Relationship to Other Cellulose Polymorphs", Macromolecules, vol. 9, No. 5, Sep. 1976, pp. 857-863.
Wada et al., "Neutron Crystallographic and Molecular Dynamics Studies of the Structure of Ammonia-Cellulose I: Rearrangement of Hydrogen Bonding during the Treatment of Cellulose with Ammonia", Cellulose, vol. 18, No. 1, Apr. 2011, pp. 191-206.
Wada et al., "Polymorphism of Cellulose I Family: Reinvestigation of Cellulose IVI", Biomacromolecules, vol. 5, No. 4, Jul.-Aug. 2004, pp. 385-391. (Abstract).
Yatsu et al., "Conversion of Cellulose I to Stable Cellulose III", Textile Research Journal, vol. 56, No. 7, Jul. 1986, pp. 419-424.
Yui et al., "Structure Conversions of Cellulose III Crystal Models in Solution State: A Molecular Dynamics Study", Cellulose, vol. 17, No. 4, Aug. 2010, pp. 679-691.
Zugenmaier, "Conformation and Packing of Various Crystalline Cellulose Fibers", Progress in Polymer Science, vol. 26, No. 9, Nov. 2001, pp. 1341-1417.
Communication pursuant to Article 94(3) EPC received for European Patent Application No. 11162906.9, mailed on Dec. 10, 2014, 3 pages.
Examination Report received for Indian Patent Application No. 1148/DEL/2011, mailed on Feb. 11, 2015, 4 pages.
Communication pursuant to Article 94(3) EPC received for European Patent Application No. 11772569.7, mailed on Jan. 23, 2015, 4 pages.
Non Final Office Action received for U.S. Appl. No. 12/763,102, mailed on Sep. 23, 2014, 13 pages.
Notice of Allowance received for U.S. Appl. No. 12/763,102, mailed on Jan. 13, 2015, 10 pages.
Notice of Allowance received for U.S. Appl. No. 12/976,344, mailed on Nov. 28, 2014, 10 pages.
Notice of Allowance received for U.S. Appl. No. 13/835,766, mailed on Oct. 2, 2014, 8 pages.
Notice of Allowance received for U.S. Appl. No. 13/835,766, mailed on Jan. 28, 2015, 7 pages.
Final Office Action received for U.S. Appl. No. 13/886,021, mailed on Feb. 24, 2015, 31 pages.
Restriction Requirement received for U.S. Appl. No. 13/997,043, mailed on Jan. 23, 2015, 11 pages.
Office Action received for Canadian Patent Application No. 2,797,193, mailed on Oct. 1, 2014, 2 pages.
Office Action received for Canadian Patent Application No. 2,822,644, mailed on Sep. 8, 2014, 2 pages.
Office Action received for Chinese Patent Application No. 201180026819.X, mailed on Nov. 20, 2014, 9 pages of English translation and 8 pages of Official Notice.
Office Action received for Chinese Patent Application No. 201180062555.3, mailed on Oct. 14, 2014, 9 pages of English translation and 8 pages of Official Notice.
Office Action received for Chinese Patent Application No. 201210287568.7, mailed on Nov. 4, 2014, 3 pages of English translation and 3 pages of Official Notice.
Office Action received for Mexican Patent Application No. MX/a/2011/004206, mailed on Dec. 22, 2014, 1 page of English translation.
Campbell et al., "A Packed Bed Ammonia Fiber Expansion Reactor System for Pretreatment of Agricultural Residues at Regional Depots", Biofuels, vol. 4, No. 1, Feb. 2013, pp. 23-34.
Non Final Office Action received for U.S. Appl. No. 13/886,021, mailed on Oct. 30, 2015, 22 pages.
Fourth Office Action received for China Patent Application No. 201180026819.X mailed on Nov. 11, 2015, 8 pages. (4 pages of English Translation and 4 pages of Detailed Office Action).
Restriction Requirement received for U.S. Appl. No. 14/251,921 mailed on Sep. 3, 2015, 6 pages.
Office Action received for Canadian Patent Application No. 2,797,193, mailed on Jun. 13, 2014, 3 pages.
Notice of Reexamination received for Chinese Patent Application No. 201110097994.X, mailed on Apr. 2, 2015, 7 Page of English translation and 7 pages of Detailed Office Action.
Third Office Action received for Chinese Patent Application No. 201180026819.X, mailed on Apr. 16, 2015, 5 pages of English translation and 4 pages of Official Notice.
Office Action received for Mexican Patent Application No. MX/a/2012/012149 , mailed on Aug. 7, 2015, 3 pages.
Preliminary Rejection received for Brazilian Patent Application No. PI0711139-8, mailed on Sep. 29, 2015, 11 pages.
Preliminary Rejection received for Brazilian Patent Application No. PI0722418-4, mailed on Sep. 29, 2015, 6 pages.
Extended European Search Report received for European Patent Application No. 14174649.5, mailed on Dec. 23, 2014, 8 pages.
Office Action received for EP Patent Application No. 11772569.7, mailed on Jul. 29, 2015, 3 pages.
Official Communication Pursuant to Article 94(3) EPC received for European Patent Application No. 14174649.5, mailed on Sep. 30, 2015, 5 pages.
Alizadeh et al., "Pretreatment of Switchgrass by Ammonia Fiber Explosion (AFEX)", Applied Biochemistry and Biotechnology, vol. 121-124, 2005, pp. 1133-1141.
Office Action received for EP Patent Application No. 11772569.7, mailed on Sep. 28, 2015, 5 pages.
Preliminary Rejection received for BR Application PI0711139-8, mailed on Jan. 22, 2016, 6 pages.
Office Action received for BR Patent Application No. PI0722418-4, mailed on Feb. 5, 2016, 4 pages.
Notice of Decision to Grant Received for Chinese Patent Application No. 201180026819.X, mailed on Apr. 20, 2016, 2 pages.
Office Action Received for Mexican Patent Application No. MX/a/2012/012149 mailed on Mar. 16, 2016, 2 pages.
Office Action received for U.S. Appl. No. 13/886,021, mailed on Jun. 14, 2016, 26 pages.

* cited by examiner

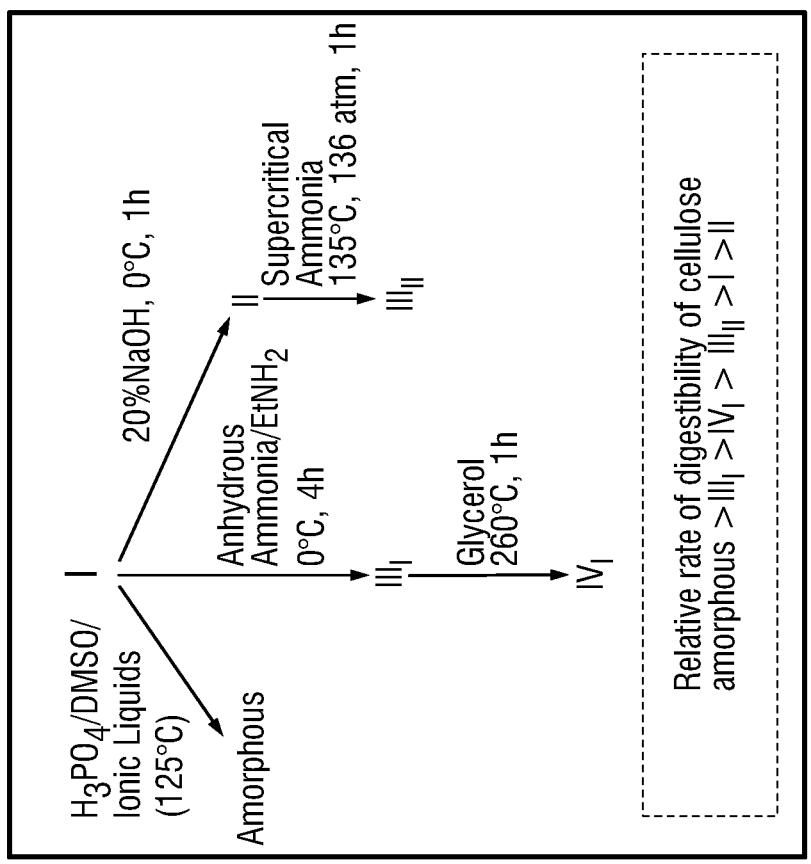
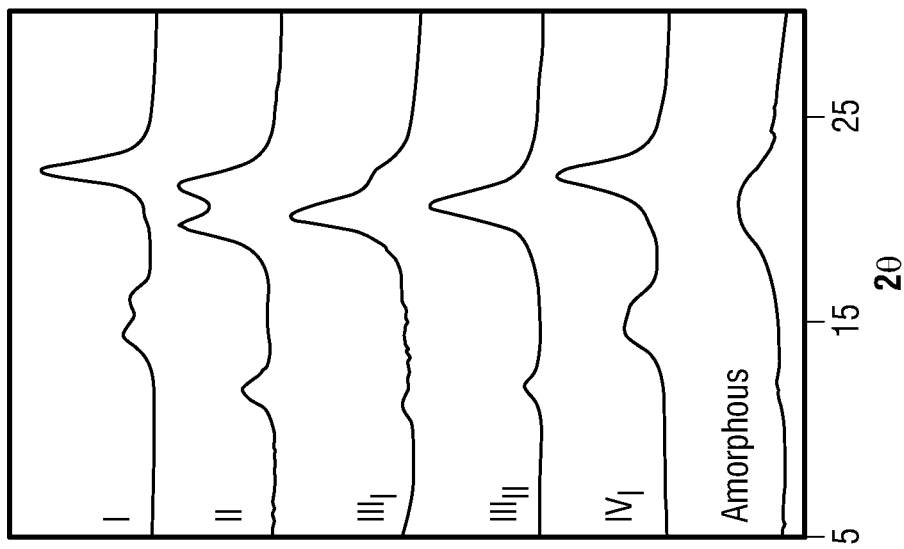
FIG. 3A
FIG. 3B

METHODS FOR PRODUCING EXTRACTED AND DIGESTED PRODUCTS FROM PRETREATED LIGNOCELLULOSIC BIOMASS

This application is a U.S. National Stage Filing under 35 U.S.C. 371 from International Application No. PCT/US2011/033079, filed Apr. 19, 2011, and published in English as WO WO/2011/133571 on Oct. 27, 2011, which claims the benefit under 35 U.S.C. 119 (e) of U.S. Provisional Application Ser. No. 61/325,560 filed on Apr. 19, 2010, which applications and publications are hereby incorporated by reference in their entireties.

STATEMENT OF GOVERNMENT RIGHTS

This invention was made with government support under DE-FC02-07ER64494 awarded by the U.S. Department of Energy. The government has certain rights in the invention.

BACKGROUND

Cellulosic biomass can be used for the production of various products. However, many conventional methods are very expensive, requiring high capital expenditures, such as for high pressure reactors and large amounts of additives.

SUMMARY OF THE INVENTION

The invention generally relates to methods for improving the digestibility of lignocellulosic biomass by enzymes to permit useful products to be made more efficiently therefrom.

One aspect of the invention is a method of producing a product from lignocellulosic biomass comprising converting native cellulose $I_\beta$ to cellulose $III_I$ by pretreating the lignocellulosic biomass with liquid ammonia to generate a pretreated biomass, and producing a product therefrom. The liquid ammonia can be anhydrous ammonia. In other embodiments, the liquid ammonia is 80%-99% ammonia in a solvent. For example, the solvent can be water or an organic solvent. Examples of solvents that can be used include water, acetone, ethanol, methanol, isopropanol, dichloromethane, methyl acetate, ethyl acetate, chloroform and combinations thereof.

In further embodiments, the liquid ammonia is combined with acetone for pretreatment. As illustrated herein, acetone:ammonia leads to efficient formation of cellulose III from cellulose I. In some embodiments, the volume:volume ratio of liquid ammonia to acetone can range from 10:90 to 99:1.

The lignocellulosic biomass can be pretreated with liquid ammonia for about 1 minute to 3 hours. Temperatures useful for treatment of the lignocellulosic biomass with liquid ammonia (with or without solvent) include temperatures ranging from about 20° C. to about 140° C., or from about 4° C. to about 160° C. In some embodiments, other temperatures may be used.

The weight ratio of liquid ammonia to lignocellulosic biomass can be about 8:1 to 2:1.

In some embodiments, the pretreatment can also include extracting plant cell wall components such as lignin, hemicellulose, arabinan, and combinations and degradation products thereof. Such extraction can be performed simultaneously with anhydrous liquid ammonia pretreatment, or the extraction is performed after anhydrous liquid ammonia pretreatment. After the extraction the glucan and/or xylan are substantially retained with the pretreated biomass. The extracted lignin and/or hemicellulose can be converted to resins, polymers, biofuels, biochemicals, heat and/or electricity.

However, in some embodiments, the pretreatment of lignocellulosic biomass yields cellulose III that is readily digested and/or fermented even though plant cell wall components are not extracted.

After pretreatment the pretreated biomass can be digested with a combination of enzymes. For example, the combination enzymes can include at least one exocellulase and at least one endocellulase. Thus, the combination of enzymes can include Cel7A (Cellobiohydrolase I), Cel6A (Cellobiohydrolase II) and Cel7B (EG I), from *Trichoderma reesei*. The combination of enzymes can also include Cel5A_tr, from *Trichoderma reesei*, Cel5A_ac is from *Acidothermus cellullolyticum*, or a combination thereof. In some embodiments, the combination of enzymes can further include *Trichoderma reesei cellulase* Cel12A. Cel61A, Cel61B, or a combination thereof.

Moreover, as illustrated herein, significant glucan and xylan conversion to sugars and/or oligosaccharides is readily achieved despite a high ratio of pretreated biomass to total enzyme. For example, enzymatic hydrolysis of the pretreated biomass can proceed at a rate that is at least 1.5 times faster than biomass that has not been pretreated with the liquid ammonia pretreatment procedures described herein.

In some embodiments, the ammonia and/or the solvent used for pretreatment is recycled. In other embodiments, the liquid ammonia and/or the solvent is re-used to pretreat another batch of lignocellulosic biomass. Such recycling and/or re-utilization of the liquid ammonia and/or solvent can be performed batchwise, or semi-batchwise or continuously.

The product ultimately generated after performing the pretreatment methods described herein can be a biofuel.

Other aspects and embodiments of the invention are further described below.

BRIEF DESCRIPTION OF THE FIGURES

FIGS. 3A and 3B provide (A) a scheme for converting cellulose I to other cellulose allomorphs using different chemicals and (B) powder X-ray diffraction spectra obtained for different cellulose allomorphs.

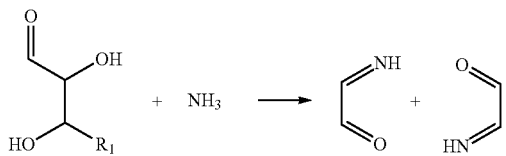

Figure 4A:
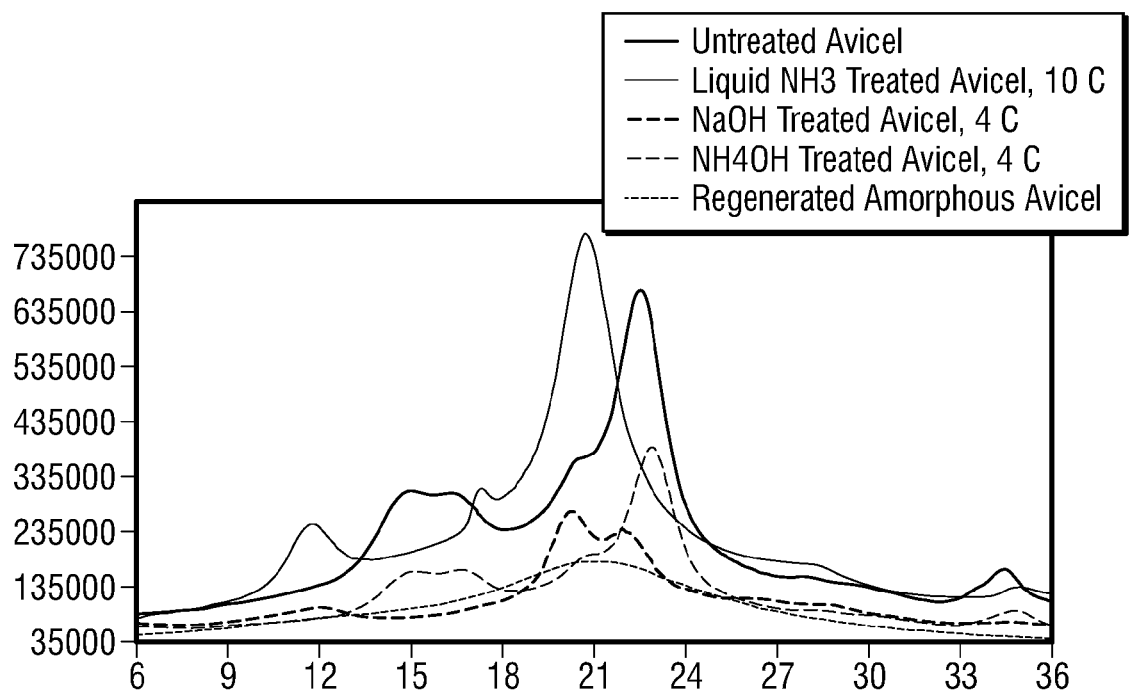
FIG. 4A shows powder X-ray diffraction spectra of cellulose (Cellulose I) treated with liquid ammonia (Cellulose III; 0.5 hr, 10° C., 7:1 ammonia to dry biomass loading, 0.05:1 water to dry biomass loading), sodium hydroxide (Cellulose II), 28% ammonium hydroxide (1 hr, 4 C, 10:1 liquid to dry biomass loading) and concentrated phosphoric acid (amorphous cellulose) in embodiments of the present invention. Avicel was the cellulosic substrate in all cases. Y-axis and X-axis depict intensity counts and two-theta angles, respectively.
Figure 4B:
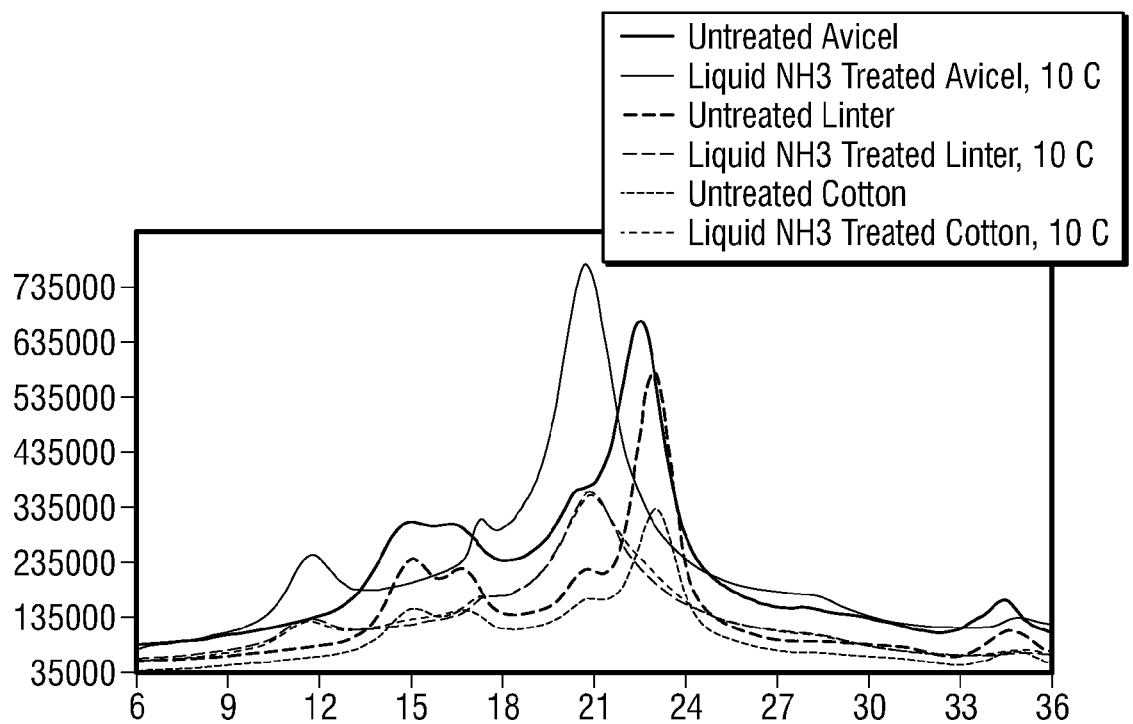
FIG. 4B shows powder X-ray diffraction spectra of untreated (Cellulose I) and liquid ammonia (Cellulose III; 0.5 hr, 10° C., 7:1 ammonia to dry biomass loading, 0.05:1 water to dry biomass loading) treated celluloses in embodiments of the present invention. Avicel, cotton linters and native cotton were the cellulosic substrates used. Y-axis and X-axis depict intensity counts and two-theta angles, respectively.
Figure 7:
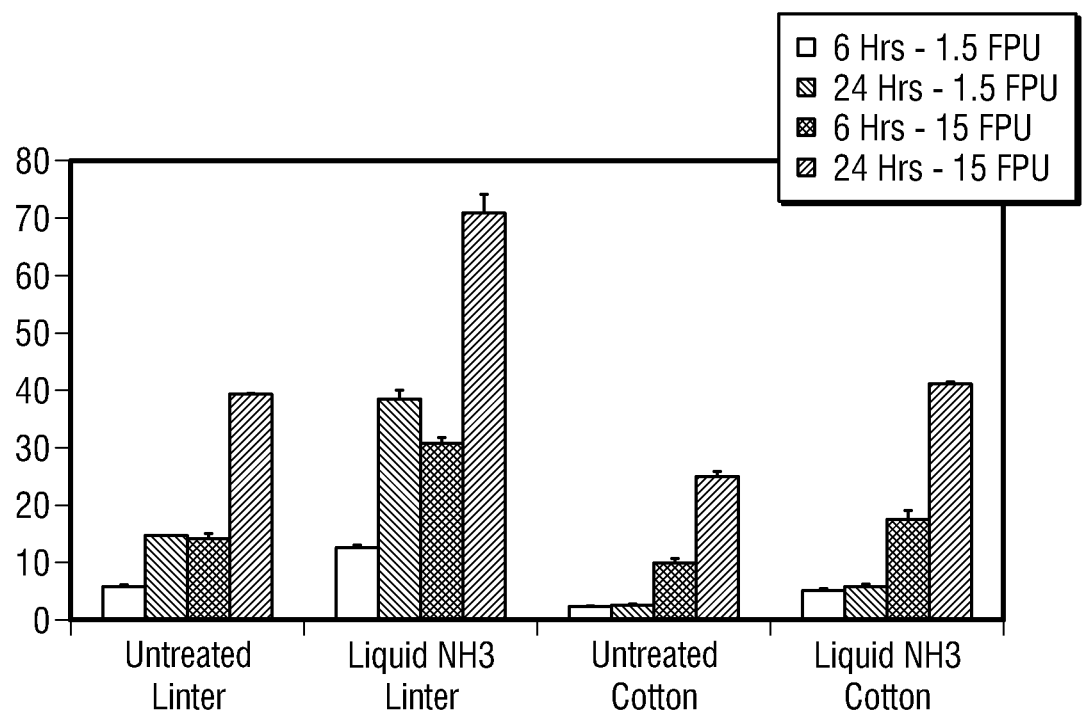

FIG. 7 shows enzymatic digestibility of untreated (Cellulose I) and liquid ammonia-treated (Cellulose III) celluloses in embodiments of the present invention (see FIG. 4B for details on sample preparation conditions). Cotton linters and native cotton fibers were the cellulosic substrates and the enzyme loading was 1.5 or 15 FPU/g glucan of Spezyme CP (supplemented with Novo 188). Y-axis depicts percent glucan conversion after 6 or 24 hours of hydrolysis.

Figure 8A:
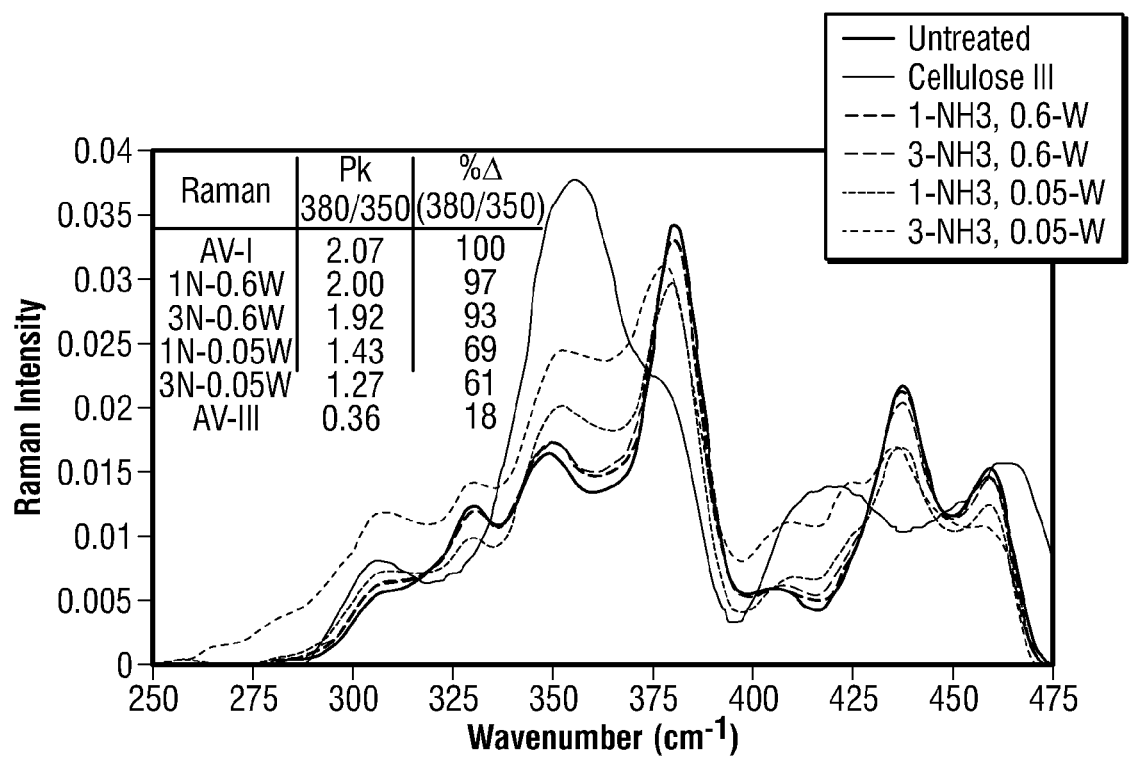

FIG. 8A illustrates the relative change in the amount of crystalline allomorphs present in Avicel (AV), with or without ammonia+water treatment (N=ammonia loading and W=water loading, per unit dry weight biomass) based on Raman spectral peak intensities (Iwavenumber) at respective wave numbers (e.g. 380 and 350; cm$^{-1}$). The pretreatment conditions are shown in the figure legend. The ratio of 380 and 350 cm$^{-1}$ Raman peak heights was used as a measure of the amount of cellulose I remaining in the sample after treatment, where $$Pk(380/350)=1-(I_{380}/I_{350}); \text{ and}$$

$$\% \Delta(380/350)_{unknown}=100*[Pk(380/350)]_{AV\text{-}unknown}/[Pk(380/350)]_{AV\text{-}1}.$$

Figure 8B:
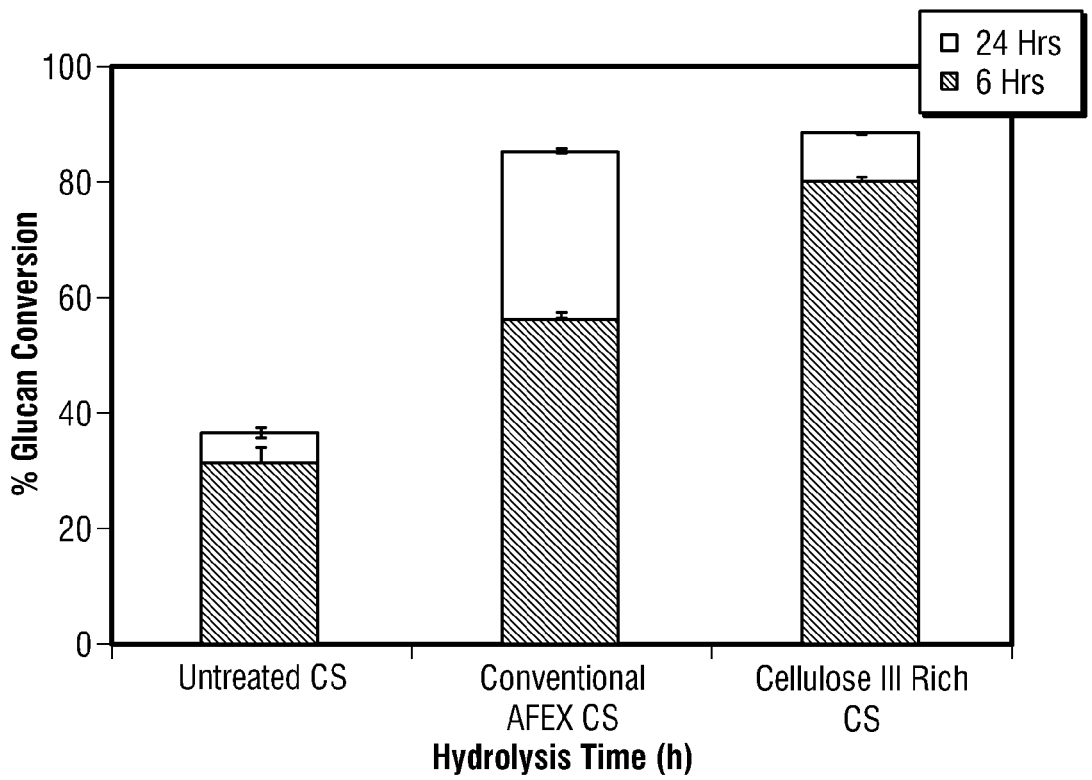

FIG. 8B illustrates the enzymatic digestibility (15 FPU Spezyme CP cellulase/g glucan) of untreated corn stover (CS), conventional AFEX treated CS (AFCS, formed at 130° C. for 15 min. using 1; 1 ammonia to dry biomass loading, 0.6:1 water to dry biomass loading) and liquid ammonia-treated corn stover (cellulose III rich). No cellulose III was formed during conventional AFEX. Cellulose III in ammonia-treated corn stover was produced by treating AFCS with anhydrous liquid ammonia (7:1 ammonia to dry biomass loading, 0.05:1 water to dry biomass loading) at 25° C. for 2 hrs.

Figure 9:
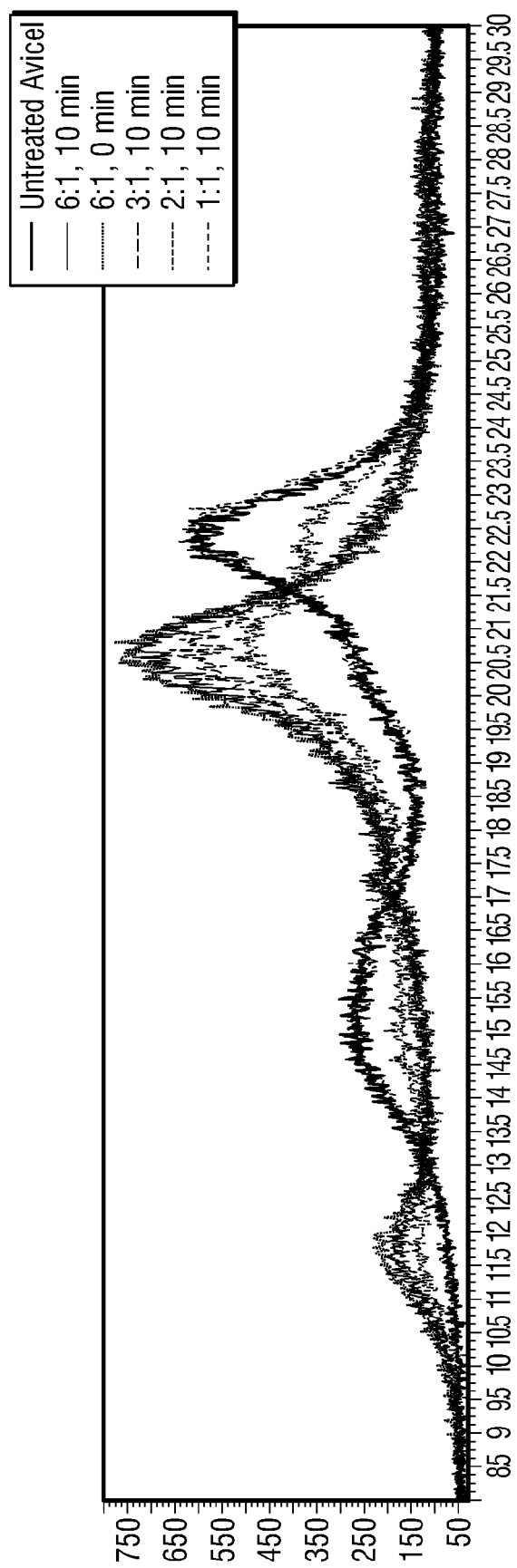

FIG. 9 illustrates the effect of the weight ratio of ammonia to dry biomass loading on cellulose III formation during liquid ammonia pretreatment as detected by X-ray diffraction. The weight ratios of ammonia to Avicel tested were: 6:1, 3:1, 2:1 and 1:1 ammonia:Avicel (wt:wt). Pretreatment was for 10 minutes, except for the 6:1 ammonia:Avicel 0 min. sample that was sampled immediately after contracting the sample with liquid ammonia. Untreated Avicel was a control.

Figure 10A:
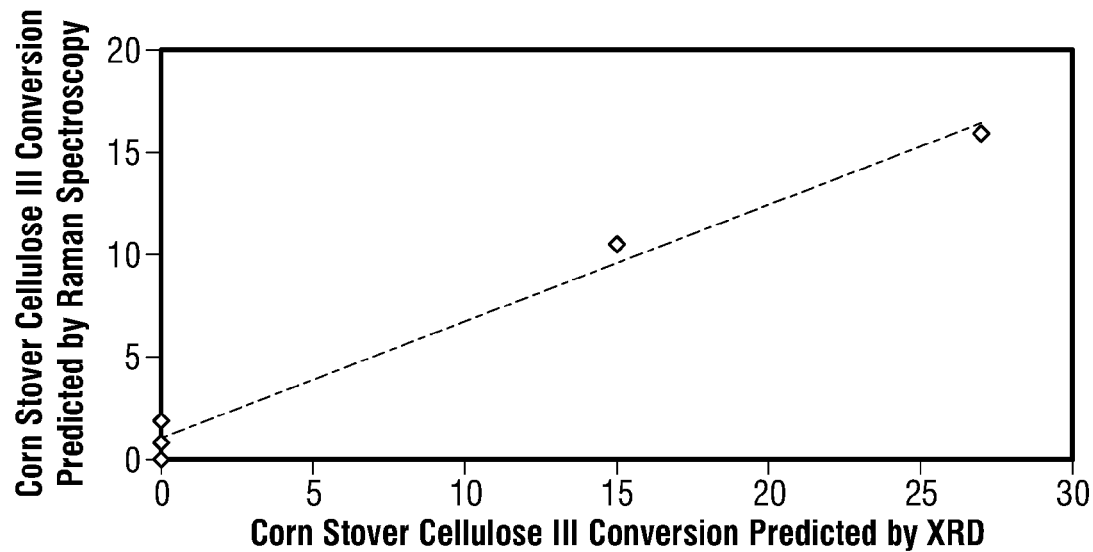

FIG. 10A shows a correlation of X-ray diffraction and Raman spectroscopy results for detecting cellulose III formation within corn stover during liquid ammonia-based pretreatment. Pretreatment conditions were identical to those described above for FIG. 8B for liquid ammonia-treated corn stover (cellulose III rich).

Figure 10B:
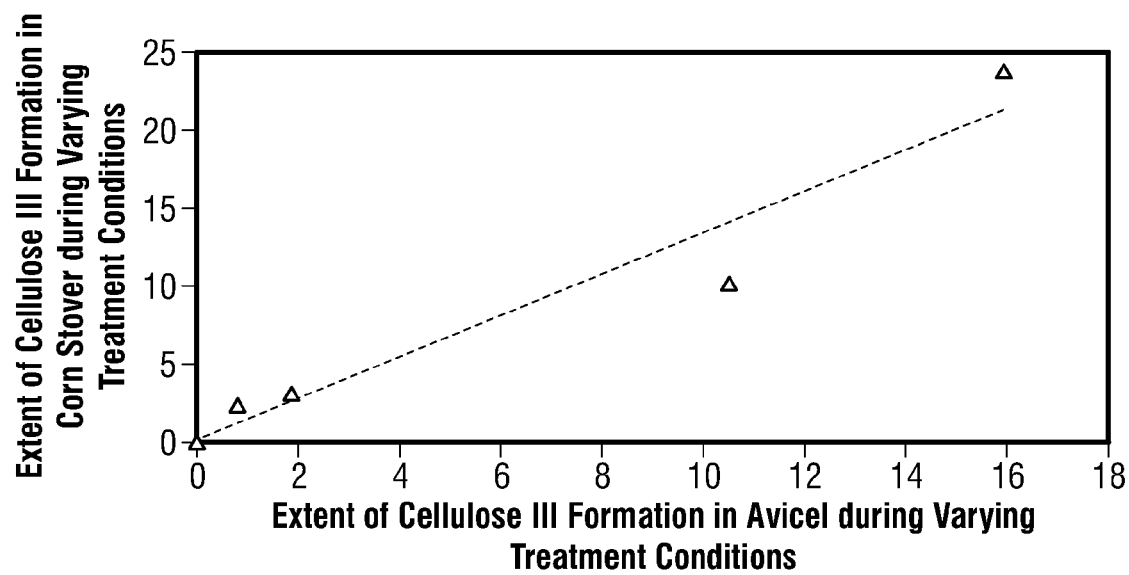

FIG. 10B shows a correlation between extent of cellulose III formation within corn stover and AVICEL for the same liquid ammonia pretreatment conditions used as in FIG. 10A, indicating that cellulose I can be converted to cellulose III in both of these substrates by using similar ammonia pretreatment conditions.

Figure 11:
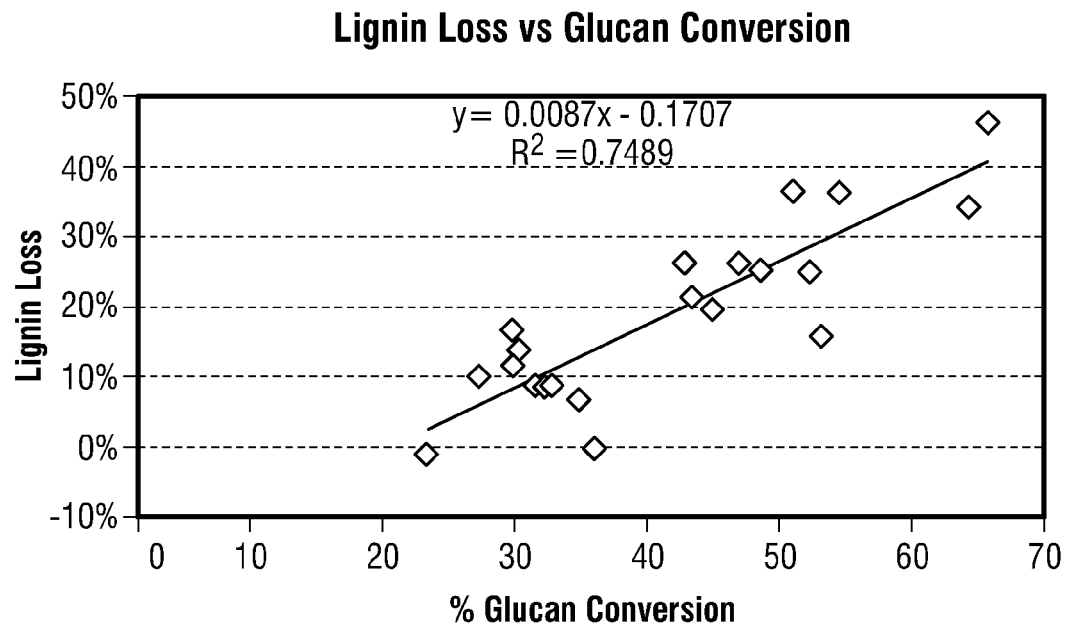

FIG. 11 graphically illustrates the correlation between Lignin Loss and % Glucan Conversion. In general, increased lignin removal correlated with increased glucan conversion. The lignin was removed from the biomass using an Extractive-Ammonia based process that allows production of cellulose III using liquid ammonia along with extraction of cell wall components.

Figure 12:
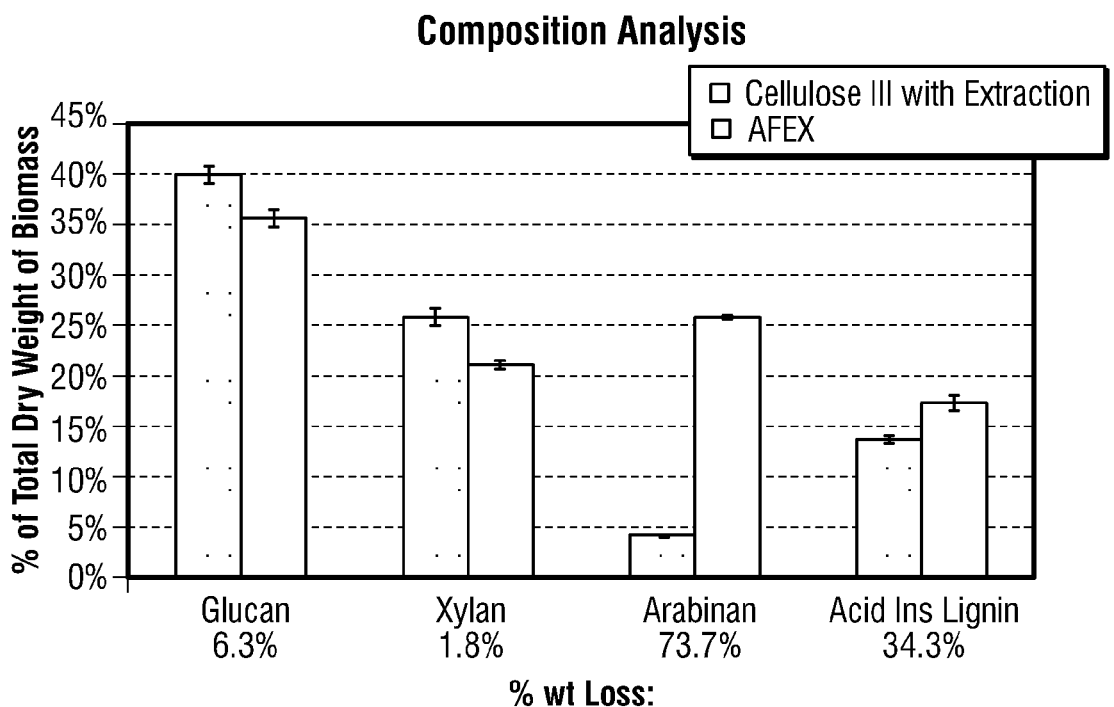

FIG. 12 shows the composition of corn stover after pretreatment by conventional AFEX or extractive-liquid ammonia pretreatment (see table 3 for details on pretreatment conditions). The percent weight of the various components extracted by the combination of the extractive procedure with liquid ammonia pretreatment with respect to untreated control is shown below the X-axis. Thus, the extractive-liquid ammonia pretreatment procedure extracted 73% of the Arabinan in the corn stover and 34.3% of the acid insoluble lignin (the acid soluble lignin extracted was not measured). However, the extractive-liquid ammonia pretreatment extracted only 6.3% glucan, leaving the remainder with the pre-treated biomass.

Figure 13:
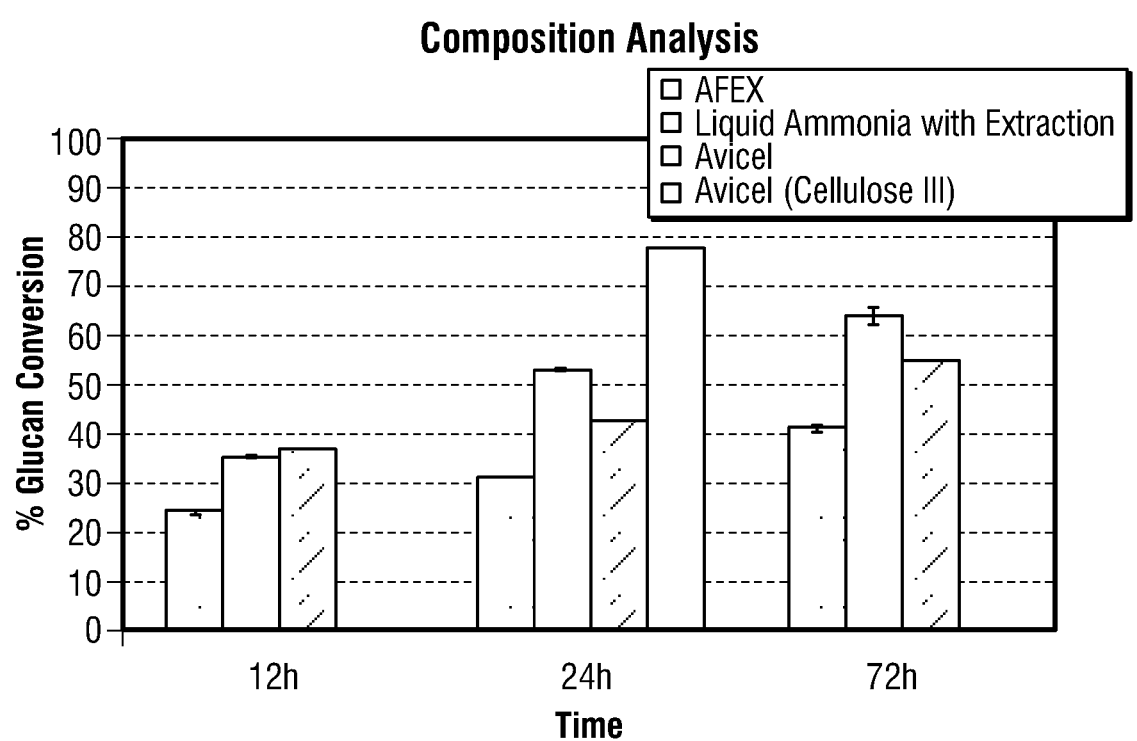
Figure 14A:
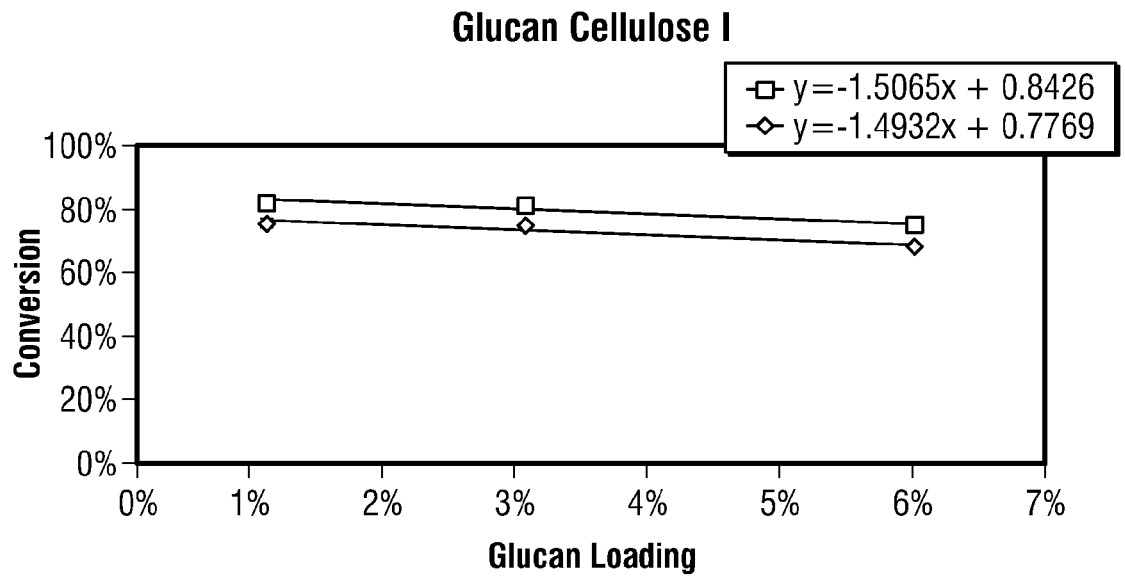
Figure 14B:
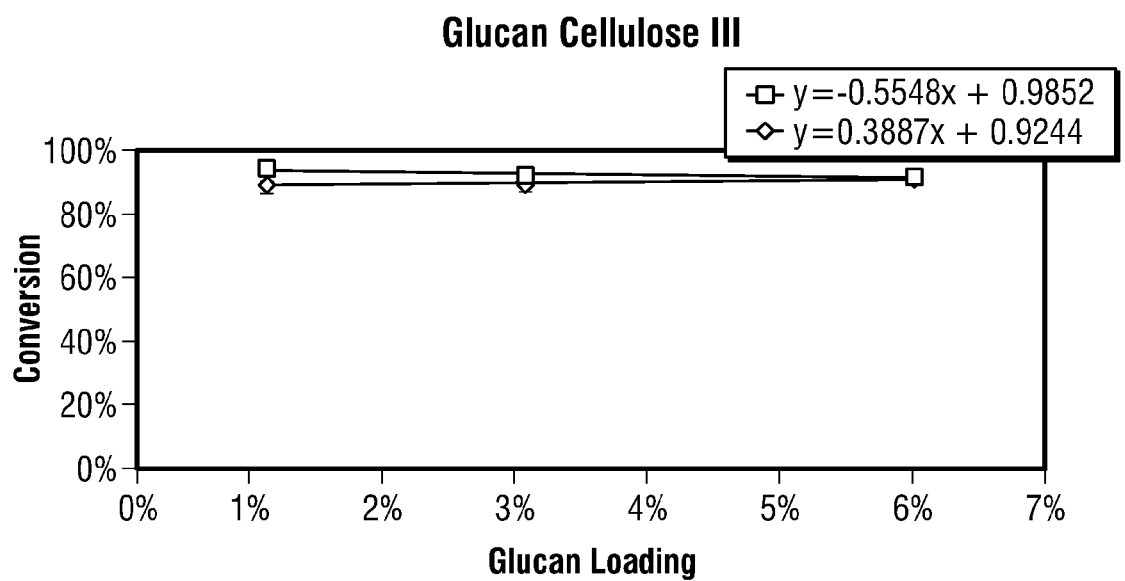
Figure 14C:
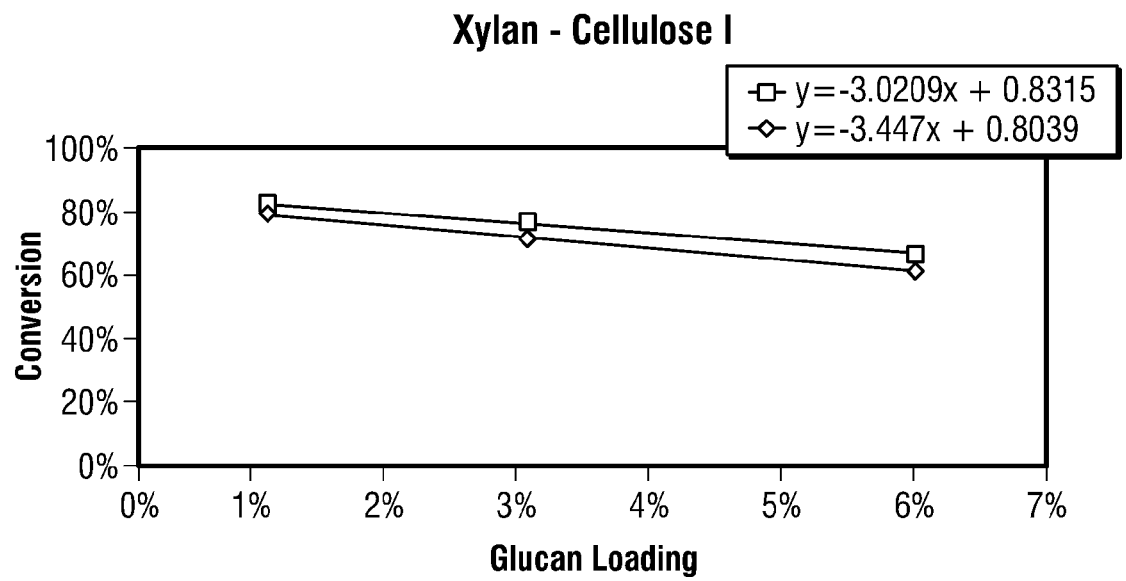
Figure 14D:
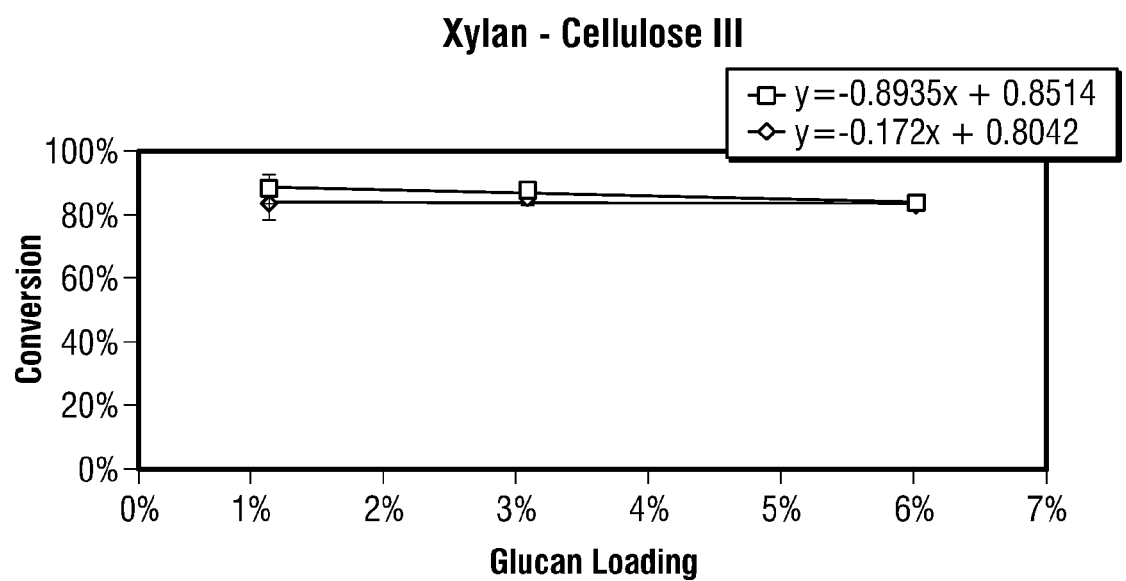

FIG. 13 graphically illustrates the % glucan conversion observed after enzyme digestion for 12, 24 and 72 hours for the following substrates: corn stover treated with conventional AFEX, corn stover treated with extractive liquid ammonia, untreated Avicel (cellulose I) and Avicel pretreated with liquid ammonia to generate cellulose III. The enzyme employed was 15 mg of Accelerase 1500 (Genencor-Danisco) cellulase per gram of glucan and the cellulosic substrates were incubated at 50° C. with stirring at 250 RPM for the indicated times.

FIG. 14A-D illustrate glucan and xylan conversion for cellulose I-rich (A,C) and cellulose III-rich (B, D) pretreated corn stover at high solids loading for low (15 mg/g glucan) and high (30 mg/g glucan) cellulase loading after 168 h hydrolysis. Cellulose I-rich pretreated corn stover was obtained after conventional AFEX pretreatment (130° C., 1:1 ammonia to dry biomass loading, 0.6:1 water to dry biomass loading, 15 min reaction time). Cellulose III-rich pretreated corn stover was obtained after liquid ammonia pretreatment (100° C., 7:1 ammonia to dry biomass loading, 0.05:1 water to dry biomass loading, 2 hr reaction time) with no extraction.

Figure 15:
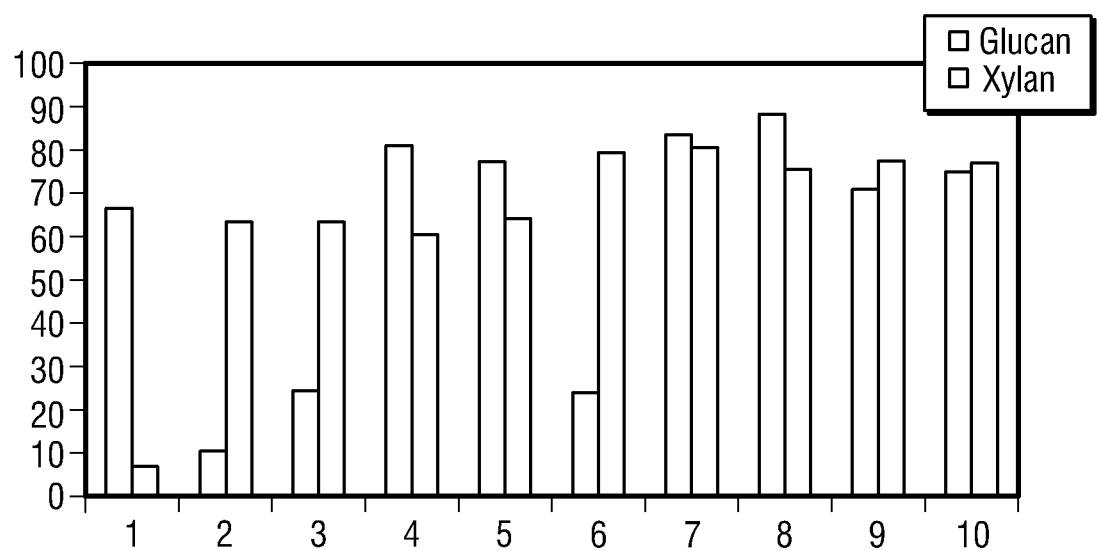
Figure 16A:
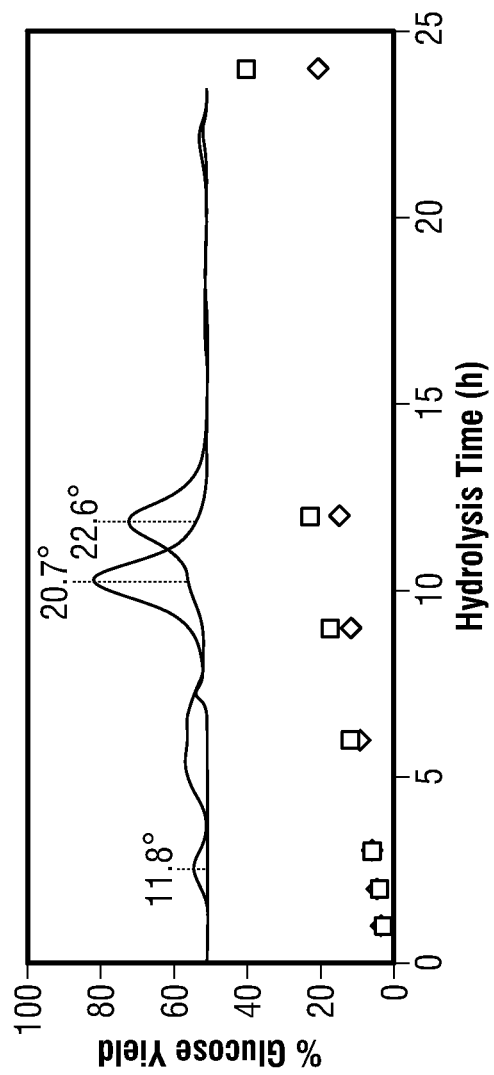
Figure 16B:
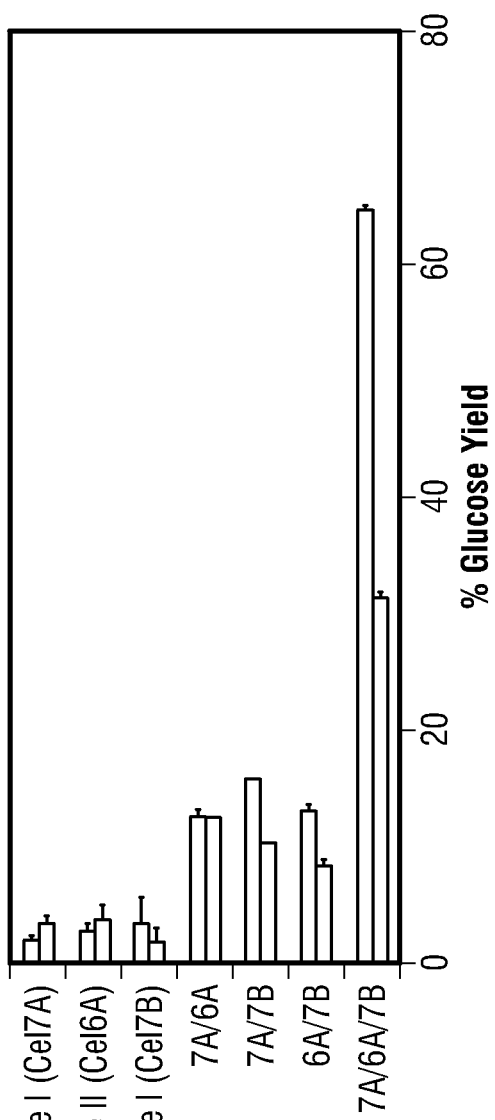
Figure 16C:
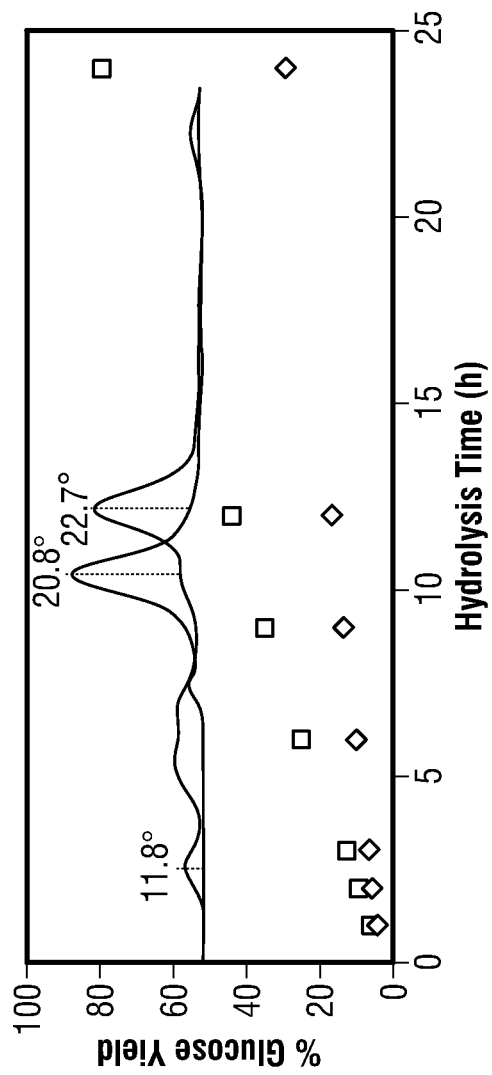
Figure 16D:
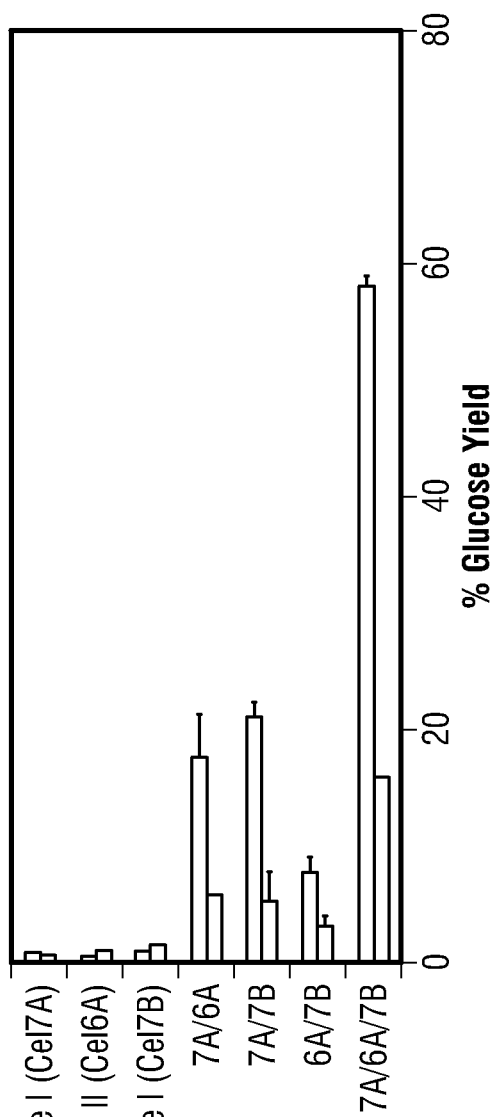
Figure 16E:
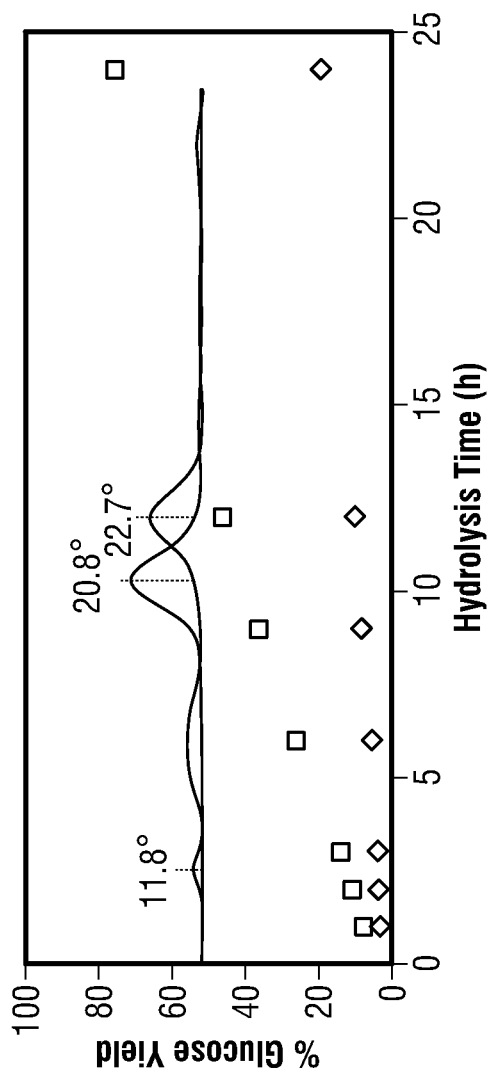
Figure 16F:
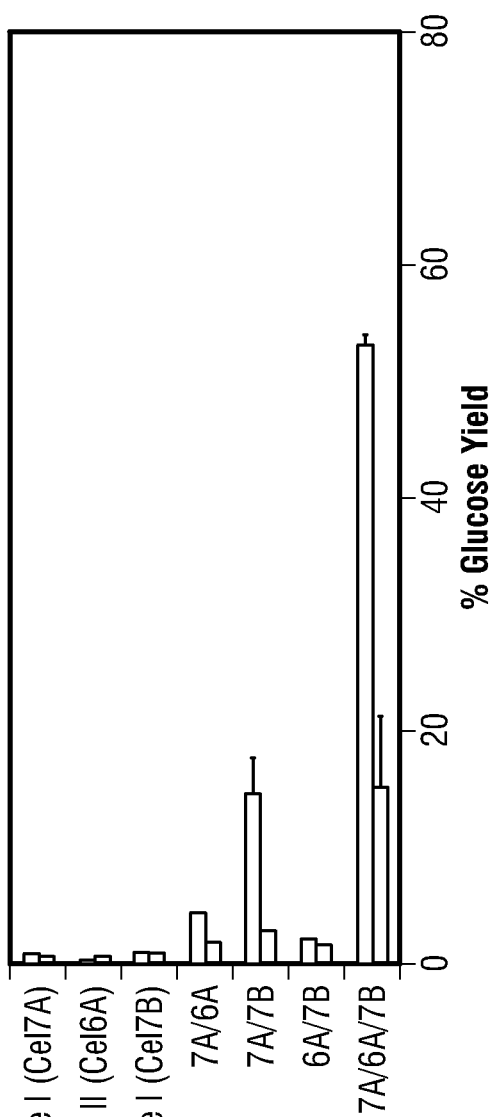

FIG. 15 illustrates the effect of mixing enzymes to achieve optimal digestion of non-extracted corn stover that was pretreated with liquid ammonia (100° C., 7:1 ammonia to dry biomass loading, 0.05:1 water to dry biomass loading, 2 hr reaction time) to generate cellulose III. The digestion of both glucan and xylan was observed. The total amount of enzyme employed was 30 mg and the digestion was allowed to proceed for 24 hrs. The mixtures are identified by the numbers along the x-axis. Enzymes 1, 2 and 3 were Accellerase 1500 (A), Multifect xylanase (X) and Multifect pectinase (P), respectively. Enzyme Mixtures 4, 5 and 6 were 50% A and 50% X, 50% A and 50% P, and 50% P and 50% X, respectively. Mixture 7 has equal amounts of A, X and P. Mixtures 8, 9 and 10 have 67% A-16% X-17% P, 67% X-16% A-17% P and 67% P-16% A-17% X, respectively.

FIG. 16A-F illustrate the enzymatic digestibility of cellulose as a function of its crystalline state and the cellulases employed. The hydrolysis time course is shown for cellulose I (diamond symbols) and III (square symbols) derived from Avicel (A), Cotton Linters (C) and Cotton Fibers (E). The X-ray diffraction spectra for respective substrates is shown above the graph of percent glucose yield vs. time. Avicel was hydrolyzed by 1.5 FPU Spezyme CP cellulase/g glucan, while the cotton derived substrates were hydrolyzed by 15 FPU Spezyme CP cellulase/g glucan. The enzymatic digestibility is shown for cellulose I (open bars) and III (shaded bars) derived from Avicel (B), Cotton Linters (D) and Cotton Fibers (F) for various combinations of *Trichoderma reesei* exocellulases (Cel7A, Cel6A) and endocellulases (Cel7B, Cel5A). Equivalent enzyme loadings added for each assay were 2.5 mg of each cellulase/g Avicel or 10 mg of each cellulase/g cotton derived substrates. In addition, 10% beta-glucosidase of total cellulase was added to each assay mixture to prevent cellobiose build-up. In all cases, cellulose III was prepared at 95 C, 7:1 ammonia to dry biomass loading, 0.05:1 water to dry biomass loading, with 30 min reaction time.

Figure 17:
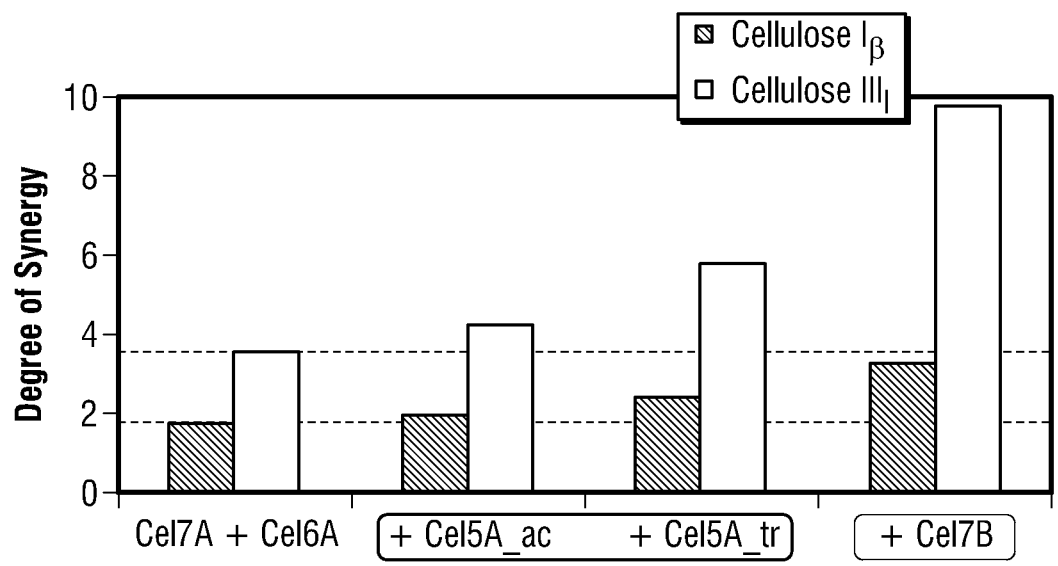

FIG. 17 illustrates that endocellulases increase the degree of synergistic effect (DSE) over that observed for exocellulases (Cel7A+Cel6A) during hydrolysis of crystalline cellulose I (shaded bars) and III (open bars). Endonucleases Cel7B or Cel5A_tr (both from *Trichoderma reesei*) or Cel5A_ac (from *Acidothermus cellulolyticum*) were combined with exocellulases Cel7A+Cel6A as indicated along the x-axis of the graph. The substrates tested were cellulose I and cellulose III derived from Avicel. The substrates were incubated with 2.5 mg of the indicated purified enzymes. Beta-glucosidase (10% of total cellulase added) was added to each assay to prevent inhibition by cellobiose. The y-axis shows the degree of synergy for the different combinations of enzymes, where a larger value indicates increased synergistic digestion of the substrate.

Figure 18:
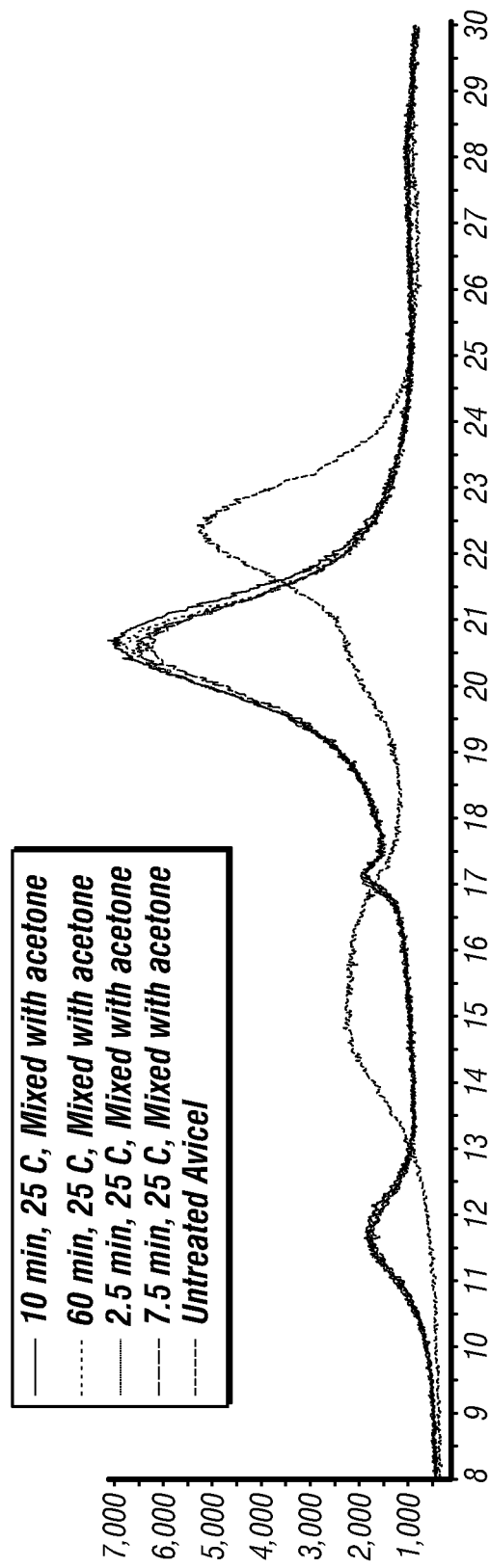
Figure 19A:
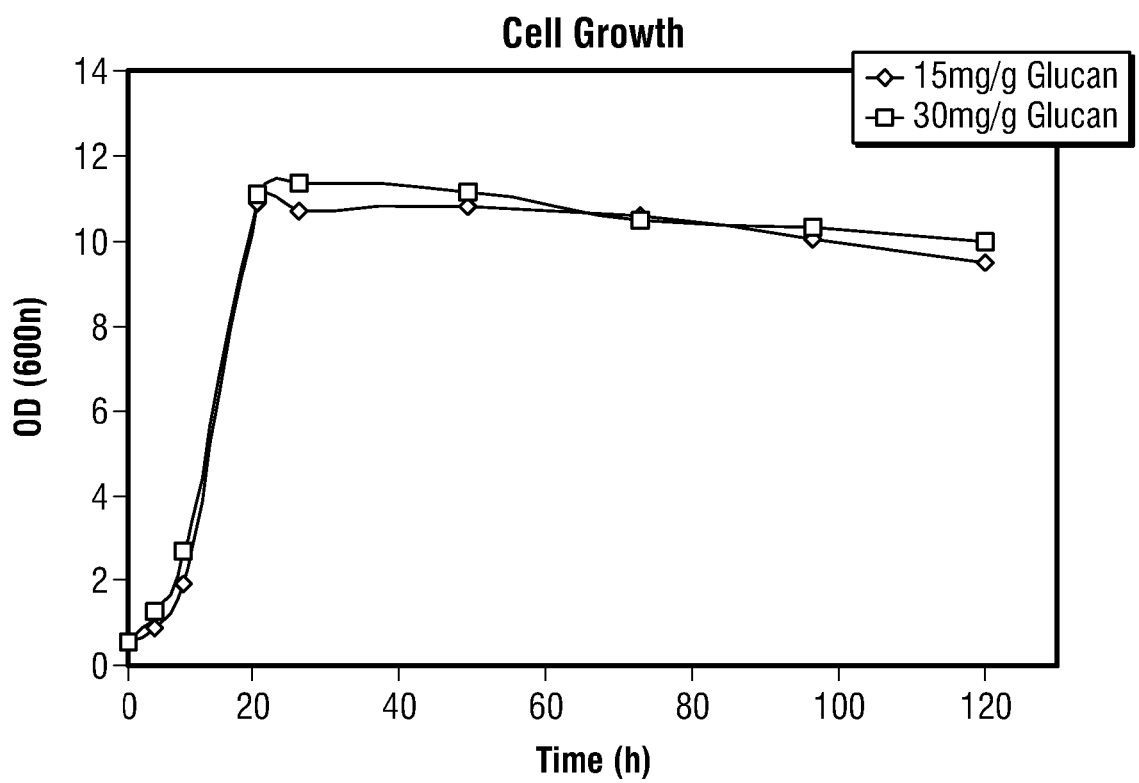
Figure 19B:
Figure 19C:
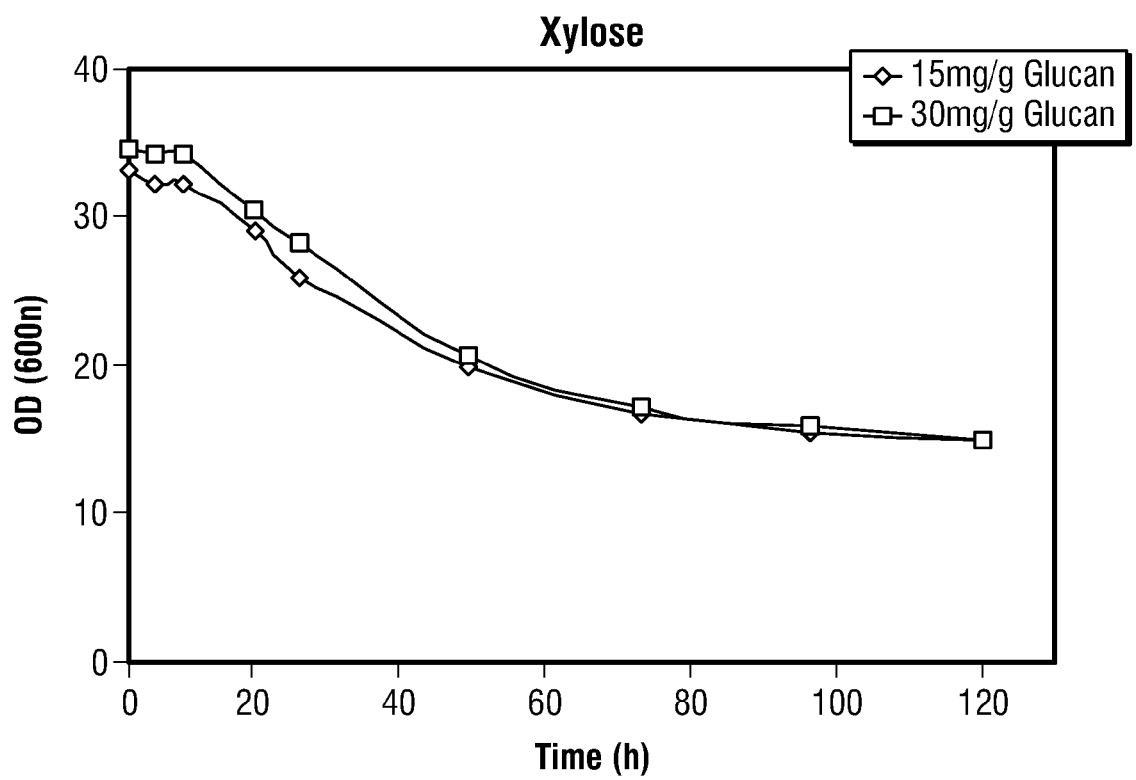
Figure 19D:
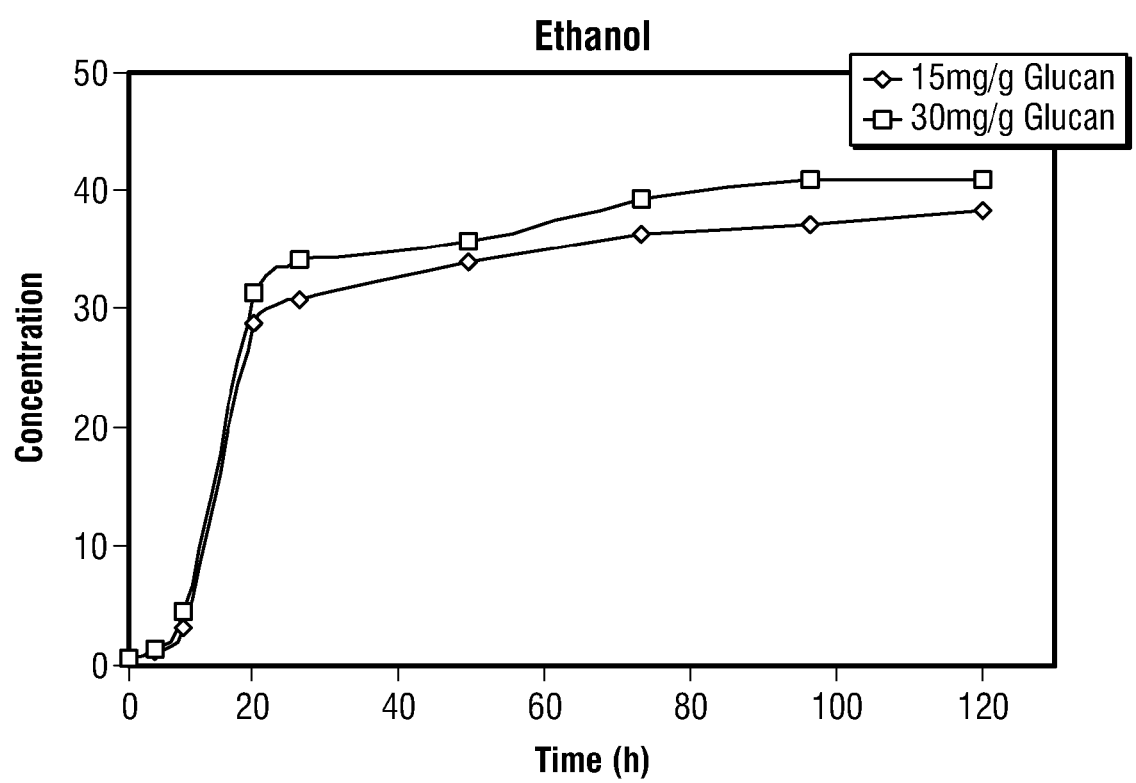

FIG. 18 shows that adding acetone as a co-solvent during liquid ammonia pretreatment leads to efficient conversion of cellulose I to cellulose III. Avicel was treated with liquid ammonia containing acetone at 25° C. for different times (2.5, 7.5, 10 and 60 min.). As illustrated, substantially all of the cellulose I was converted to cellulose III within 2.5 min. of incubation in the liquid ammonia/acetone mixture.

FIG. 19A-D show the microbial fermentability of cellulose III-rich pretreated corn stover 6% glucan loading hydrolyzate (see FIG. 14 for details on how this hydrolyzate was prepared) that was obtained after liquid ammonia pretreatment (100° C., 7:1 ammonia to dry biomass loading, 0.05:1 water to dry biomass loading, 2 hr reaction time) with no extraction. The engineered yeast (*Saccharomyces cerevisiae* 424A) was able to grow to high cell densities (FIG. 19A) and readily ferment the glucose (FIG. 19B) and xylose (FIG. 19C) in the hydrolyzate to produce at least 40 g/L ethanol (FIG. 19D) in the given period of fermentation without addition of any exogenous nutrients or pretreated biomass detoxification.

DETAILED DESCRIPTION OF THE EMBODIMENTS

The invention generally relates to pretreatment of lignocellulosic biomass to generate a pretreated biomass that is more readily digested to useful sugars, disaccharides and oligosaccharides. As is known to one of skill in the art, processes of releasing useful products from lignocellulosic biomass are more complicated and typically involve more steps than processes for releasing products from substantially pure cellulose.

In the following detailed description of the preferred embodiments, reference is made to the accompanying drawings, which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that chemical, procedural and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

DEFINITIONS

The term "Ammonia Fiber Explosion" or "Ammonia Fiber Expansion" (hereinafter "AFEX") pretreatment as used herein, refers to a process for pretreating biomass with ammonium hydroxide to solubilize lignin/hemicellulose and redeposit it from in between plant cell walls to the outer plant cell wall surfaces of the biomass. AFEX typically involves treatment of biomass with ammonium hydroxide and the ammonium hydroxide concentrations commonly used during conventional AFEX range between 55-65%. Conventional AFEX conditions also typically involve about 1:1 ammonium hydroxide to biomass loading, 0.6:1 water to biomass, 130° C., and 15 minutes reaction time. Due to the addition of significant amounts of water in the conventional AFEX process, the cellulose III crystalline state is not produced from the native cellulose I crystalline state. However, an AFEX pretreatment disrupts the lignocellulosic matrix, thus modifying the structure of lignin, partially hydrolyzing hemicellulose, and increasing the accessibility of cellulose and the remaining hemicellulose to subsequent enzymatic degradation. Lignin is the primary impediment to enzymatic hydrolysis of native biomass, and removal or transformation of lignin is a suspected mechanism of several of the leading pretreatment technologies, including AFEX. However in contrast to many other pretreatments, the lower temperatures and non-acidic conditions of the AFEX process prevent lignin and/or hemicellulose from being converted into furfural, hydroxymethyl furfural, phenolics and organic acids that could negatively affect enzyme/microbial activity. The process further expands and swells cellulose fibers and further breaks up amorphous hemicellulose in lignocellulosic biomass. These structural changes open up the plant cell wall structure enabling more efficient and complete conversion of lignocellulosic biomass to value-added products while preserving the nutrient value and composition of the material. See, for example, the methods described in U.S. Pat. Nos. 6,106,888, 7,187,176, 5,037,663, and 4,600,590, all of which are hereby incorporated by reference in their entirety as if fully set forth herein.

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "lignocellulosic biomass" or "cellulosic biomass" as used herein, is intended to refer to virtually any plant-derived organic matter (woody or non-woody) available for energy on a sustainable basis. Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally grass crops, such as various prairie grasses, including prairie cord grass, switchgrass, miscanthus, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States.

The term "biofuel" as used herein, refers to any renewable solid, liquid or gaseous fuel produced biologically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops (e.g., grains, such as corn), crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

Cellulose is a polysaccharide with the formula $(C_6H_{10}O_5)_n$, where n is an integer of from 100-200,000. Thus, in general, cellulose consist of a linear chain of several hundred to over ten thousand $\beta(1\rightarrow4)$ linked D-glucose units. The $\beta(1\rightarrow4)$ linkage is distinct from the $\alpha(1\rightarrow4)$-glycosidic bonds present in starch, glycogen, and other carbohydrates. Unlike starch, cellulose is a straight chain polymer without coiling and branching. Instead, cellulose has an extended and substantially stiff rod-like conformation, where hydroxyl groups on the glucose from one chain form hydrogen bonds with oxygen molecules on the same or on a neighbor chains, holding the chains firmly together side-by-side and forming microfibrils.

There are several different crystalline structures of cellulose, which typically correspond to the location of hydrogen bonds between and within strands. Natural cellulose is cellulose I, with structures $I_\alpha$ and $I_\beta$. Cellulose produced by bacteria and algae is enriched in $I_\alpha$ ($I_{alpha}$) while cellulose of higher plants consists mainly of $I_\beta$ ($I_{beta}$). Cellulose I is irreversibly converted to cellulose II by treatment with aqueous NaOH. Cellulose $III_I$ can be generated from cellulose I by treatment with ammonia (e.g., using methods described herein), while cellulose $III_{II}$ is generated from cellulose II. As referred to herein cellulose III is cellulose $III_I$. Cellulose IV is generally made by heating cellulose III in and appropriate solvent (e.g., glycerol). The X-ray diffraction 2θ angles for the different crystalline structures of cellulose are shown below in Table 1.

TABLE 1

| | | | |
|---|---|---|---|
| Cellulose I | 14.6 | 16.4 | 22.6 |
| Cellulose III | 11.7 | | 20.6 |
| Cellulose IV | 15.5 | | 22.4 |

The term "moisture content" as used herein, refers to percent moisture of biomass (e.g., the lignocellulosic biomass). The moisture content is calculated as grams of water per gram of wet biomass (biomass dry matter plus water) times 100%. In some embodiments, the biomass (lignocellulosic biomass) has a moisture content of about 1% to about 25%. In other embodiments, the biomass (lignocellulosic biomass) has a moisture content of about 5% to about 20%. In further embodiments, the biomass (lignocellulosic biomass) has a moisture content of about 10% to about 20%. In still further embodiments, the biomass (lignocellulosic biomass) has a moisture content of about 15% to about 20%.

The term "pretreatment step" as used herein, refers to any step intended to alter native biomass so it can be more efficiently and economically converted to reactive intermediate chemical compounds such as sugars, organic acids, etc., which can then be further processed to a variety of value added products such a value-added chemical, such as ethanol. Pretreatment can influence the degree of crystallinity of a polymeric substrate, reduce the interference of lignin with biomass conversion and prehydrolyze some of the structural carbohydrates, thus increasing their enzymatic digestibility and accelerating the degradation of biomass to useful products. Pretreatment methods can utilize acids of varying concentrations (including sulfuric acids, hydrochloric acids, organic acids, etc.) and/or other components such as ammonia, ammonium hydroxide, lime, and the like. Pretreatment methods can additionally or alternatively utilize hydrothermal treatments including water, heat, steam or pressurized steam. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugar monomers or oligomers. A unique pretreatment step or process involving use of liquid ammonia and/or extraction of plant wall components is described in more detail herein.

Cellulose Structures

Cellulose exists in various polymorphic states ($I_\beta$, II, III, and IV). Cellulose allomorphs are composed of layered sheets which contain intra-chain and inter-chain hydrogen bonding and, in some cases; these sheets may interact via hydrogen bonding (Davis et al., in *Agricultural Biomass, Biobased Products, and Biofuels*. Chicago, Ill. (2007)). Some of the cellulose allomorphs (I and its inter-convertible relative $I_{V1}$) lack inter-sheet hydrogen bonds and are thought to display parallel sheet packing, while the others (I, II and III) contain inter-sheet hydrogen bonds. Crystal chain packing is thought to play an important role in the kinetics of enzymatic hydrolysis. The relative rates of digestion of the different cellulose allomorphs digested using ruminal bacteria were found to vary in the following order: amorphous>$III_I$>$IV_I$>$III_{II}$>I>II. For example, in one study, cellobiose production from cellulose $III_1$ was five times higher than that produced from cellulose I when the enzyme cellobiohydrolase I (Cel7A) was used (Igarashi et al., FEBS Journal 274 (7): 1785-1792 (2007)). When produced using certain conditions, cellulose III can also be converted back to cellulose I either by reaction with glycerol or water at high temperatures.

The different allomorphs of cellulose can be prepared using a variety of methods, and the allomorphs can be distinguished based on their X-ray profile or by use of Raman spectroscopy. FIG. 3A shows one scheme for converting cellulose I to other allomorphs using different chemicals. FIG. 3B shows powder X-ray diffraction spectra of different cellulose allomorphs. See also, Weimer et al., Appl Environ Microbiol. 57(11):3101-3106 (1991).

Treatment of cellulose I with concentrated phosphoric acid (>81% w/w; 4°, 1 hr) results in complete dissolution of the solid, which was recovered as a fluffy, low-density solid by addition of excess water to the solution (Zhang et al., *Biotechnology and Bioengineering* 97(2), 214-223 (2007); Zhang et al. *Biomacromolecules* 7(2), 644-648 (2006); Swatloski et al., *Journal of the American Chemical Society* 124 (18), 4974-4975 (2002)). Dissolution of cellulose in phosphoric acid has been known to completely disrupt the super-molecular architecture of the cellulose structure, resulting in its transformation from the crystalline to amorphous state with no change in the degree of polymerization. The X-ray diffraction pattern for the regenerated amorphous cellulose depicts a relatively flat spectrum with no distinct peaks indicating a nearly complete loss of crystallinity.

AVICEL (97-99% glucan content) can be treated with different chemicals to obtain various cellulose polymorphs to compare their X-ray diffraction patterns (FIG. 3B) and enzymatic digestibility under comparable enzyme loadings. AVICEL treated with sodium hydroxide (25%, w/w) at 4° C. for 1 hour gives rise to the distinct cellulose II pattern, with a relative decrease in the X-ray diffraction peak at 22 degree two-theta (2θ) accompanied by an increase the peaks at 20 and 12 degrees 2θ.

Treatment of cellulose I (AVICEL) with ammonium hydroxide (28-30%, w/w) at 4° C. for 1 hour resulted in no significant modification of the crystal structure. This result is not entirely surprising, because sodium hydroxide is a stronger base and it required concentrations greater than 10-15% to disrupt the hydrogen bonding network in native cellulose I and generate cellulose II.

Cellulose III formation can be detected from its distinct X-ray diffraction pattern by disappearance of the peak at 22 degree 2θ accompanied by formation of a prominent peak at 20 and 12 degrees 2θ. Such an X-ray diffraction pattern is comparable to what has been reported in literature for cellulose III from cotton. Treatment of cellulose III with ammonium hydroxide (of varying concentrations) has also been reported to cause reversion to cellulose I.

One aspect of this application is to describe the effect of cellulose crystal structure on cellulase digestibility. Various cellulosic substrates (e.g. AVICEL, linters, cotton, and corn stover) were employed in these studies. In one embodiment, native cellulose $I_\beta$ can be transformed to cellulose $III_I$ by treating the substrates with anhydrous liquid ammonia or solutions that contains 80% or more ammonia. Contrary to certain reports, there is substantially no formation of cellulose III upon treatment of cellulose $I_\beta$ with ammonium hydroxide. In fact, the presence of substantial amounts of water during treatment of cellulose $I_\beta$ with ammonia by conventional procedures substantially inhibits formation of cellulose III.

Pretreatment with Liquid Ammonia

One aspect of the invention is a method of producing a product from lignocellulosic biomass comprising converting native cellulose $I_\beta$ to the highly digestible cellulose III allomorph by treating the lignocellulosic biomass with liquid ammonia. The liquid ammonia can be anhydrous ammonia or a solution of 80%-99% ammonia in a solvent. In general, the pretreatment conditions described herein are of reduced severity (temperature, pressure, residence time and chemical loading per amount of biomass) and therefore improve the economic viability of the biorefinery. In one embodiment, the methods also involve extracting plant wall component, such as lignin from the lignocellulosic biomass, which can be done during or after pretreatment.

The methods described herein generally permit reduction of the enzyme loading per weight of biomass, which can further improve the economic viability of the biorefinery. Pretreatment and enzymes together generally constitute approximately 27% of the total operating cost in a conventional biorefinery, which is typically considered to be the second most important factor after the feedstock cost (33%). It is desirable to reduce the cost of biomass deconstruction into fermentable sugars in order to improve the economic viability of the biorefinery process.

The effect of pretreatment parameters (ammonia/water loading, residence time, temperature) on the conversion of cellulose I to III was quantified by X-ray diffraction and Raman spectroscopy studies. The degree to which glucans within a pretreated cellulose sample become accessible to enzymatic hydrolysis was also assessed by digestion of the samples with selected enzymes. As described herein, certain enzyme combinations are particularly effective for digestion of pretreated celluloses, while other combinations are less effective.

The differential enzyme hydrolysis kinetics for cellulose depended on its crystalline form, where the order of the most easily digested to least easily digested forms of cellulose are: Amorphous cellulose>Cellulose III$_I$>Cellulose II>Cellulose I. The rate of enzymatic hydrolysis of cellulose III$_I$ was at least two fold greater than of native cellulose I. As described herein, significant improvement in hydrolysis rate for cellulose III is achievable by use of endoglucanases. Moreover, optimal rates of hydrolysis are obtained by using combinations of selected exocellulases and endocellulases. Differences in glucan chain packing (via modification of hydrogen bonding and hydrophobic interactions) for cellulose III versus native cellulose are likely responsible for the substantial increase in the hydrolysis rate.

Complete disruption of intermolecular hydrogen bonds within crystalline cellulose, using either concentrated acids or ionic liquids to solvate cellulose followed by its precipitation with water, produces mostly amorphous cellulose. Such treatment can help enhance the enzymatic hydrolytic rate. There are currently no studies that explain why complete disruption of the cellulose intrasheet and intersheet hydrogen bonding network enhances cellulase activity. However, even though amorphous cellulose is generally more easily digested, industrial-scale production of amorphous cellulose within a cellulosic biorefinery is energetically expensive and environmentally unsustainable. Therefore, processes for generating useful sugars and glucans from other forms of cellulose are the focus of this application.

The methods described herein allow the hydrogen bonding network of cellulose to be altered from its naturally occurring crystalline form, called cellulose I, to an activated form called cellulose III, which is more easily digested than cellulose I. Such conversion of cellulose I to cellulose III is efficiently performed by reacting cellulose I with anhydrous liquid ammonia or solutions that contains 80% or more ammonia. The interaction between liquid ammonia and cellulose I crystals leads to a change in the pattern of intra-chain and intra-sheet hydrogen bonding and to the formation of new inter-sheet hydrogen bonds. In the conversion from cellulose I to III, ammonia molecules penetrate the cellulose I crystal and form a crystalline complex called ammonia-cellulose I where each ammonia molecule sits in a distorted box defined by the edges of four neighboring glucan chains. X-ray and neutron diffraction studies have shown that ammonia molecules within the crystal interact with the neighboring chains via multiple hydrogen bonds. Following ammonia evaporation, cellulose does not revert to its initial crystal form (cellulose I) but adopts the new cellulose III form. FIGS. 3 and 4 show that the X-ray diffraction spectra of cellulose I and cellulose III differ. The inventors have found that this subtle structural alteration within the cellulose III hydrogen bond network enhanced its overall enzymatic hydrolysis yield by up to fivefold compared to native cellulose I.

Moreover, because reduced amounts of water are used, the cost for ammonia recovery from aqueous ammonia-water streams is reduced.

The effect of conventional AFEX (Ammonia Fiber Expansion) pretreatment parameters on the extent of formation of cellulose III, derived from Avicel, was studied using Raman spectroscopy. The extent of cellulose I to III transformation was estimated by the relative intensity of Raman peaks at 380 and 350 cm$^{-1}$, with respect to a 100% cellulose III standard sample that exhibited an 82% decrease in the peak ratio relative to cellulose I. When cellulose I was subjected to conventional AFEX in the presence of water (16% or more water in NH$_4$OH), there was only a marginal decrease in the ratio (3-6%). However, when cellulose I was treated with ammonia with substantially no added water (<5% water in the ammonia) there was a 31-39% decrease in ratio, indicating that a significant transformation of cellulose I had taken place to form cellulose III.

The results obtained indicate that it is feasible to simultaneously improve cellulose accessibility (via removal of lignin-hemicellulose that encrusts the cellulose fibrils) and alter cellulose crystal structure from cellulose I to cellulose III by adjusting the pretreatment conditions. In general, use of anhydrous liquid ammonia or solutions that contain 80%-85% or more ammonia allows complete transformation of cellulose I to III. The absence of significant water can also prevent reversion of cellulose III back to cellulose I. Previously, 40-100% reversion of cellulose III to cellulose I was seen in the presence of water and/or excessive heating (Lewin & Roldan, J. Polym. Sci. Part C-Polym. Sympos. 36: 213-229 (1971)).

Figure 6:
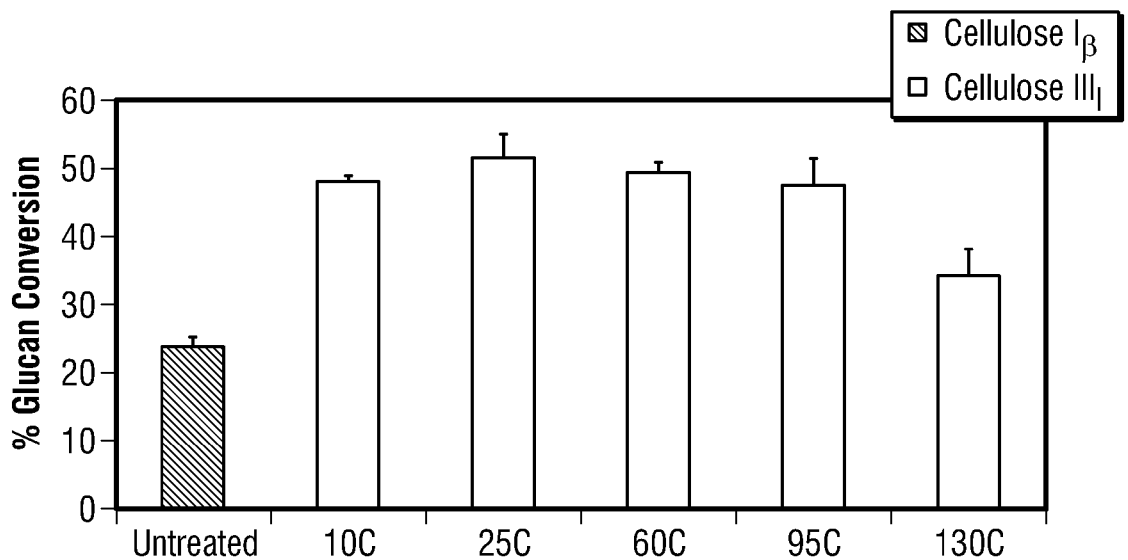
FIG. 6 shows the effect of liquid ammonia treatment temperature on the enzymatic digestibility of cellulose III in embodiments of the present invention. The cellulose III was derived from Avicel. The enzymatic digestibility of the cellulose III, at 5 different temperature regimes, was conducted for 24 hours using 1.5 FPU/g glucan of Spezyme CP (supplemented with Novo 188; FPU=filter paper units of enzyme). At temperatures above 373 K, degradation of cellulose via Maillard reactions shown below results in reducing hydrolysis yield, indicating that lower temperatures would be beneficial to minimize formation of glucan based decomposition products.

Moreover, the temperature of pretreatment with ammonia is significant. For example, Avicel (substantially pure cellulose I) was treated with liquid ammonia (7:1 ammonia:Avicel) for varying temperatures (5-130° C.) for 30 min. to study the influence of temperature during ammonia treatment on enzymatic digestibility. As shown in FIG. 6, while cellulose I was converted cellulose III under all these reaction conditions, there was a significant drop in the enzymatic activity of cellulases on the cellulose pretreated at temperatures above 100° C. and the product often darkened at the these higher temperatures. Such darkening and poor digestion may be due to the formation of Maillard degradation products which the inventors have observed are formed during high temperature ammonia based pretreatments.

Avicel is substantially pure cellulose I$_\beta$. When lignocellulosic biomass is pretreated somewhat higher temperatures can be used. Such higher temperatures can help to release lignin and other plant wall components.

Thus, while lower temperatures were generally sufficient to convert most of the cellulose I to cellulose III in substantially pure cellulosic samples, somewhat higher temperatures can be used for lignocellulosic biomass pretreatment. Useful temperatures for pretreatment of lignocellulosic biomass with liquid ammonia include temperatures ranging from about 10° C. to about 180° C. In some embodiments, the temperatures for pretreatment with liquid ammonia include temperatures ranging from about 20° C. to about 150° C. In other embodiments, the temperatures for pretreatment with liquid ammonia include temperatures ranging from about 50° C. to about 140° C. In further embodiments, the temperatures for pretreatment with liquid ammonia include temperatures ranging from about 80° C. to about 120° C. The liquid ammonia employed can be anhydrous ammonia or a solution that contains 80% or more ammonia.

The lignocellulosic biomass is generally pretreated with the selected liquid ammonia for about 1 minute to about 48 hours. In some embodiments, the pretreatment is for about 2 minutes to about 24 hours. In further embodiments, the pretreatment is for about 3 minutes to about 6 hours. In other embodiments, the pretreatment is for about 5 minutes to about 2 hours.

The ammonia to biomass ratio can vary. In particular, the ammonia to biomass weight ratio can vary from a range of 2:1 to 8:1 ammonia to biomass loading.

In one embodiment, the milled/dried lignocellulosic biomass is subjected to an liquid ammonia pretreatment for a suitable residence time, such as at least about 15 minutes or more, such as up to about 30, 60, 90, 129, 150, 180, 210 or 240 minutes, and any range there between, at a suitable temperature, such as at least about zero (0)° C. or more, such as up to about 5, 10, 15, 20, 25, 30, 35, 40, 45, 50, 55, 60, 65, 75, 80, 85, 90, 95 or 100° C., and any range or specific temperature there between. Since the milled/dried biomass is fully soaked in the liquid ammonia, the mass transfer will be improved as compared with a conventional AFEX treatment.

The liquid ammonia employed can be anhydrous liquid ammonia or a solution of 80%-99% ammonia in a solvent. In particular, the liquid ammonia used for pretreatment can be any percentage of ammonia of from about 80% to about 99% ammonia. In some embodiments, the liquid ammonia is a solution of 82%-98% ammonia in a solvent. In other embodiments, the liquid ammonia is a solution of 85%-95% ammonia in a solvent. In further embodiments, the liquid ammonia is a solution of 80%-90% ammonia in a solvent. In still further embodiments, the liquid ammonia is a solution of 87%-98% ammonia in a solvent. The solvent can be water. Alternatively, the solvent can be an organic solvent such as acetone, ethanol, methanol, isopropanol, dichloromethane, methyl acetate, ethyl acetate, chloroform and combinations thereof. The replacement of water with volatile solvents may also improve extraction of plant wall components (e.g., lignin) using the extraction procedure described herein (see Example 4). In addition, the replacement of water with volatile solvents can decrease the energy input for ammonia recovery during the process.

Also as illustrated herein cellulose III can be made from cellulose I-containing materials by using liquid ammonia in the presence of an organic solvent (e.g., acetone). In some embodiments, the solvent is water or acetone, or a combination thereof. As illustrated herein, use of acetone with ammonia during pretreatment converts cellulose I to cellulose III is a highly efficient manner. In fact substantial amounts of acetone can be used effectively. Thus, the volume:volume ratio of liquid ammonia to acetone can range from 10:90 to 99:1, or any ratio between 10:90 and 99:1. In some embodiments, the volume:volume ratio of liquid ammonia to acetone ranges from 10:90 to 80:10. In other embodiments, the volume:volume ratio of liquid ammonia to acetone can range from 20:90 to 80:10. In further embodiments, the volume:volume ratio of liquid ammonia to acetone can range from 30:90 to 70:10.

Note that the lignocellulosic biomass typically contains water. Moreover, the amount of water in the lignocellulosic biomass can vary, for example, from about 3% to 20% water. In some embodiments, the biomass is milled and dried to a suitable moisture level prior to ammonia treatment. For example, the moisture levels can be reduced to less than about 15% moisture on dry weight basis (dwb) to produce milled/dried biomass. When describing the percentage or concentration of ammonia employed for pretreatment, the amount of water in the lignocellulosic biomass is generally not considered. Thus, when referring to pretreatment using anhydrous ammonia, or a solution of 80%-99% ammonia in a solvent, the anhydrous ammonia or the solution of 80-99% ammonia is the actual pretreatment liquid added to the lignocellulosic biomass.

The liquid ammonia pretreatment can be performed in any suitable location. In one embodiment, the liquid pretreatment is performed at a centralized cellulosic biorefinery using conventional ammonia pretreated feedstocks supplied from regional biomass processing centers (Carolan et al., *J Agri Food Ind Org* 5, 10 (2007)).

The methods described herein that use high levels of liquid ammonia effectively convert cellulose I into cellulose III within the lignocellulosic biomass. This is in contrast to methods utilizing conventional AFEX pretreatment methods that require higher amounts of water and the use of high pressure reactors to maintain ammonia in the liquid phase. In general, little or no cellulose III forms within lignocellulosic biomass that is subjected to conventional AFEX pretreatment.

However, in another embodiment, the novel methods described herein are used after the lignocellulosic biomass has been subjected to a conventional pretreatment such as AFEX, ARP (ammonia recycle percolation), or the like. Such conventional pretreatments do not form cellulose III, so the cellulose I in these treated biomass samples is converted to cellulose III using excess liquid ammonia as described herein. However, the liquid ammonia pretreatment can be performed at low temperatures (<25° C.) and/or low pressures. For example the temperatures can be about 10° up to about 50° C., and the liquid ammonia pretreatment can be performed for a suitable residence time of about 0.5 hrs up to about two (2) hrs at atmospheric pressure. As a result, the biomass is successfully pretreated without the need for extensive heat and the use of high pressure reactors. In contrast to conventional high-moistures AFEX pretreatment methods, the cellulose III formed from concentrated ammonia solutions (or anhydrous ammonia) does not revert to cellulose I.

Figure 2A:
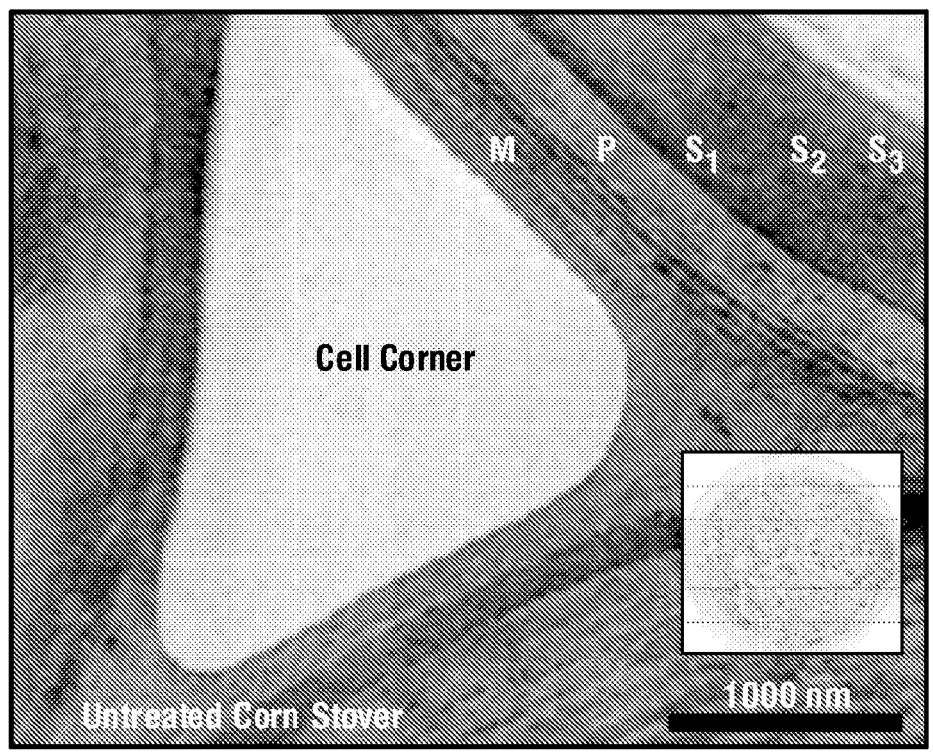
FIGS. 2A and 2B are high resolution electron microscopy images showing the tissue type and cell wall of untreated (A) and low ammonia (0.5:1 ammonia to biomass; 0.6:1 water to biomass loading) Ammonia Fiber Expansion/Explosion (AFEX) treated (B) corn stover. The letters M, P, S1, S2 and S3 stand for middle lamella, primary cell wall, and secondary cell wall layers 1-3, respectively.
Figure 2B:
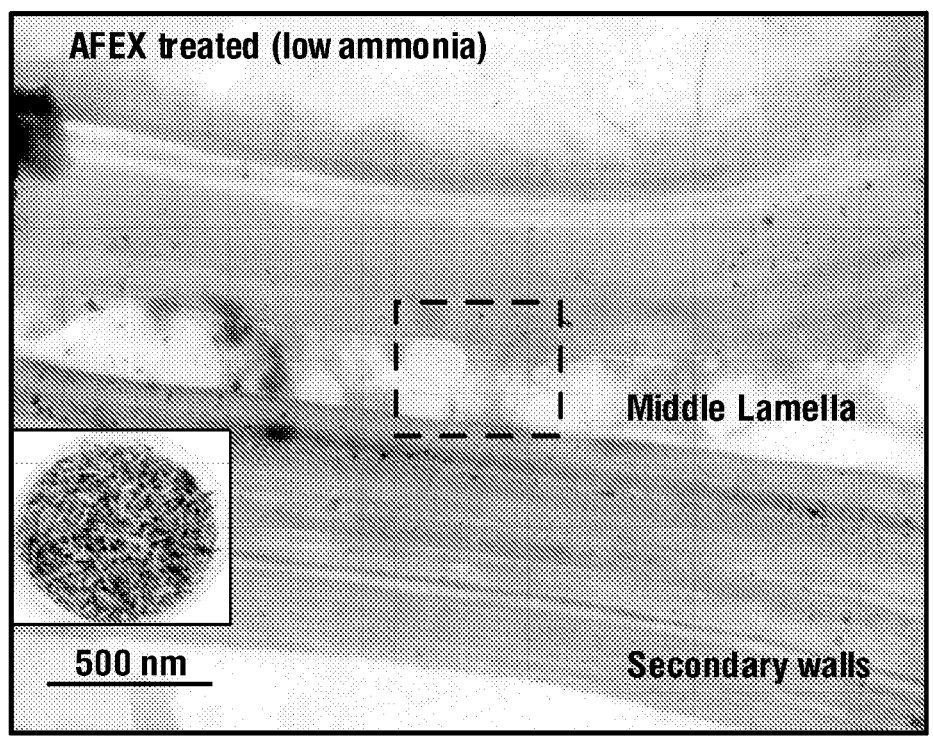

Moreover, some studies show that AFEX pretreatment increases biomass porosity, even though little conversion of cellulose I to cellulose III may occur. For example, FIGS. 2A and 2B show the plant tissue and cell wall of untreated (A) and AFEX treated (B) corn stover, respectively, as detected by high resolution electron microscopy (Chundawat, S. 2009. Chemical Engineering & Materials Science. Ph.D. Dissertation. Michigan State University, East Lansing). Thus, such AFEX treatment may make the biomass more accessible to enzyme treatment.

In one embodiment, low-cost pelletized, conventional AFEX treated feedstock is produced at regional processing centers for co-utilization as animal feed. In one embodiment, the AFEX-treated feedstock is shipped to biorefineries for further pretreatment using liquid ammonia. In this way, cellulose I is transformed to cellulose III at low temperatures, thus minimizing the need for a high pressure reactor and allowing for recovery of lignin and hemicellulose streams separately, thus allowing for production of other fuels by chemical catalysis. This would also help minimize investment in high pressure rating reactors to make cellulose III, while low-cost conventional AFEX helps disrupt LCC ester linkages to improve enzyme accessibility.

In one embodiment, treatment with liquid ammonia at low temperatures also prevents the coalescence of lignin (due to a glass transition temperature>130° C.) into enzyme inhibitory globules from secondary cell walls (Chundawat. S., 2009. Ultrastructural and physicochemical modifications within ammonia treated lignocellulosic cell walls and their influence on enzymatic digestibility Chemical Engineering & Materials Science. Ph.D. Dissertation. Michigan State University, East Lansing).

In one embodiment, lignin-carbohydrate complex (LCC) ester linkages are cleaved during pretreatment, which improve enzyme accessibility. Ammonolysis of ester bonds is facilitated at higher temperatures (>50° C.) or longer residence times (hrs to days). Chundawat, S., 2009. Ultrastructural and physicochemical modifications within ammonia treated lignocellulosic cell walls and their influence on enzymatic digestibility Chemical Engineering & Materials Science. Ph.D. Dissertation. Michigan State University, East Lansing.

Surprisingly, studies performed by the inventors indicate the total amount of enzyme absorbed onto the cellulose I allomorph may be greater than the amount absorbed onto the cellulose III allomorph. However, enzyme binding to the cellulose III allomorph is typically more productive, especially when certain combinations of enzymes are used. Thus, while enzymes may bind to the cellulose I allomorph via hydrophobic and other interactions, such binding less frequently gives rise to cleavage of the cellulosic chain. In contrast to what occurs with cellulose I, enzyme bound to the cellulose III allomorph tends to have greater processivity and the enzymes may be able to penetrate the cellulose III mass better due to greater thermal vibration of the glucan chains and reduced hydrophobicity of the cellulose III fibril surface.

Enzyme loading is reduced as compared to conventional pretreatment methods and enzymatic hydrolysis is increased as compared to conventional pretreatment methods. In one embodiment, a rate of enzymatic hydrolysis of cellulose $III_I$ is at least two times greater than the native cellulose $I_\beta$.

The cellulose III allomorph that forms from native cellulose I during liquid ammonia pretreatment has at least a two-fold, up to a 2.5 fold (or higher) rate of enzymatic hydrolysis. Surprisingly, the total amount of enzyme (including cellulase) absorbed onto the cellulose I allomorph may be greater than the amount absorbed onto the cellulose III allomorph. However, enzyme binding to the cellulose III allomorph is typically more productive, especially when certain combinations of enzymes are used. Thus, while enzymes may bind to the cellulose I allomorph via hydrophobic and other interactions, such binding gives rise to cleavage of the cellulosic chain less frequently than it does when the enzymes are bound to the cellulose III allomorph. In contrast to what occurs with cellulose I, enzyme bound to the cellulose III allomorph tend to have greater processivity. In addition, enzymes may be able to penetrate the cellulose III mass better than the more crystalline cellulose I mass, due to greater thermal vibration of the cellulose III glucan chains and reduced hydrophobicity of the cellulose III fibril surface.

According to the invention, certain enzymes and enzyme combinations are particularly effective at digesting the cellulose III allomorph. Both secreted fungal cellulases and complexed bacterial cellulosome paradigms have been explored as potential routes to deconstruct lignocellulose for biofuel applications. However, the secreted fungal enzymes of *Trichoderma reesei* are generally of greater commercial interest due to their high protein titers and significant hydrolytic activity. It is likely that the type of cellulose allomorph may also impact the extent to which a fungal cellulase can effectively extract or decrystallize cellobiosyl units from the crystal surface of the allomorph prior to formation of a catalytically active complex with the substrate that can effectively hydrolyze glycosidic linkages (see. Chundawat et al., *Deconstruction of Lignocellulosic Biomass to Fuels and Chemicals*, Annu. Rev. Chem. Biomol. 2 (2011), which is specifically incorporated herein by reference in its entirety). The increased flexibility of the glucan chains within cellulose III is dependent on its crystal structure and results in enhanced overall hydrolysis yields.

However, not all observed enhancements can be attributed to the restructuring of cellulose structure, as a significant gain in digestion efficiency is seen only for certain mixtures of exocellulases and endocellulases. As illustrated herein, addition of endoglucanases significantly accelerated the depolymerization of cellulose III compared to use of exocellulases alone.

Crude fungal cellulase mixtures are typically composed of 50-80% exocellulases (40-60% Cel7A, 10-20% Cel6A) and 10-25% endocellulases (5-10% Cel7B, 1-10% Cel5A, 1-5% Cel12A, <1% Cel61A) (Rosgaard et al., Biotechnol. Prog. 23(6): 1270-76 (2007)).

But, as illustrated herein such mixtures do not include significant amounts of the most effective combinations of cellulases. Thus, the inventors have found that Cel7B was the most effective degradation enzyme for cellulose, followed by Cel5A, Cel12A, and Cel61A. Endocellulases create endo-cuts randomly along glucan polymer chains for cellulose crystals that result in synergistically enhanced exocellulase activity. The synergistic activity of endocellulases and exocellulases allowed near theoretical glucan conversions to glucose at industrially-relevant low enzyme loadings for cellulose III. In contrast, previously reported procedures employed 10-20 fold higher amounts of Cel7A with no endocellulase addition but achieved significantly less than theoretical glucan conversion (Igarashi et al., FEBS Journal 274(7): 1785-92 (2007)). When lower crystallinity plant-derived cellulose III substrates are hydrolyzed at low enzyme loadings that are relevant to industrial processing (<10 mg total enzyme loading/g glucan), the inventors have found that only when Cel7A is combined with suitable endoglucanases was there any significant improvement in overall glucan conversion.

For example, enzymes that may be employed include, for example, a cellulolytic enzyme, e.g., cellulase, endoglucanase, cellobiohydrolase, and beta-glucosidase. In another embodiment, the enzyme can be a hemicellulase, esterase, protease, laccase, peroxidase, or a mixture thereof. Additional examples of enzymes that can be used to digest the cellulose III allomorph include a cellobiohydrolase and/or an endocellulase. Examples of such a cellobiohydrolase and/or an endocellulase include Cel7A, Cel6A, Cel7B, Cel 5A-tr, Cel61A, Cel61B, Cel5A-ac, and Cel12A (see website at www.cazy.org).

In some embodiments, a combination of enzymes may be used that includes Cel7B. Such a combination can include two or more enzymes. In other embodiments, a combination of three or more of such enzymes that can be employed. Data provided herein shows that a combination of the following enzymes is highly effective for digesting the cellulose III allomorph: Cel7A and Cel7B. Additional data provided herein shows that a combination of the following enzymes is highly effective for digesting the cellulose III allomorph: Cel7A, Cel6A and Cel7B. Further data provided herein shows that a combination of the following enzymes is highly effective for digesting the cellulose III allomorph: Cel7A, Cel6A and Cel5A_tr and/or Cel7A. Cel6A and Cel5A_ac. In some embodiments, the cellulose III allomorph is digested to a greater extent by such a combination of enzymes than is cellulose I.

Such enzymes can be obtained from a variety of sources, including *Trichoderma reesei*.

Extraction of Plant Wall Components

Nearly all forms of lignocellulosic biomass, i.e., plant biomass, such as monocots, comprise three primary chemical fractions: hemicellulose, cellulose, and lignin. Hemicellulose is a polymer of short, highly-branched chains of mostly five-carbon pentose sugars (xylose and arabinose), and to a lesser extent six-carbon hexose sugars (galactose, glucose and mannose). Dicots, on the other hand, have a high content of pectate and/or pectin, which is a polymer of alpha-linked glucuronic acid. Pectate may be "decorated" with mannose or rhamnose sugars, also. These sugars are highly substituted with acetic acid.

Typical ranges of hemicellulose, cellulose, and lignin concentrations in plants are shown at the website ww1.eere.energy.gov/biomass/feedstock_databases.html. Cellulose typically makes up 30 to 50% of residues from agricultural, municipal, and forestry sources. Cellulose is more difficult to hydrolyze than hemicellulose, but, once hydrolyzed, converts more efficiently into ethanol with glucose fermentation than hemicellulose. Because of its branched structure, hemicellulose is amorphous and relatively easy to hydrolyze (breakdown or cleave) to its individual constituent sugars by enzyme or dilute acid treatment. In contrast, the sugar polymers of hemicellulose are relatively easy to hydrolyze, but do not convert as efficiently as cellulose using standard fermentation microbial strains (which produce ethanol from glucose). Although hemicellulose sugars represent the "low-hanging" fruit for conversion to ethanol, the substantially higher content of cellulose represents the greater potential for maximizing alcohol yields, such as ethanol, on a per ton basis of plant biomass.

As described above, cellulose is a linear polymer of glucose sugars, much like starch, which is the primary substrate of corn grain in dry grain and wet mill ethanol plants. However, unlike starch, the glucose sugars of cellulose are strung together by β-glycosidic linkages, which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Specifically, cellulose crystallinity, lignin-carbohydrate complex (LCC) ester linkages and non-specific enzyme binding to cell wall components (such as lignin) are known to be major rate-limiting steps to efficient cell wall deconstruction.

Lignin, which is a polymer of phenolic molecules, provides structural integrity to plants, and remains as residual material after the sugars in plant biomass have been fermented to ethanol. Lignin is a by-product of alcohol production and is considered a premium quality solid fuel because of its low sulfur content and heating value, which is near that of sub-bituminous coal.

However, enzymes and microbes used to digest cellulosic materials and ferment useful sugars are inhibited due to interaction with lignin. Other plant wall materials and decomposition products produced by pretreatment can inhibit these enzymes and microbes as well (Pan, *J. Biobased Mater. Bioenergy* 2 (1), 25-32 (2008); Klinke et al., *Applied Microbiology and Biotechnology* 66 (1), 10-26 (2004)). The extent of these inhibitions depends on the pretreatment conditions and how the cell wall is modified during pretreatment.

The biomass pretreatment methods described herein that employ liquid ammonia and that result in the formation of the highly digestible cellulose III allomorph can be adapted to include extraction of biologically inhibitory cell wall components (i.e., lignin, lignin decomposition products, xylo-oligosaccharides, amides). The cell wall components can be extracted from the lignocellulosic biomass during or after liquid ammonia pretreatment. By stabilizing cellulose III using the pretreatment process described herein, and by extracting out recalcitrant lignin/lignin degradation compounds, enzyme loading can be reduced, and the enzymatic hydrolysis rate can be increased.

The removal of lignin and hemicellulose improves the accessibility of the enzymes to cellulose by increasing its exposed surface area to volume ratio to the enzymes. Recent advances show that AFEX pretreatment increases biomass porosity, even though little conversion of cellulose I to cellulose III may occur. For example, FIGS. 2A and 2B show the plant tissue and cell wall of untreated (A) and AFEX treated (B) corn stover, respectively, as detected by high resolution electron microscopy (Chundawat, S., 2009. Chemical Engineering & Materials Science. Ph.D. Dissertation. Michigan State University, East Lansing). Thus, AFEX treatment, for example, before liquid ammonia pretreatment can make the biomass more accessible to enzyme treatment.

As noted above, lignin generally inhibits enzymatic and microbial digestion/fermentation of pretreated biomass. Therefore, another aspect of the invention involves methods for removal of lignin, including degraded lignin and other cell wall decomposition products, to reduce enzyme loading and improve hydrolyzate fermentability. Such methods can improve the economical viability of a cellulosic biorefinery.

Embodiments of the invention permit recovery of two fractions, namely, a cellulose-rich stream and a hemicellulose-lignin rich stream, for example, during or after ammonia pretreatment. As illustrated herein, lignin is mobilized by ammonia pretreatment and significant amounts can be removed by extraction pursuant to such ammonia pretreatment.

Figure 1A:
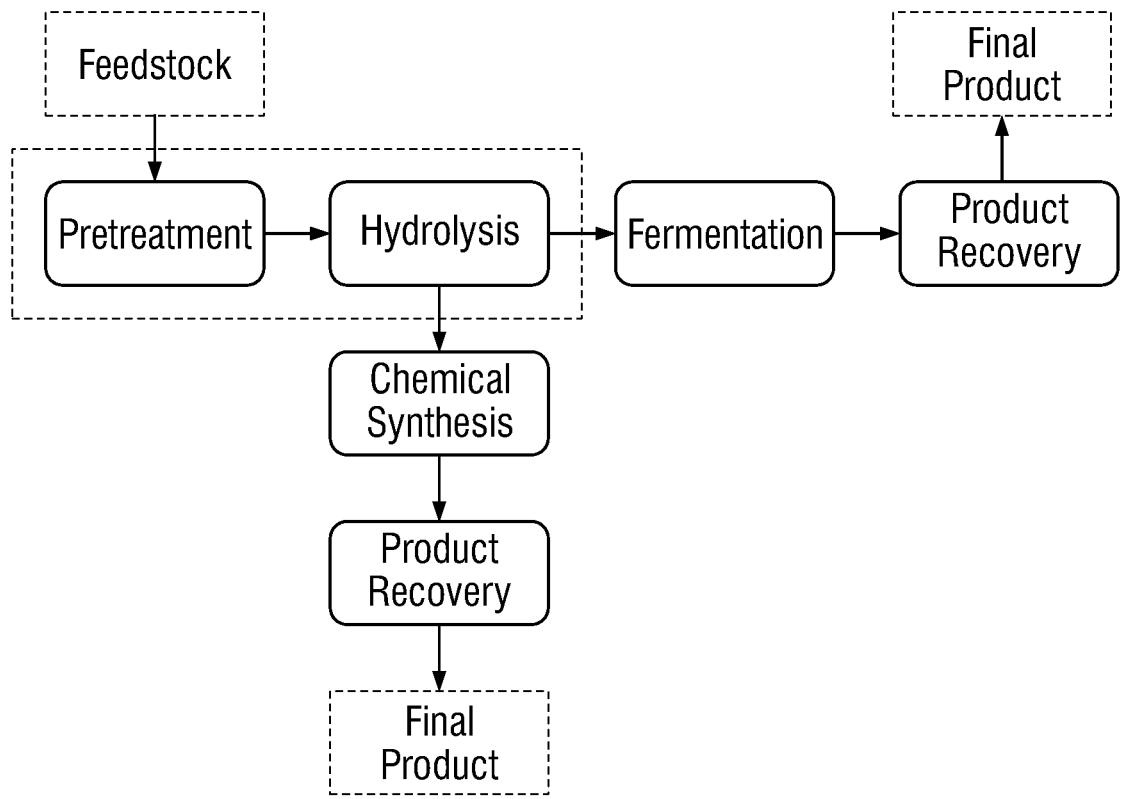
FIG. 1A is a process flow diagram showing biochemical conversion of lignocellulosic biomass.
Figure 1B:
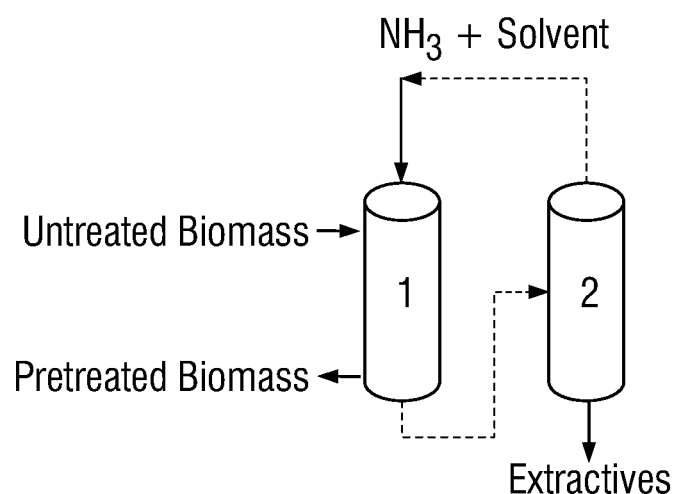
FIG. 1B shows a process diagram for extractive liquid ammonia-based pretreatment carried out on lignocellulosic biomass. The process involves use of: 1) an ammonia pretreatment cell and 2) an extractives collection/separations cell.

Thus, for example, a reactor capable of performing plant wall component extraction can be employed that has two major parts: 1) an ammonia pretreatment cell and 2) an extractives collection cell (FIG. 1B). Ammonia pretreatment can be performed in the ammonia pretreatment cell. Such pretreatment solubilizes the extractives that will be released from the biomass. Once the selected reaction time has transpired, the extractives collection cell is set to the same pressure as the ammonia pretreatment cell using pressurized nitrogen and the valve between these two cells is opened. Nitrogen overpressure can be applied to prevent ammonia vaporization in the ammonia pretreatment cell and to drive the liquid phase to flow down to the extractives collection cell. A filter present in the bottom of the ammonia pretreatment cell prevents the solids from flowing down into the extractives collector, but the filter has pores of sufficient porosity to permit liquids and solubilized plant wall components to pass through. For example, the filter can be a 50 micron, 80 micron or 100 micron filter. A valve can be used for venting the extractive collector to exhaust chamber so that the nitrogen/ammonia vapor can flow into the exhaust chamber and this flow can be regulated to prevent rapid evaporation of ammonia in the extraction cell. After the extractives are removed from the ammonia pretreatment cell, nitrogen overpressure valve is shut down and the gas in the extractives collection cell is slowly released to the exhaust chamber until the system reaches atmospheric pressure. At this point, the pretreated biomass and the respective extractives can be removed from the system for further analysis.

In one embodiment, after the defined residence time, the liquid fraction (i.e., liquid ammonia along with soluble decomposition products, lignin and xylo-oligosaccharides) is separated from the solids (which will be cellulose III rich after this stage). The ammonia can then be further evaporated from the liquid fraction, to produce cell wall extractives and recovered ammonia. In one embodiment, the recovered ammonia is reused or recycled into the ammonia pretreatment process. The quantity of ammonia consumed during pretreatment (i.e., ammonolysis reactions with cell wall esters) can also be replenished or supplemented at this stage. In other embodiments, the liquid ammonia with the extractives can be used in a continuous manner to pretreat the next batch of untreated biomass before recovering the ammonia from the extractives. Thus, the novel methods described herein can be performed on a continuous mode or as a batch operation.

In one embodiment, the cellulose rich solids fraction is used to produce biofuels (after enzymatic hydrolysis and fermentation). The cellulose rich solids fraction can be separated from hemicellulose and lignin. The hemicellulose and lignin can also be separated. Hemicellulose used for other applications, including, but not limited to, as soluble inducers for microbes to produce hemicellulases, fuels and/or other products using, for example, chemical catalysis, and the like. The isolated lignin is also useful in several applications including, but not limited to, combustion to produce electricity, chemical synthesis through catalysis and/or as resin/binders in the production of biomaterials, and the like.

Liquid fuels and chemicals can be produced from lignocellulosic biomass utilizing methods based on the "sugar platform." In this process the lignocellulosic biomass is pretreated and hydrolyzed using enzymes to produce fermentable sugars as described above. These sugars can then either be used as a carbon source for fermentative microorganisms to produce fuels/chemicals and/or used directly in chemical synthesis through catalytic processes as shown in FIG. 1. With this process, pretreatment and enzymatic hydrolysis constitute the basis for deconstructing the plant cell wall into fermentable sugars, which can be used to produce commercially useful products, such as various chemicals via chemical synthesis and/or biofuels via fermentation.

Conventional Pretreatments

Various pretreatment methods are known in the art. Such treatments include, for example, concentrated acid hydrolysis pretreatments and two-stage acid hydrolysis pretreatments. Other pretreatments include hydrothermal or chemical pretreatments, followed by an enzymatic hydrolysis (i.e., enzyme-catalyzed hydrolysis) or simultaneous enzymatic hydrolysis and saccharification. Yet other pretreatment methods can include dilute acid hydrolysis (Schell et al., Applied Biochemistry and Biotechnology 105(1-3): p. 69-85 (2003); Wyman et al. in *AIChE Annual Meeting*. San Francisco, Calif. (2006); Wyman, *Integration of Leading Biomass Pretreatment Technologies with Enzymatic Digestion and Hydrolyzate Fermentation*, Department of Energy. p. 1-10 (2005); Mohagheghi et al., Appl Biochem Biotechnol. 33: 67-81 (1992); Eggeman & Elander, *Process and economic analysis of pretreatment technologies*. Bioresource Technology 96(18): 2019-2025 (2005); Varga et al., Applied Biochemistry and Biotechnology 114(1-3): 509-523 (2004)). In addition, some pretreatments involve high pressure hot water-based methods, i.e., hydrothermal treatments such as steam explosion (Playne, Biotechnology and Bioengineering 26(5): p. 426-433 (1984); Mackie et al., Journal of Wood Chemistry and Technology 5(3): 405-425 (1985); Ballesteros et al., Applied Biochemistry and Biotechnology 130(1-3): 496-508 (2006); Hongzhang & Liying, Bioresource Technology 98(3): 666-676 (2007)). Other pretreatments involve aqueous hot water extraction, reactor systems (e.g., batch, continuous flow, counter-flow, flow-through, and the like), AFEX, ammonia recycled percolation (ARP), lime treatment and a pH-based treatment.

Ammonia based pretreatments promote the hydrolysis of ester bonds due to the presence of hydroxyl ions and ammonia forming hydrolysis (e.g., acids) and ammonolysis (e.g., amides) degradation products, respectively. For processes where ammonia is highly concentrated, ammonolysis reactions are predominant, reducing the toxicity of the hydrolyzates. Similar to other alkali pretreatments (NaOH, CaOH) disruption of LCC linkages during AFEX promotes the relocalization of lignin and hemicelluloses away from cellulose (Chundawat, S., 2009. Chemical Engineering & Materials Science. Ph.D. Dissertation. Michigan State University, East Lansing); Balan et al., Biotechnology Progress 25(2): 365-375 (2009); Yoon et al., Applied Biochemistry and Biotechnology 51-52(1): 5-19 (1995); Kim & Lee, Bioresource Technology 96(18): 2007-2013 (2005); Kim et al., Applied Biochemistry and Biotechnology 133(1): 41-57 (2006).

Temperatures in these procedures can range from about 50 to about 290° C. Ammonia recycled percolation (ARP) and dilute ammonium hydroxide technologies, for example, utilize temperatures of about 150 to about 180° C., have residence times of about 30 to 120 min, utilize a high pressure liquid recycle, and have a water loading of about three (3) to 20 g water per gm dry weight biomass. With these methods, biomass is separated into solid and liquid fractions by separating hemicellulose and lignin from cellulose into liquid fraction (typically resulting in a low solid loading), followed by neutralization and/or ammonia recovery for downstream processing. However, neither ARP nor conventional ammonium hydroxide based treatments produce significant cellulose III (which is more digestible than native cellulose I).

In addition, pretreatment-hydrolysis of plant biomass according to conventional methods, such as those referenced above, can often result in the creation and release of other chemicals that inhibit microbial fermentation. These inhibitors (e.g., furfural) are largely the products of sugar degradation, and methods to remove these inhibitors or to reduce their formation are needed. Alternatively, microbial strains resistant to the inhibitors are needed.

Several of these methods generate nearly complete hydrolysis of the hemicellulose fraction to efficiently recover high yields of the soluble pentose sugars. However, chemical solubilization of hemicellulose also produces toxic products, such as furan derivatives, which can inhibit downstream microbial reactions (e.g., fermentation). Regardless, the hydrolysis of hemicellulose facilitates the physical removal of the surrounding hemicellulose and lignin, thus exposing the cellulose to later processing. However, most, if not all, of conventional pretreatment approaches do not significantly hydrolyze the cellulose fraction of biomass.

In contrast to the conventional pretreatments described above, conversion of cellulose I to amorphous cellulose or cellulose III$_1$ during pretreatment as described herein results in highly digestible biomass. In one embodiment, the biomass used for this process is plant lignocellulosic biomass.

Biomass conversion to alcohol also poses unique fermentation considerations. The *Saccharomyces cerevisiae* yeast strains used in conventional corn ethanol plants, for example, can ferment glucose, but cannot ferment pentose sugars such as xylose. Additionally, there is currently no naturally occurring microorganism that can effectively convert all the major sugars present in plant biomass to ethanol. Therefore, genetically engineered yeast or bacteria, which can, in theory, ferment both glucose and xylose to alcohol, are being used for biomass to alcohol processes. However, in practice, co-fermentation is inefficient and glucose fermentation is still the main reaction for ethanol production. Furthermore, genetically-enhanced recombinant strains of fermentative microorganisms, including recombinant strains of yeast, bacteria and fungi, as well as transgenic nucleic acids (DNA, RNA) derived from such component may pose environmental disposal and permitting problems.

The invention will be further described by reference to the following examples, which are offered to further illustrate various embodiments of the present invention. It should be understood, however, that many variations and modifications may be made while remaining within the scope of the present invention.

Example 1

Low Temperature Ammonia Treatment

This Example describes some of the properties of different cellulose polymorphs and discusses whether the source of cellulose affects conversion of cellulose to forms that are more optimally digested by enzymes.

Quantitative information regarding a change in structure upon treatment of various cellulosic substrates was obtained by observing the relative change in peak intensity for various cellulose X-ray diffraction spectral peaks ($2\theta=12°$, $20°$, $22°$). In general, the height of the $2\theta$ peak at $18°$ is a measure of the amount of cellulose amorphous phase whereas the $2\theta$ peak at $22°$ is a measure of the amount of crystalline cellulose I. The 18/22 peak ratio is commonly known as crystallinity index (CrI) that is calculated for the relative change in intensity for the peak at $22°$.

Cellulose (AVICEL) was treated in a variety of ways and the crystallinity index of the product was determined. Avicel is essentially pure cellulose I. Cellulose III was generated from Avicel by treatment of Avicel with 7:1 ammonia: biomass (wt.:wt.) for 2 hr at 95° C. (and at 10° C. in some embodiments), where the Avicel sometimes had residual moisture of 0.05 water g gram Avicel. Ammonium hydroxide treated Avicel involved use of 10:1 ratio of 28-30% ammonia to Avicel (wt.:wt.) for 60 min. at 4° C.

Untreated AVICEL was determined to have a crystallinity index of about 0.65, while that of ammonium hydroxide treated AVICEL was approximately three percent (+3%) higher, indicating a slightly more crystalline substrate. The slightly higher crystallinity index of ammonium hydroxide-treated AVICEL may be due to extraction/removal of residual amorphous fractions from native AVICEL. In contrast, treatment of AVICEL with sodium hydroxide resulted in an 18% decrease in crystallinity index (based on the 22° peak) accompanied by a 66% increase in the peak at 20°, which was a typical characteristic of cellulose II polymorphs.

Treatment of AVICEL with liquid ammonia resulted in a 75% decrease in crystallinity index, accompanied by a 72% increase in the peak at 20°. There was a similar decrease in crystallinity index (by 70%) for amorphous cellulose, but there was no corresponding increase in the relative intensity of the peak at 20°, which is likely due to the lack of any significant crystallinity in phosphoric acid-pretreated amorphous cellulose.

In order to study the effect of cellulose source on the extent of transformation of native cellulose I to III, three types of native cellulose I biomass were obtained: AVICEL (processed microcrystalline cellulose), cotton linter (fine, silky fibers which adhere to the seeds of a cotton plant after ginning) and cotton. Cotton linter is the short fiber of the cotton ball that grows between the cotton seeds and the long boll cotton fibers. The degree of polymerization (DP) of AVICEL, linter and cotton has been reported to be in the range of 150-250, 750-1000 and 5000-10,000, respectively.

Liquid ammonia treatment involved 7:1 ammonia:linters or cotton fibers (wt.:wt.) for 0.5 hr at 10° C. (or at 95° C. in some embodiments), where the biomass sometimes had residual moisture of 0.05 water g gram biomass.

Representative X-ray diffraction spectra for cellulose biomass subjected to various treatment conditions, including ammonia treatment, are shown in FIG. 4. The spectra for the untreated AVICEL, cotton linter and cotton celluloses are independent of the cellulose sources and are typical of a cellulose $I_\beta$ crystal polymorph. Treatment with liquid ammonia resulted in a similar modification of the X-ray diffraction spectra for all three celluloses, as depicted by the appearance of the $2\theta$ peak at 12° and disappearance of the $2\theta$ peak at 22°. The crystallinity index (or Pk 18/22) decreased by 78-83% after liquid ammonia treatment of cotton linter and cotton cellulose, accompanied by a corresponding increase of 48-60% for Pk 18/20.

FIG. 4A shows powder X-ray diffraction spectra of cellulose (Cellulose I) treated with liquid ammonia (to form Cellulose III), sodium hydroxide (to form Cellulose II), ammonium hydroxide and concentrated phosphoric acid (Amorphous Cellulose) where AVICEL (processed microcrystalline cellulose) was the cellulosic substrate. Y-axis and X-axis depict intensity counts and two-theta angles, respectively.

FIG. 4B shows powder X-ray diffraction spectra of untreated (Cellulose I) and liquid ammonia (Cellulose III) treated celluloses where AVICEL, cotton linters and native cotton were the cellulosic substrates used. Y-axis and X-axis depict intensity counts and two-theta angles, respectively. These results show that cellulose crystallinity is a major rate limiting factor during hydrolysis, which can be addressed either by using inexpensive ammonia (at appropriate pretreatment conditions) or by using expensive ionic liquid or phosphoric acid based pretreatments.

Additionally, it was determined that aqueous ammonium hydroxide (e.g. as used during certain ammonia pretreatments like ARP and others) does not increase cellulose degradability, because it does not lead to formation of cellulose III. Thus, treatment of cellulosic biomass with 1:1 ammonia to biomass (wt.:wt.) with 0.6:1 water:biomass (wt.:wt.) for 15 min. at 130° C., was not as effective as the liquid ammonia pretreatment.

Figure 5:
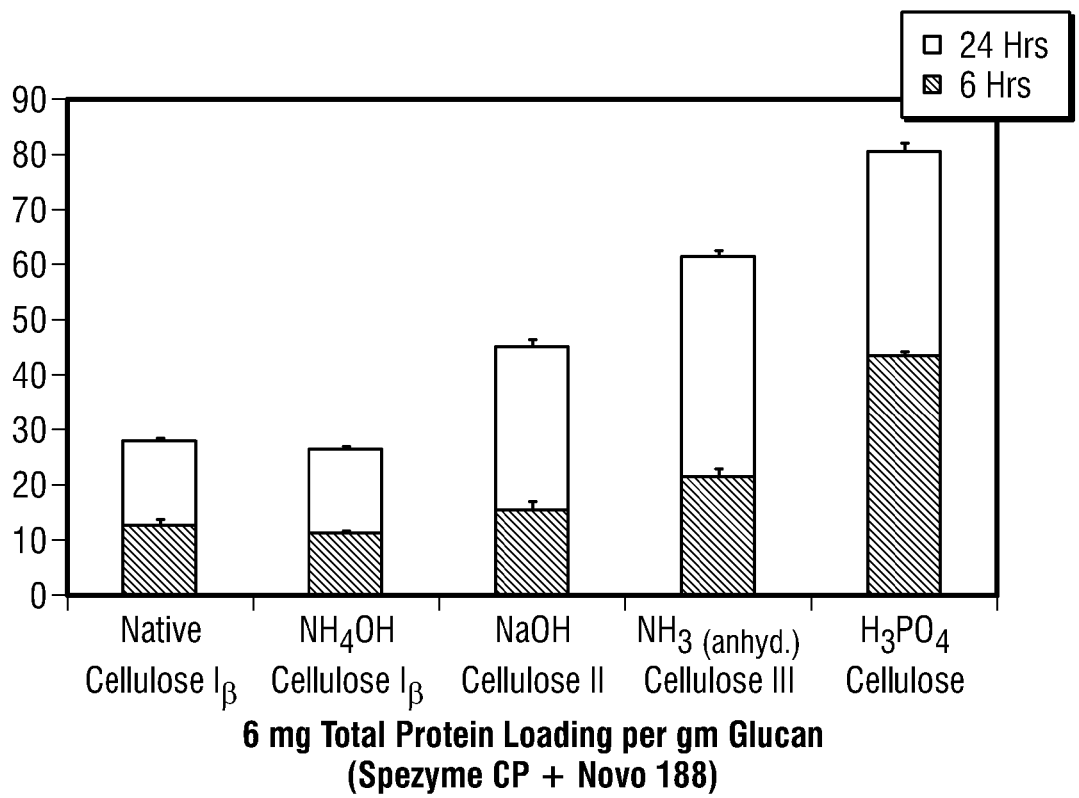
FIG. 5 shows the percent glucan conversion of different cellulose allomorphs (see FIG. 4A for details on sample preparation conditions) when submitted to enzymatic hydrolysis for 6 and 24 hours by SPEZYME CP and NOVOZYME 188 at 50° C. in embodiments of the present invention.

In another study, the enzymatic hydrolysis yield was determined at two time points for native cellulose I (AVICEL) after liquid ammonia pretreatment or after pretreatment with aqueous ammonium hydroxide (30%), aqueous sodium hydroxide, or concentrated phosphoric acid. Cellulase at 1.5 FPU per gram of glucan was used for enzymatic hydrolysis. For anhydrous liquid ammonia-based pretreatment (ALAP), 5:1 liquid ammonia to dry biomass AVICEL (w/w) was incubated at 10° C. for 30 minutes followed by drying under the hood overnight. The dried product was then analyzed by X-ray diffraction (XRD) analysis. Such treatment led to formation of cellulose III that had a 2-2.5 fold increase in plant cellulose degradability after 24 hours of hydrolysis using 3 mg/g glucan of a 3:5 ratio of SPEZYME CP and NOVOZYME 188 (total enzyme loading of 6 mg/g glucan). FIG. 5 shows glucan conversion of the cellulose allomorphs formed by the different pretreatments (ammonium hydroxide, sodium hydroxide, anhydrous liquid ammonia and phosphoric acid) when subsequently subjected to enzymatic hydrolysis for 6 and 24 hours by SPEZYME CP and NOVOZYME 188 at 50° C.

The effect of temperature (i.e., 10, 25, 60, and 95° C.) on the liquid ammonia formation of cellulose III and enzymatic hydrolysis rate was examined for AVICEL cellulose. Cellulose III was generated from Avicel by treatment of Avicel 7:1 ammonia:Avicel (wt.:wt.) for 0.5 hr at varying temperatures, where the Avicel may have had residual moisture of 0.05 water g gram Avicel.

Enzyme loading was 1.5 FPU/g glucan of SPEZYME CP (supplemented with NOVOZYME 188). FIG. 6 shows the effect of liquid ammonia treatment temperature on the enzymatic digestibility of cellulose III polymorph. The Y-axis depicts total glucan conversion after 24 hours of hydrolysis. In all cases, there was an approximately two-fold increase in the glucan yield compared to untreated cellulose I. However, the enzymatic digestibility of cellulose did not vary significantly when liquid ammonia pretreatment was performed at a variety of temperatures from 10-95° C. This would suggest that the formation of cellulose III is largely independent of temperature and that the major factor is that the amount liquid ammonia should be sufficient to completely swell the cellulose fibrils.

It should be noted, however, that increasing the temperature above 100° C. resulted in reduced glucan conversion (FIG. 6). The enzymatic digestibility of the cellulose samples after treatment with liquid ammonia at temperatures above 100° C. resulted in significantly lower enzymatic hydrolysis yields than cellulose III prepared at temperatures below 100° C. In many cases, the hydrolysis yields were comparable to or significantly lower than native cellulose I.

Treatment with liquid ammonia at temperatures above 100° C. also led to considerable darkening of the treated samples. Darkening of cellulose at temperatures above 100° C. may be due to Maillard based reactions, which are chemical reactions between an ammonia and a reducing sugar (illustrated below).

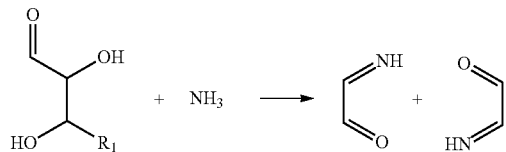

Such Maillard based reactions are known to be promoted by high temperatures, low moisture and high alkalinity. Maillard reaction products (and alkali induced peeling reaction products) are known to inhibit cellulases as well as other enzymes.

Studies with anhydrous liquid ammonia and celluloses (using AVICEL and Linters) indicate that an activation time of 30 min was more than sufficient when excess liquid ammonia is used to completely soak the substrate. Therefore, according to the invention high temperatures are not needed to accelerate the formation of cellulose III. Such high temperatures may even be detrimental to release of useful sugars and saccharides from cellulose.

Enhancement of the hydrolysis yield after anhydrous liquid ammonia treatment (10° C. for 30 min) was explored further to compare cotton linters and native cotton cellulosic substrates with the results obtained for AVICEL. After treatment with anhydrous liquid ammonia, the cellulosic substrates were hydrolyzed by two different amounts (6 and 60 mg/g glucan) of a crude cellulase complex (SPEZYME CP supplemented with NOVOZYME 188) for 6-24 hours. The two amounts of enzyme loadings corresponded to 1.5 and 15 FPU cellulase loading/g glucan.

FIG. 7 shows the enzymatic digestibility of untreated (Cellulose I) and liquid ammonia (Cellulose III) treated linter cotton and cotton celluloses after 6 or 24 hours of hydrolysis. To generate cellulose III in these cellulose biomass materials, the biomass was treated with 7:1 ammonia:biomass (wt.:wt.) for 0.5 hr at 10° C.

The extent of enzyme digestion of untreated cotton linters and fibers was significantly lower than observed for the ammonia treated samples. However, a 2-2.5 fold increase in overall yield for 6 mg/g glucan enzyme loading after 6 and 24 hours of hydrolysis was observed for both liquid ammonia-treated linter and cotton fibers as compared to their untreated counterparts. The relative increase in the glucan digestibility after liquid ammonia treatment of cotton linters and cotton fibers is slightly higher compared to AVICEL at the same protein loading. This may be because the cotton and linters fibers are composed of higher degree of polymerization (DP) cellulose that may benefit more from the transformation of cellulose I to III, thereby leading to proportionately larger increase in cellulase activity.

Example 2

Anhydrous Pretreatment Conditions

This Example illustrates that anhydrous ammonia pretreatment of cellulosic materials is more effective than conventional AFEX treatment.

Preliminary tests were performed to evaluate what conditions affect the amount and type of crystalline cellulose allomorphs formed from cellulose I (AVICEL). In particular, the effect of conventional ammonia fiber expansion (AFEX) based pretreatment parameters (ammonia loading, water loading, residence time) was studied to quantify the extent of conversion of cellulose I to III was studied using Raman spectroscopy to detect the cellulose allomorphs. For this initial study, AVICEL was used as the cellulosic substrate. Four conditions were explored;
a. (a) (1-NH3, 0.6-W) 1 gm ammonia and 0.6 gm water loading per gm of substrate at 100° C. for 15 min,
b. (b) (3-NH3, 0.6-W), 3 gm ammonia and 0.6 gm water loading per gm of substrate at 100° C. for 45 min,
c. (c) (1-NH3, 0.05-W) 1 gm ammonia and 0.05 gm water loading per gm of substrate at 100° C. for 15 min, and
d. (d) (3-NH3, 0.05-W) 3 gm ammonia and 0.05 gm water loading per gm of substrate at 100° C. for 45 min.
Liquid ammonia treated AVICEL (10° C., 30 min) was the control, where the ammonia loading employed ranged between 5-7 gm ammonia per gm substrate containing 0.05 gm water/gm substrate.

The extent of cellulose $I_\beta$ to $III_I$ transformation was estimated by the relative intensity of peaks at 380 and 350 cm$^{-1}$, with respect to a 100% cellulose IIII standard sample, which exhibited an 82% decrease in the relative peak ratio.

As shown in FIG. 8A, none of the four conditions gave complete conversion of AVICEL to cellulose III. However, the extent of conversion of AVICEL to cellulose III was dependent on the conditions employed and such partial conversion provides insight into the factors that impact the formation of cellulose III. Conditions containing significant moisture (1NH3-0.6 W and 3NH3-0.6 W) had little effect on cellulose I, with only a 3 and 6% conversion to cellulose III. In fact, only when pretreatment was carried out in the absence of substantial amounts of water and in presence of sufficient ammonia to completely soak the substrate (3NH3-0.05 W) was there a significant conversion to cellulose III (of 39%) (FIG. 8A). These data indicate that the presence of water during ammonia pretreatment tends to inhibit formation of cellulose III from cellulose I.

The presence of anhydrous liquid ammonia was also useful for complete transformation of cellulose I to III in corn stover (FIG. 8B). Thus, no cellulose III was formed during conventional AFEX, involving treatment with 62% $NH_4OH$ at 130° C. for 15 minutes. Even though conventional AFEX typically employs higher temperatures, the conversion to cellulose III is minimal or non-existent. In fact cellulose III was only formed from AFEX-treated corn stover (AFEX CS, containing 0.05% water per gram biomass) when it was further subjected to anhydrous liquid ammonia (7:1 ammonia:biomass) at 25° C. for 2 hrs. After such treatment with anhydrous liquid ammonia, the cellulose was highly digestible and high levels of glucan conversion were obtained from the pre-treated corn stover (FIG. 8B).

These data indicate that absence of water during ammonia treatment allows stable formation of cellulose III, which does not occur when treating cellulose I during conventional AFEX. Thus, soaking the substrate completely in liquid ammonia under substantially anhydrous conditions allowed for completion of the transformation of cellulose I to III.

Example 3

Ammonia to Biomass Ratios

This Example examines the effect of ammonia to biomass loading ratios on cellulose III formation.

Avicel was used as biomass. The weight:weight ratio of ammonia to biomass was varied during pretreatment. In particular, the ratios of ammonia to biomass (wt.:wt.) tested were 6:1, 3:1, 2:1 and 1:1. All treatments were carried out at 25° C. The amount of cellulose III formed after either 0 or 10 minutes was detected by X-ray diffraction analysis, where 0 min indicates that samples were immediately removed after immersion in liquid anhydrous ammonia.

As shown in FIG. 9, when the ammonia:biomass loading was 1:1, no cellulose III is formed within 10 minutes. However, when the ammonia to biomass loading was increased to 2:1, a significant conversion of cellulose I to III was observed. In particular, when the 2:1 ammonia to biomass ratio was used about 50-60% conversion of cellulose I to cellulose III was observed. However, when the ammonia to biomass loading exceeded 3:1 there was complete conversion of cellulose I to cellulose III.

Moreover, in other experiments involving extractive AFEX where a 7:1 ammonia to biomass loading was employed, complete conversion of cellulose I to cellulose III was observed.

Example 4

Extractive Anhydrous Ammonia Pretreatment

This Example describes conditions for optimizing pretreatment conditions for forming cellulose III using a realistic lignocellulosic feedstock such as corn stover.

The inventors have shown that conventional AFEX pretreatment enhances plant cell wall saccharification rate by delocalizing lignin/hemicellulose and increasing cellulase access to embedded crystalline cellulose fibrils. However, there is no significant cellulose decrystallization of cellulose I or even significant formation of detectable amounts of cellulose III during conventional AFEX of plant cell walls.

But formation of cellulose III is important to optimize enzyme digestibility of cellulosic material. Thus, the inventors have observed that there was an 80% increase in glucan digestibility within 6 hrs of enzymatic hydrolysis for cellulose III rich AFEX corn stover compared to cellulose I rich AFEX corn stover, indicating that formation of cellulose III within a realistic lignocellulosic biomass can indeed improve overall hydrolysis yields.

The inventors' studies indicate that AFEX procedures can be adapted to produce substantial percentages of cellulose III and recover ammonia. Using high levels of liquid ammonia (e.g., rather than more dilute aqueous ammonia or NaOH) can minimize water usage in the biorefinery and is likely to be less environmentally problematic than other procedures (e.g., use of NaOH). Designing economical pretreatments that maximize accessible cellulose surface area for enzyme attack while minimizing the thermodynamic cost for solvent-exposed glucan chain decrystallization by cellulases leads to enhanced biomass hydrolysis rates and improved, more cost-effective cellulosic biorefineries.

The benefits of delignification on plant cell wall digestibility by hydrolytic enzymes have been described in the literature. Recently, researchers also found additional benefits by modifying the crystal structure of native cellulose (cellulose I) to cellulose III. After this modification, it was possible to significantly enhance the rate of enzymatic hydrolysis of cellulose by up to fivefold (Igarashi et. al., 2007). However, this increase was observed for purified cellulose from algae (Cellulose Iα), which has a different crystal configuration than cellulose from plants (Cellulose Iβ). Moreover, it is not evident that the cellulose within lignocellulosic plant biomass can so readily be converted to cellulose III or so readily processed to allow efficient enzyme digestion because lignin complicates the cellulose I to cellulose III conversion and reduces the enzyme digestibility of the material. Thus, the same kind of benefits observed for purified cellulose may not be observed for lignocellulosic plant biomass unless new processes are developed.

Therefore this Example explores the benefits of cellulose III conversion under non-anhydrous conditions, using corn stover as a source of lignocellulosic biomass, and coupling this modification with lignin extraction in a single stage process. These benefits were compared with a non-extractive ammonia based pretreatment method.

Extractive AFEX Apparatus

A reactor capable of performing lignin extraction at high temperatures and pressures was designed and constructed (FIG. 1B). This reactor consists of two major parts: 1) extraction cell and 2) extractives collector/separator. The extraction cell is used to react biomass with ammonia and solubilize the extractives that will be released from the biomass. These extractives generally consist of lignin, hemicellulose components, free sugars, phyto-chemicals, proteins, etc., whose compositions depend on the pretreatment solvents used. Once the reaction time is over, the extractives collector is set to the same pressure as the extraction cell using pressurized nitrogen and the valve between these two vessels is opened. Nitrogen overpressure is applied to prevent ammonia vaporization in the extraction cell and to drive the liquid phase to flow down to the extractives collector. An 80 micron filter placed in the bottom of the extraction cell prevents the solids from flowing down to the extractives collector. The valve that connects the extractive collector to the exhaust chamber is opened and the nitrogen/ammonia vapor flow is controlled to prevent rapid evaporation of ammonia in the extraction cell. After the extractives are all removed, the nitrogen overpressure valve is shut down and the gas is slowly released to the exhaust chamber until the system reaches atmospheric pressure. At this point, the pretreated biomass and the respective extractives can be removed from the system for further analysis.

Measuring Cellulose I to Cellulose III Conversion in Lignocellulosic Materials

While it is relatively easy to measure the amount of cellulose III formed from pure cellulose samples (e.g. AVICEL) that have no lignin using X-ray diffraction analyses, this is not true for lignocellulosic biomass because the lignin interferes with detection of peaks specific for cellulose. Thus, to measure the amount of cellulose III formed from lignocellulosic biomass one must deconvolute the X-ray diffraction spectrum or use a different detection procedure. However, both cellulose I and cellulose III have unique spectral peaks when measured by Raman spectroscopy that are distinct from the lignin Raman spectroscopy peaks. Thus, the conversion of cellulose I in corn stover biomass to cellulose III can be measured by Raman spectroscopy. Moreover, the amount of cellulose III formed as detected by Raman spectroscopy can be correlated with the amount detected by deconvolution of the X-ray diffraction data (see FIG. 10A). These results indicate that extent of conversion of cellulose III formed with corn stover can be accurately determined by either X-ray diffraction or Raman spectroscopy.

FIG. 10B shows a strong correlation between extent of cellulose III formation within corn stover and AVICEL for similar liquid ammonia pretreatment conditions. The pretreatment conditions involved treatment of Avicel or corn stover (i.e., the biomass) with 7:1 ammonia:biomass (wt.: wt.) for 2 hr at 25° C. As shown in FIG. 10B, cellulose III is formed when high levels of liquid ammonia are used for corn stover. Such cellulose III formation in the corn stover substrate also resulted in enhanced cellulose enzymatic hydrolysis.

Variables Affecting Glucan Formation in Lignocellulosic Materials

To verify the pretreatment reaction parameters that contribute significantly to the increase in glucan conversion within corn stover, as well as the parameters that contribute to xylan, arabinan and lignin loss during extraction, a factorial design of experiments was created using MINITAB® software (Minitab, Inc). A total of 18 different conditions were tested. The variable factors considered in this study include Temperature, Time, Liquid-to-Solid (L/S) ratio and Ammonia-to-Water (A/W) ratio during the extractive pretreatment. The dependent variables in this study were Glucan Conversion (G conversion), % Xylan loss, % Arabinan loss and % Lignin loss. Not all of the conditions tested can convert cellulose I to cellulose III, however the inventors wanted to determine the benefits of lignin extraction using ammonia-water solutions coupled with cellulose III conversion upon overall enzymatic digestibility.

The dependent variables determined from the experimental results were further used to fit a second order equation by MINITAB® software. The residual plots for each dependent variable show that the model fits reasonably well to the experimental data and that there is minimal error propagation. The ANOVA table that resulted from this model shows the statistically relevant parameters that influence the output of each dependent variable (Tables 2A-2D).

TABLE 2A

Estimated Effects and Coefficients for Glucan Conversion

| Term | Effect | Coef | SE Coef | T | P |
|---|---|---|---|---|---|
| Constant |  | 40.9501 | 0.5601 | 73.11 | 0.000 |
| Temperature | 21.3785 | 10.6892 | 0.5601 | 19.08 | 0.0001 |
| Time | 1.6513 | 0.8257 | 0.5601 | 1.47 | 0.191 |
| A/W | 3.1873 | 1.5936 | 0.5601 | 2.85 | 0.029 |
| L/S | 2.5629 | 1.2814 | 0.5601 | 2.29 | 0.062 |
| Temperature*time | 2.5352 | 1.2676 | 0.5601 | 2.26 | 0.064 |
| Temperature*A/W | 5.9555 | 2.9777 | 0.5601 | 5.32 | 0.002 |
| Temperature*L/S | 3.6161 | 1.8080 | 0.5601 | 3.23 | 0.018 |
| time*A/W | 0.0434 | 0.0217 | 0.5601 | 0.04 | 0.970 |
| time*L/S | 2.5787 | 1.2893 | 0.5601 | 2.30 | 0.061 |
| A/W*L/S | 1.5845 | 0.7922 | 0.5601 | 1.41 | 0.207 |
| Ct Pt |  | 2.4119 | 1.6804 | 1.44 | 0.201 |

S = 2.24050
R-Sq = 98.63%
PRESS = 301.288
R-Sq(pred) = 86.32%
R-Sq(adj) = 96.13%

TABLE 2B

Estimated Effects and Coefficients for % Lignin Loss

| Term | Effect | Coef | SE Coef | T | P |
|---|---|---|---|---|---|
| Constant |  | 0.198649 | 0.008553 | 23.23 | 0.000 |
| Temperature | 0.184388 | 0.092194 | 0.008553 | 10.78 | 0.000 |
| time | 0.040675 | 0.020337 | 0.008553 | 2.38 | 0.055 |
| A/W | 0.035146 | 0.017573 | 0.008553 | 2.05 | 0.086 |
| L/S | 0.090097 | 0.045048 | 0.008553 | 5.27 | 0.002 |
| Temperature*time | 0.047026 | 0.023513 | 0.008553 | 2.75 | 0.033 |
| Temperature*A/W | 0.000929 | 0.000465 | 0.008553 | 0.05 | 0.958 |
| Temperature*L/S | 0.049594 | 0.024797 | 0.008553 | 2.90 | 0.027 |
| time*A/W | 0.002886 | 0.001443 | 0.008553 | 0.17 | 0.872 |
| time*L/S | -0.002641 | -0.001321 | 0.008553 | -0.15 | 0.882 |
| A/W*L/S | 0.043870 | 0.021935 | 0.008553 | 2.56 | 0.043 |
| Ct Pt |  | 0.031540 | 0.025659 | 1.23 | 0.265 |

S = 0.0342119
R-Sq = 96.74%
PRESS = 0.0536059
R-Sq(pred) = 75.10%
R-Sq(adj) = 90.76%

TABLE 2C

Estimated Effects and Coefficients for % Arabinan Loss

| Term | Effect | Coef | SE Coef | T | P |
|---|---|---|---|---|---|
| Constant |  | 0.81381 | 0.008178 | 99.52 | 0.000 |
| Temperature | -0.04959 | -0.02480 | 0.008178 | -3.03 | 0.023 |
| time | 0.00956 | 0.00478 | 0.008178 | 0.58 | 0.580 |
| A/W | -0.01333 | -0.00667 | 0.008178 | -0.82 | 0.446 |
| L/S | -0.12461 | -0.06231 | 0.008178 | -7.62 | 0.000 |
| Temperature*time | -0.01916 | -0.00958 | 0.008178 | -1.17 | 0.286 |
| Temperature*A/W | 0.00911 | 0.00455 | 0.008178 | 0.56 | 0.598 |
| Temperature*L/S | -0.05361 | -0.02680 | 0.008178 | -3.28 | 0.017 |
| time*A/W | -0.01654 | -0.00827 | 0.008178 | -1.01 | 0.351 |
| time*L/S | -0.00364 | -0.00182 | 0.008178 | -0.22 | 0.831 |
| A/W*L/S | -0.02747 | -0.01373 | 0.008178 | -1.68 | 0.144 |
| Ct Pt |  | -0.02964 | 0.024534 | -1.21 | 0.272 |

S = 0.0327118
R-Sq = 93.48%
PRESS = 0.0486379
R-Sq(pred) = 50.61%
R-Sq(adj) = 81.53%

TABLE 2D

Estimated Effects and Coefficients for % Xylan Loss

| Term | Effect | Coef | SE Coef | T | P |
|---|---|---|---|---|---|
| Constant | | 0.013193 | 0.005247 | 2.51 | 0.046 |
| Temperature | 0.026880 | 0.013440 | 0.005247 | 2.56 | 0.043 |
| time | 0.014470 | 0.007235 | 0.005247 | 1.38 | 0.217 |
| A/W | −0.014698 | −0.007349 | 0.005247 | −1.40 | 0.211 |
| L/S | 0.058936 | 0.029468 | 0.005247 | 5.62 | 0.001 |
| Temperature*time | 0.046825 | 0.023413 | 0.005247 | 4.46 | 0.004 |
| Temperature*A/W | 0.006350 | 0.003175 | 0.005247 | 0.61 | 0.567 |
| Temperature*L/S | 0.027901 | 0.013951 | 0.005247 | 2.66 | 0.038 |
| time*A/W | −0.009929 | −0.004965 | 0.005247 | −0.95 | 0.381 |
| time*L/S | −0.016327 | −0.008164 | 0.005247 | −1.56 | 0.171 |
| A/W*L/S | −0.011007 | −0.005503 | 0.005247 | −1.05 | 0.335 |
| Ct Pt | | −0.004370 | 0.015742 | −0.28 | 0.791 |

S = 0.0209896
R-Sq = 92.48%
PRESS = 0.0267071
R-Sq(pred) = 24.03%
R-Sq(adj) = 78.69

These results show that temperature is a statistically relevant parameter for all the dependent variables tested. Liquid-to-solid ratio (L/S) is also a relevant variable for maximizing the extraction of Lignin, Arabinan and Xylan. The variable time was not highly relevance to any of the dependent variables where the range of times analyzed was between 20 and 45 minutes. The data indicate the pretreatment can be likely performed at lower residence times without compromising any of the dependent variable results. The data further indicate that the variable ammonia:water (A/W) may be important for achieving good glucan conversion.

As shown by FIG. 11, removal of lignin significantly improved the conversion of cellulose to useable glucans. In general, glucan conversion increased as the amount of lignin loss from the biomass increases (FIG. 11). However, lignin loss was not the only factor contributing to biomass recalcitrance. Thus, the $R^2$ value for lignin loss and glucan conversion was only 0.7489.

In one of the tested conditions, liquid ammonia was contacted with biomass without any adding moisture. In this case, only residual moisture from the biomass was present during pretreatment (close to 6.5% moisture) (Table 3).

TABLE 3

AFEX and Extractive-Ammonia Treatment conditions

| | AFEX (Cellulose I) | Extractive Ammonia (Cellulose III) |
|---|---|---|
| Temperature | 130° C. | 100° C. |
| Time | 15 min | 45 min |
| Ammonia to biomass ratio | 1:1 | 7.5:1 |
| Ammonia to water ratio | 1.7:1 | 50:1 |

Studies indicate that cellulose III is most likely to form using the Extractive-Ammonia conditions listed in Table 3. Therefore the Extractive-Ammonia sample was analyzed in more detail and compared with regular non-extractive AFEX.

FIG. 12 shows that about 73% of the Arabinan was removed by the extraction procedure performed during Extractive-Ammonia. While only 1.8% of total xylan was extracted by ammonia, about 34.3% of the acid-insoluble lignin was removed using the Extractive-Ammonia pretreatment. Note that only the acid insoluble lignin was measured in this study, and that the acid soluble lignin was not determined. If the acid soluble lignin had also been determined, a greater total lignin loss would likely have been detected in the extract. Thus, the extraction procedure was highly effective for removal of Arabinan and quite effective for removal of lignin. But most of the glucan remained in the biomass residue and was not extracted. As shown in FIG. 12, only 6.3% of the glucan was extracted, indicating that over 93% of the glucan remained in the residue. These data indicate that that ammonia is selective in extracting only certain plant cell wall components.

The digestibility of extractive ammonia-pretreated corn stover was compared with conventional AFEX treatment of corn stover, liquid ammonia-extraction treated corn stover, Avicel (Cellulose I), and Avicel (Cellulose III). The conventional AFEX conditions employed were 1:1 ammonia to biomass (wt.:wt.) with 0.6:1 water:biomass (wt.:wt.) for 15 min. at 130° C. Avicel (Cellulose I) was untreated Avicel. For liquid ammonia-treatment, corn stover was treated with 7.5:1 ammonia:biomass (wt.:wt.) for 45 minutes at 100° C. The liquid ammonia-treated corn stover was also extracted as described above. Avicel (Cellulose III) was prepared by treating Avicel with 7:1 ammonia to biomass loading at 25° C. for 30 min. For these studies, 15 mg of Accelerase 1500 (Genencor-Danisco) cellulase per gram of glucan was incubated with the variously treated cellulose materials at 50° C. with stirring at 250 RPM for 12, 24 and 72 hours.

FIG. 13 shows that after 24 h digestion the biomass treated with extractive ammonia pretreatment has a 1.7 times higher rate of enzymatic hydrolysis than biomass treated with conventional AFEX. The extractive ammonia pretreated corn stover also shows higher glucan conversion than purified cellulose I (Avicel). The inclusion of xylanases and other accessory hemicellulases in the enzyme cocktail is expected to further increase the glucan conversion so that the glucan conversion of biomass (e.g., corn stover) after extractive ammonia pretreatment generates even higher conversions (similar to those seen with ammonia treatment of Avicel).

Surprisingly, extractive ammonia pretreatment proceeds effectively even when significant water is present during ammonia treatment (Table 4).

TABLE 4

Pretreatment conditions for high glucan conversions in corn stover

| Condition | Temperature (° C.) | Time (min) | A/W | L/S | Glucan Conversion | Lignin Loss |
|---|---|---|---|---|---|---|
| 1 | 120 | 45 | 5 | 8 | 65.77% | 46.27% |
| 2 | 100 | 45 | 50 | 8 | 64.31% | 34.31% |

A/W = ammonia:water; L/S = liquid:solid.

As shown in Table 4, Condition #1 had a lower ammonia:water ratio but still showed higher glucan conversion and greater lignin removal. Thus some water can be present in the liquid ammonia treatment. Note also that condition #2 corresponds to the same conditions used to produce cellulose III that were shown in Table 3.

In condition #1 about 80% ammonia in water was used, with a 8:1 Liquid-to-Solid ratio, and the biomass was incubated in this solution at 120° C. for 45 minutes. Under these conditions a 65.8% glucan conversion was observed after 72 h. In contrast, the same conditions used with Avicel (cellulose I) gave rise to only 55% glucan conversion. Thus, cellulose I in corn stover was converted to significant amounts of cellulose III using 80% ammonia by the Extractive-Ammonia pretreatment procedure. This is surprising because significant data indicate that only anhydrous ammonia is capable of converting cellulose I to cellulose III.

However, the Extractive-Ammonia pretreatment removes significant amounts of lignin, which may contribute to the higher conversion of corn stover cellulose I for cellulose III control.

High-solid loading based enzymatic hydrolysis experiments were performed using cellulose I-rich and cellulose III-rich pretreated corn stover at two different cellulase loadings. The biomass was corn stover. The cellulose I-rich corn stover was generated by treatment of corn stover with 1:1 ammonia to biomass (wt.:wt.) with 0.6:1 water:biomass (wt.:wt.) for 15 min. at 130° C. The cellulose III rich corn stover was generated by treatment of corn stover with 7:1 ammonia:biomass (wt.:wt.) for 2 hr at 100° C., where the biomass had residual moisture of 0.05 water g gram biomass. As shown in FIG. 14A-D, it is possible to achieve higher glucan conversions at lower total cellulase loading with industrially relevant solids loading of cellulose III-rich substrates. This study indicates that equivalent conversions can be achieved for cellulose III at 3-fold lower cellulase loading than is needed for cellulose I, even when industrially relevant high loadings are present. Also, the inventors find that the glucan and xylan conversions for cellulose III-rich pretreated corn stover are not influenced by solids loading as it is for cellulose I-rich pretreated corn stover conferring additional advantages during enzymatic hydrolysis under industrially relevant high-solids loading conditions.

Cellulose III-rich pretreated corn stover was generated by treatment with 7:1 ammonia:biomass (wt.:wt.) for 2 hr at 100° C., where the biomass had residual moisture of 0.05 water g gram biomass. No extraction of plant wall components was performed. The enzyme mixture needed to optimally convert this cellulose III rich AFEX corn stover was evaluated by varying the amount and types of enzymes employed for enzymatic digestion as shown in Table 5.

TABLE 5

Enzyme Mixtures for Hydrolysis of cellulose III rich AFEX corn stover

| Enzyme mixture | Acellerase 1500 | Multifect xylanase | Multifect pectinase |
| --- | --- | --- | --- |
| 1 | 100% | | |
| 2 | | 100% | |
| 3 | | | 100% |
| 4 | 50% | 50% | |
| 5 | 50% | | 50% |
| 6 | | 50% | 50% |
| 7 | 33.3% | 33.3% | 33.3% |
| 8 | 67% | 16% | 17% |
| 9 | 16% | 67% | 17% |
| 10 | 16% | 17% | 67% |

In each case 30 mg total enzyme was used with hydrolysis for 24 hours.

The results are shown in FIG. 15. In general, the highest levels of glucan and xylan from non-extracted cellulose III rich AFEX corn stover were obtained when combinations of enzymes were used. Thus, when equivalent amounts of Acellerase 1500, Multifect xylanase and Multifect pectinase were used (enzyme mixture 7), high levels of both glucan and xylan were released from the corn stover substrate.

Example 5

Endocellulases Augment Cellulose III Digestion

This Example describes experimental results illustrating the types of enzymes that optimally digest cellulose allomorphs.

Two exocellulases, Cel7A (Cellobiohydrolase I or CBH I) and Cel6A (CBH II), and an endocellulase, Cel7B (EG I), from *Trichoderma reesei* were used in varying combinations to hydrolyze cellulose I and III, derived from Avicel, Cotton fibers and linters. Cellulose I is untreated pure cellulose (Avicel, Linters or cotton fibers). To generate cellulose I in these cellulose biomass materials, the biomass was treated with 7:1 ammonia:biomass (wt.:wt.) with for 30 min. at 95° C.

Purified cellulases were used to hydrolyze these celluloses for 24 h and the yield of hydrolyzed soluble glucans (e.g., glucose) was recorded. Each purified enzyme was loaded at 2.5 mg/each and additional beta-glucosidase (10% of total cellulase added) was supplemented in each assay to prevent inhibition by cellobiose. Standard deviations were within ±20% of the reported mean values. However, no significant improvement in specific activity for any of the cellulases was seen when added alone to cellulose III derived from Avicel, or linters and cotton fibers (FIG. 16). Interestingly, the most significant enhancement in the hydrolysis yield for cellulose III versus cellulose I occurred when combinations of exocellulases and endocellulases were employed. Thus, the combination of Cel7A+Cel6A+Cel7B was particularly effective (FIG. 16).

Other enzymes were tested, including combinations of Cel7A, Cel6A, Cel7B, Cel5A_ac, Cel5A_tr, Cel12A, Cel61A, and Cel61B. Cellulases Cel5A_tr, Cel12A, Cel61A and Cel61B are from *T. reesei* and Cel5A_ac is from *Acidothermus cellulolyticum*.

The degree of synergistic effect (DSE) for enzyme combinations was noted, where the degree of synergistic effect (DSE) is defined as follows.

$$\text{Degree of Synergy } (DSE_\zeta) = \frac{\zeta_{i-mix}}{\Sigma \zeta_i}$$

where $\zeta_{i-max}$ is the extent of glucan conversion achieved by a mixture of proteins;

$\zeta_i$ is the extent of glucan conversion achieved by the $i^{th}$ single protein component.

As shown in the Table 6 below, a single enzyme occasionally had slightly better activity on cellulose I than on cellulose III but combinations of enzymes typically digested significantly more cellulose III than cellulose I. Thus, there was a marginal decrease in hydrolytic yield noticed for individual exocellulases (Cel7A, Cel6A) on cellulose III as compared to cellulose I. However, in general, fairly similar glucan conversions were observed for the two substrates when a single enzyme was employed. For binary exocellulase mixtures, glucan conversions for cellulose I and III substrates rarely exceeded 10%. However, somewhat improved glucan conversion was observed when certain exocellulase+endocellulase combinations were employed.

TABLE 6

| Cellulase Combination | Cellulose $I_\beta$ | Cellulose $III_I$ |
|---|---|---|
| Cel7A | 3.8 | 1.6 |
| Cel6A | 3.0 | 1.7 |
| Cel7B | 2.6 | 3.7 |
| Cel 5A_tr | 1.9 | 1.9 |
| Cel61A | 0.9 | 1.0 |
| Cel61B | 0.6 | 0.7 |
| Cel5A_ac | 3.4 | 2.7 |
| Cel12A | 1.8 | 1.8 |
| Cel7A + Cel7B | 16.0 | 23.7 |
| Cel7A + Cel5A_tr | 7.8 | 8.2 |
| Cel7A + Cel61A | 6.4 | 3.7 |
| Cel7A + Cel61B | 4.8 | 3.3 |
| Cel7A + Cel5A_ac | 12.6 | 9.1 |
| Cel7A + Cel12A | 11.7 | 7.9 |
| Cel7A + Cel6A | 12.1 | 11.8 |
| Cel6A + Cel7B | 9.2 | 11.4 |
| Cel6A + Cel5A_tr | 6.8 | 4.5 |
| Cel6A + Cel61A | 3.4 | 2.9 |
| Cel6A + Cel61B | 3.8 | 2.5 |
| Cel6A + Cel5A_ac | 9.3 | 8.6 |
| Cel6A + Cel12A | 6.0 | 5.0 |
| Cel7A + Cel6A + Cel7B | 31.3 | 68.9 |
| Cel7A + Cel6A + Cel5A_tr | 21.7 | 30.4 |
| Cel7A + Cel6A + Cel61A | 13.3 | 16.7 |
| Cel7A + Cel6A + Cel61B | 13.8 | 14.6 |
| Cel7A + Cel6A + Cel5A_ac | 20.4 | 25.7 |
| Cel7A + Cel6A + Cel12A | 18.9 | 19.4 |

However, for ternary cellulase combinations most mixtures resulted in glucan conversions ranging between 10-30% and 15-70% for cellulose I and III, respectively. The GH family 5 and 7 endocellulases generally resulted in significantly higher conversions for cellulose III (>25% increase in hydrolysis yield with respect to control) compared to other endocellulase families (e.g., GH 12, 61). Thus, as indicated by the Table 6 above, the highest glucan conversion was seen for an equimass ternary combination of Cel7A/Cel6A/Cel7B. Further studies indicated that the optimal ratio of Cel7A/Cel6A/Cel7B (15 mg/g glucan total enzyme loading) for maximizing the 24 hr yield of hydrolyzed Avicel derived cellulose I and III had a marginally higher percentage of Cel7B (35 wt % Cel7B vs 32 wt % of the other cellulase proteins; mixture optimization data not shown).

The influence of endocellulase type on the degree of synergistic effect (DSE) with exocellulases Cel7A+Cel6A was also studied during hydrolysis of crystalline cellulose I and III. Cellulose I is untreated pure cellulose (Avicel, Linters or cotton fibers). To generate cellulose III in these cellulose biomass materials, the biomass was treated with 7:1 ammonia:biomass (wt.:wt.) for 30 min at 95° C.

The endocellulases from homologous and distinct glycosyl hydrolase (GH) families that were tested in combination with Cel7A and Cel6A included Cel5A_ac from *Acidothermus cellulolyticus*, Cel5A_tr from *T. reesei* and Cel7B (EG I) from *Trichoderma reesei*. The cellulose I and III substrates were derived from Avicel. In general, cellulose III was digested to a greater extent than cellulose I when combinations of exocellulases and endocellulases were employed. Thus, the binary DSE for Cel7A/Cel6A and Cel7A/Cel7B was 1.7 and 2.5 on cellulose I compared to 3.5 and 4.4 observed on cellulose III, respectively. However, as indicated by FIG. 17, there was a 30-100% and 40-370% increase in the cellulose I and cellulose III DSEs, respectively, when endocellulases were used with the two exocellulases Cel7A+Cel6A.

Cel7A, Cel6A and Cel7B are the most abundant *T. reesei* cellulases and provide efficient cellulose hydrolysis as indicated above. Thus, these enzymes are ideal candidates for detailed enzyme binding studies. Enzyme-substrate binding affinity was experimentally determined by fitting a Langmuir single-site adsorption model to the *T. reesei* Cel7A, Cel6A and Cel7B binding isotherms for Avicel derived cellulose I and III. Cellulose I and cellulose III were mixed with 50 mg cellulose enzyme per gram of glucan and incubated at 4° C. to adsorption equilibrium. The cellulose enzymes tested were Cel7A (Cellobiohydrolase I or CBH I), Cel6A (CBH II), and endocellulase Cel7B (EG I).

Surprisingly, all three cellulases showed a reduced overall maximum binding affinity for cellulose III compared to native cellulose (based on maximum binding affinity coefficient; mg protein/g substrate). As indicated in Table 7 below, the binding to cellulose III was about 50-70% less than to cellulose I.

TABLE 7

| | Approximate % Enzyme bound to Cellulose | | |
|---|---|---|---|
| | CBHI (Cel7A) | CBHII (Cel6A) | EGI (Cel7B) |
| Cellulose I | 97% | 54% | 75% |
| Cellulose III | 29% | 27% | 35% |

This is in contrast to what has been reported in literature previously. In particular, previous studies indicate that the enzymatic hydrolysis rate is directly correlated with the extent of enzyme adsorbed to cellulose (Hall et al., FEBS Journal 277: 1571-82 (2010); Canard et al., PNAS 97: 10342-47 (2000)). In fact, the enzyme-substrate binding affinity data obtained by the inventors indicate that there is reduced cellulase binding to the more readily digestible cellulose III allomorph. All three major *Trichoderma* cellulases exhibited similar binding capacities for each of the cellulose allomorphs analyzed in the study (Cel7A\Cel7B>Cel6A), and their overall binding capacities were 2-3 fold greater for cellulose I than for cellulose III. The maximum surface bound cellulase capacity for cellulose III was 50-70% lower compared to native cellulose I.

Thus, the improved hydrolytic activity on the cellulose III substrate that was observed as described above (e.g., in Table 6 and FIGS. 16-17) cannot be explained in terms of the binding capacities of cellulases for cellulose I and cellulose III. Previous studies have shown that *T. reesei* cellulases preferentially bind to the axial cellulose I crystal surface through van der Waals and aromatic ring polarization interactions involving the aromatic residues of the cellulose binding modules (CBMs) and the pyranose rings (Lehtio et al., Proc. Nat'l Acad. Sci. USA 100(2): 484-489 (2003)). Most *T. reesei* cellulases are comprised of highly homologous family 1 CBMs, which generally have similar binding affinities for each cellulose allomorph. Recent molecular dynamics (MD) simulation studies have shown that family 1 cellulose binding modules have greater affinity for the hydrophobic face of cellulose I compared to its relatively more hydrophilic surfaces (Yui et al., J. Phys. Chem. B114 (1): 49-58 (2009)). Some reports indicate that the binding of cellulases to native cellulose is driven via the interaction of aromatic planar residues found in family 1 CBMs, but the processivity of cellulases may be driven via hydrogen bonding (Beckham et al., J. Phys. Chem. 114: 1447-53 (2010)).

The inventors have conducted molecular dynamic structural analysis of cellulose I and cellulose III, and have observed that cellulose III undergoes greater intra-sheet thermal fluctuation than does cellulose I. Thus, cellulose III also has a greater radius of gyration ($Rg^2$) than cellulose I.

TABLE 8

Crystalline Fiber Thermal Fluctuations

|  | Inter-sheet | Intra-sheet | Chain axis | $Rg^2$ |
|---|---|---|---|---|
| Cellulose $I_\beta$ | 3.3 | 1.1 | 1.1 | 336.2 |
| Cellulose $III_I$ | 3.2 | 1.63 | 1.1 | 343.2 |

Thus, the increased tendency for cellulose III crystal structure to allow hydrogen bonds with water molecules for surface-exposed glucan chains may facilitate enzyme interaction and enzyme processivity (and hence increased cellulase efficiency) despite the reduced overall cellulase binding capacity.

In addition to the structural and molecular properties of cellulose III and cellulose binding modules, the interaction of the catalytic domain of an enzyme through its active site cleft also plays a role. The inventors have found that the degree of synergistic activity (DSE) on cellulose III for an endocellulase-exocellulase mixture comprising of Cel7B was at least two times greater than mixtures comprising glycosyl hydrolase family 5 endocellulases (Cel5A_ac and Cel5A_tr). The comparison of the active site clefts of these enzymes reveals that Cel7B has a long and relatively unrestricted active site cleft compared to that of Cel5A. This open active site cleft of Cel7B plays a significant role in providing an easily accessible platform for productive binding and efficient catalysis. Accordingly, Cel61A has no discernable open active site cleft and shows minimal improvement in DSE on cellulose III. Based on the protein structures and activity assays, it appears that a cellulase such as Cel7B with a more open and unrestricted active site cleft may further accelerate the degradation of cellulose III compared to other endocellulases. Furthermore, it is likely that the energetic barrier to cellulose decrystallization by endocellulases is higher than exocellulases because threading by processive enzymes should additionally contribute to lowering the thermodynamic barrier to decrystallization. This further emphasizes the importance of altering the cellulose crystal structure (from I to III), to reduce the decrystallization barrier and improve the kinetics of cellulose hydrolysis.

Example 6

Extractive Pretreatment with Ammonia and Acetone

This Example describes the impact of using acetone as solvent on the formation of cellulose III during pretreatment of biomass with ammonia. Reversion of cellulose III to cellulose I occurs if water is used as a solvent in high concentrations. Thus, such reversion may be avoided by employing other types of solvents.

Anhydrous liquid ammonia pretreatment was performed as described in Example 1 except that substantial acetone was added to ascertain whether such acetone affects the formation of cellulose III. In particular, 0.2-0.3 g biomass was treated with 11 ml of 1:10 ammonia to acetone (vol.: vol.) for varying time periods at 25° C. The time of pretreatment for the samples was 2.5, 7.5, 10 and 60 minutes. The formation cellulose III was monitored by X-ray diffraction analysis.

Acetone did not adversely affect formation of cellulose III. In fact, as shown in FIG. 18, substantially complete conversion of cellulose I to cellulose III was observed after just 2.5 minutes pretreatment of Avicel with the anhydrous liquid ammonia:acetone mixture.

These results indicate that acetone can be used as a co-solvent during liquid ammonia treatment to expedite the formation of cellulose III and the extraction of lignin from the lignocellulosic biomass in a selective manner.

Example 7

Fermentation of Cellulose III-Rich Corn Stover

This example shows that cellulose III-rich corn stover is readily fermented to generate significant amounts of ethanol.

The biomass employed was corn stover. Cellulose III rich corn stover was generated by treatment of corn stover with 7:1 ammonia:biomass (wt.:wt.) for 2 hr at 100° C., where the biomass had residual moisture of 0.1 water g gram biomass.

The enzymatic hydrolysis was performed on the treated corn stover samples as described in Example 4 (see data shown in FIG. 14). The pretreated corn stover was enzymatically hydrolyzed using high solids loading at two enzyme levels: low (15 mg/g glucan) and high (30 mg/g glucan) cellulase loading. Hydrolysis was carried out for 168 hr.

Fermentation was carried out at 30° C., pH 5.5, using 0.2 initial cell optical density (OD) with stirring at 150 rpm. No exogenous nutrients were added to support cell growth other than the substrate: 6% glucan loading based hydrolyzate of cellulose III rich corn stover. No plant wall components were extracted from this substrate. Two enzyme loadings were used to carry out hydrolysis: 15 mg per g glucan (square symbol) and 30 mg per g glucan (diamond symbol). Fermentation was for 120 hr.

As shown in FIG. 19, close to 40 g/L ethanol was produced, which is an ethanol concentration appropriate of industrial scale distillation of the final product. Moreover, fermentation of the cellulose III-rich corn stover was just as efficient when enzyme digestion was performed with 15 mg per g glucan as with 30 mg per g glucan. In contrast, enzyme digestion of cellulose I-containing AFEX corn stover was less efficient (FIG. 14). Thus, less enzyme can be used to efficiently digest the cellulose III-rich biomass and permit significant levels of ethanol to be produced during fermentation.

REFERENCES

All publications, patents and patent documents are incorporated by reference herein, each in their entirety, as though individually incorporated by reference. In the case of any inconsistencies, the present disclosure, including any definitions therein, will prevail.

1. Zhang, Y.-H. P. et al., Fractionating recalcitrant lignocellulose at modest reaction conditions. *Biotechnology and Bioengineering* 97 (2), 214-223 (2007).
2. Zhang, Y. H. P., Cui, J., Lynd, L. R., & Kuang, L. R., A Transition from Cellulose Swelling to Cellulose Dissolution by o-Phosphoric Acid: Evidence from Enzymatic Hydrolysis and Supramolecular Structure. *Biomacromolecules* 7 (2), 644-648 (2006).
3. Swatloski, R. P., Spear, S. K., Holbrey, J. D., & Rogers, R. D., Dissolution of cellulose with ionic liquids. *Journal of the American Chemical Society* 124 (18), 4974-4975 (2002).
4. Chundawat, S., 2009. Ultrastructural and physicochemical modifications within ammonia treated lignocellulosic cell walls and their influence on enzymatic digestibility Chemical Engineering & Materials Science. Ph.D. Dissertation. Michigan State University, East Lansing.

5. Pan, X. J., Role of functional groups in lignin inhibition of enzymatic hydrolysis of cellulose to glucose. *J. Biobased Mater. Bioenergy* 2 (1), 25-32 (2008).

6. Klinke, H. B., Thomsen, A. B., & Ahring, B K, Inhibition of ethanol-producing yeast and bacteria by degradation products produced during pre-treatment of biomass. *Applied Microbiology and Biotechnology* 66 (1), 10-26 (2004).

7. Lau, M. W. & Dale, B. E., Cellulosic ethanol production from AFEX-treated corn stover using *Saccharomyces cerevisiae* 424A(LNH-ST). *Proceedings of the National Academy of Sciences* 106 (5), 1368-1373 (2009).

8. Chundawat, S. P. S., Vismeh, R., Sharma, L., Humpula, J., Sousa, L., Chambliss, C. K., Jones, A. D., Balan, V., Dale, B. E., 2010. Multifaceted characterization of cell wall decomposition products formed during ammonia fiber expansion (AFEX) and dilute-acid based pretreatments. *Biores Technol*, 101, 8429-8438.

9. Carolan, J., Joshi, S., & Dale, B., Technical and Financial Feasibility Analysis of Distributed Bioprocessing Using Regional Biomass Pre-Processing Centers. *J Agri Food Ind Org* 5, 10 (2007).

10. Aden, A., et al., *Lignocellulosic Biomass to Ethanol Process Design and Economics Utilizing Co-Current Dilute Acid Prehydrolysis and Enzymatic Hydrolysis for Corn Stover*, in Technical Report. 2002, National Renewable Energy Laboratory (NREL): Golden. p. 1-154.

11. Schell, D. J., et al., *Dilute-sulfuric acid pretreatment of corn stover in pilot-scale reactor: Investigation of yields, kinetics, and enzymatic digestibilities of solids*. Applied Biochemistry and Biotechnology, 2003. 105(1-3): p. 69-85.

12. Wyman, C., et al. *Comparative Data for Enzymatic Digestion of Corn Stover and Poplar Wood after Pretreatment by Leading Technologies*. in AIChE Annual Meeting. 2006. San Francisco, Calif.

13. Wyman, C. E., *Integration of Leading Biomass Pretreatment Technologies with Enzymatic Digestion and Hydrolyzate Fermentation*. 2005, Department of Energy. p. 1-10.

14. Mohagheghi, A., et al., *High Solids Simultaneous Saccharification and Fermentation of Pretreated Wheat Straw to Ethanol*. Appl Biochem Biotechnol, 1992. 33: p. 67-81.

15. Eggeman, T. and R. T. Elander, *Process and economic analysis of pretreatment technologies*. Bioresource Technology, 2005. 96(18): p. 2019-2025.

16. Varga, E., K. Réczey, and G. Zacchi, *Optimization of steam pretreatment of corn stover to enhance enzymatic digestibility*. Applied Biochemistry and Biotechnology, 2004. 114(1-3): p. 509-523.

17. Playne, M. J., *Increased digestibility of bagasses by pretreatment with alkalis and steam explosion*. Biotechnology and Bioengineering, 1984. 26(5): p. 426-433.

18. Mackie, K. L., et al., *Effect of Sulfur Dioxide and Sulfuric Acid on Steam Explosion of Aspenwood*. Journal of Wood Chemistry and Technology, 1985. 5(3): p. 405-425.

19. Ballesteros, I., et al., *Ethanol production from steam-explosion pretreated wheat straw*. Applied Biochemistry and Biotechnology, 2006. 130(1-3): p. 496-508.

20. Hongzhang, C. and L. Liying, *Unpolluted fractionation of wheat straw by steam explosion and ethanol extraction*. Bioresource Technology, 2007. 98(3): p. 666-676.

21. Balan, V., et al., *Enzymatic digestibility and pretreatment degradation products of AFEX-treated hardwoods (<I>Populus nigra</I>)*. Biotechnology Progress, 2009. 25(2): p. 365-375.

22. Yoon, H. H., Z. W. Wu, and Y. Y. Lee, *Ammonia-Recycled Percolation Process for Pretreatment of Biomass Feedstock*. Applied Biochemistry and Biotechnology, 1995. 51-52(1): p. 5-19.

23. Kim, T. H. and Y. Y. Lee, *Pretreatment and fractionation of corn stover by ammonia recycle percolation process*. Bioresource Technology, 2005. 96(18): p. 2007-2013.

24. Kim, T. H., et al., *Pretreatment of corn stover by low-liquid ammonia recycle percolation process*. Applied Biochemistry and Biotechnology, 2006. 133(1): p. 41-57.

25. Ishizawa, C., et al., *Porosity and Its Effect on the Digestibility of Dilute Sulfuric Acid Pretreated Corn Stover*. J Agric Food Chem 2007. 55: p. 2575-2581.

26. Davis, M. F., et al., *Chemical and Physical Properties of Pretreated Biomass that Affect Enzyme Accessibility and Digestibility*, in Agricultural Biomass, Biobased Products, and Biofuels. 2007: Chicago, Ill.

27. Igarashi, K., M. Wada, and M. Samejima, *Activation of crystalline cellulose to cellulose III results in efficient hydrolysis by cellobiohydrolase*. FEBS Journal, 2007. 274 (7): p. 1785-1792.

28. Weimer P J, French A D, Calamari T A. *Differential Fermentation of Cellulose Allomorphs by Ruminal Cellulolytic Bacteria*. Appl Environ Microbiol. 1991 57(11): 3101-3106.

29. Sendich, E., et al., *Recent process improvements for the ammonia fiber expansion (AFEX) process and resulting reductions in minimum ethanol selling price*. Bioresource Technology, 2008. 99(17): p. 8429-8435.

30. da Costa Sousa, L., et al., *'Cradle-to-grave' assessment of existing lignocellulose pretreatment technologies*. Current Opinion in Biotechnology, 2009. 20(3): p. 339-347.

31. Igarashi K, Wada M, Samejima M. 2007. Activation of crystalline cellulose to cellulose III results in efficient hydrolysis by cellobiohydrolase. FEBS Journal 274 (7): 1785-1792.

32. Chundawat S. 2009. Ultrastructural and physicochemical modifications within ammonia treated lignocellulosic cell walls and their influence on enzymatic digestibility. East Lansing: Michigan State University (Ph.D. Dissertation; AAT 3417644).

33. Chundawat S P S, Bellesia G, Uppugundla N, Sousa L, Gao D, Cheh A, Agarwal U, Bianchetti C, Phillips G, Langan P, Balan V, Gnanakaran S, Dale B E. Restructuring crystalline cellulose hydrogen bond network enhances its depolymerization rate. Manuscript under review (2011).

34. Wada M, Chanzy H, Nishiyama Y, Langan P. 2004. Cellulose IIII crystal structure and hydrogen bonding by synchrotron X-ray and neutron fiber diffraction. Macromolecules 37(23):8548-8555.

35. Barry A J, Peterson F C, King A J. 1936. X-Ray Studies of Reactions of Cellulose in Non-Aqueous Systems. I. Interaction of Cellulose and Liquid Ammonia. Journal of the American Chemical Society 58(2):333-337.

36. Lewin M, Roldan L G. 1971. The Effect of Liquid Anhydrous Ammonia in the Structure and Morphology of Cotton Cellulose. Journal of Polymer Science Part C-Polymer Symposium(36):213-229.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a microorganism" includes a plurality (for example, a culture or population) of such microorganisms. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, the phrase "consisting essentially of" or "consisting of" can be used in place of the term "comprising" within the claims. Where features or aspects of the invention are described in terms of Markush groups, those skilled in the art will recognize that the invention is also thereby described in terms of any individual member or subgroup of members of the Markush group.

What is claimed is:

1. A method for producing an extracted product from lignocellulosic biomass comprising:

completely converting native cellulose $I_\beta$ to cellulose $III_I$ by pretreating the lignocellulosic biomass with anhydrous liquid ammonia or liquid ammonia comprising a solution of at least 80% ammonia at a temperature from about 50° C. to about 140° C. and at atmospheric pressure or higher to generate a pretreated lignocellulosic biomass, wherein the lignocellulosic biomass has a moisture content of less than 20% and a weight ratio of liquid ammonia to lignocellulosic biomass is 3:1 to 8:1, wherein the pretreated lignocellulosic biomass contains lignin and/or hemicellulose; and extracting at least a portion of the lignin and/or hemicellulose from said pretreated lignocellulosic biomass to produce said extracted product and a pretreated biomass product, wherein said extracted product contains said lignin and/or hemicellulose.

2. The method of claim 1, wherein the solution further comprises a solvent.

3. The method of claim 2, wherein the solvent is water or an organic solvent.

4. The method of claim 3, wherein the organic solvent is selected from acetone, ethanol, methanol, isopropanol, dichloromethane, methyl acetate, ethyl acetate, chloroform and combinations thereof.

5. The method of claim 1, wherein the lignocellulosic biomass is pretreated with the liquid ammonia for 1 minute to 3 hours.

6. The method of claim 1, wherein the temperature is from about 50° C. to about 120° C.

7. The method of claim 1, wherein the lignin is one of a plurality of plant cell wall components which are extracted in the extracting step.

8. The method of claim 7, wherein said plant cell wall components further include hemicellulose, arabinan, and combinations and degradation products thereof.

9. The method of claim 1, wherein glucan and xylan are retained with the pretreated biomass.

10. The method of claim 1, wherein the extracting step is performed simultaneously with the anhydrous liquid ammonia pretreatment.

11. The method of claim 1, wherein the extracting step is performed after the anhydrous liquid ammonia pretreatment.

12. The method of claim 1, further comprising digesting the pretreated biomass with a combination of enzymes.

13. The method of claim 12, wherein the combination of enzymes comprises at least one exocellulase, at least one endocellulase and/or beta-glucosidase.

14. The method of claim 13, wherein the combination of enzymes comprises Cel7A (Cellobiohydrolase I), Cel6A (Cellobiohydrolase II) and Cel7B (EG I), each of which are from *Trichoderma* (*T.*) *reesei*.

15. The method of claim 14, wherein the combination of enzymes further comprises Cel5A_tr, from *T. reesei*, Cel5A_ac from *Acidothermus cellulolyticum*, or a combination thereof.

16. The method of claim 15, wherein the combination of enzymes further comprises cellulase Cel12A, Cel61A, or Cel61B, each of which are from *T. reesei* or a combination thereof.

17. The method of claim 1, further comprising an enzymatic hydrolysis step to hydrolyze the pretreated biomass product, wherein said enzymatic hydrolysis step proceeds at a rate that is at least 1.5 times faster than a hydrolysis step performed using plant biomass that has not been pretreated with the liquid ammonia.

18. The method of claim 1, further comprising recycling the liquid ammonia in a batch mode, a semi-batch mode or continuously.

19. The method of claim 1, further comprising reusing the liquid ammonia to pretreat another batch of lignocellulosic biomass.

20. The method of claim 2, further comprising recycling the solvent in a batch mode, a semi-batch mode or continuously.

21. The method of claim 2, further comprising reusing the solvent to pretreat another batch of lignocellulosic biomass.

22. The method of claim 1, wherein the product is a biofuel.

23. The method of claim 1, wherein the extracted product is converted to a bioproduct comprising a resin, a polymer, a biofuel, a biochemical, heat and/or electricity.

24. The method of claim 1, wherein the liquid ammonia is combined with acetone.

25. The method of claim 24, wherein the liquid ammonia to acetone volume:volume ratio ranges from 10:90 to 99:1.

26. A method for producing a digested product from lignocellulosic biomass comprising:

completely converting native cellulose $I_\beta$ to cellulose $III_I$ by pretreating the lignocellulosic biomass with anhydrous liquid ammonia or liquid ammonia comprising a solution of at least 80% ammonia at a temperature from about 50° C. to about 140° C. and at atmospheric pressure or higher to generate a pretreated biomass, wherein the lignocellulosic biomass has a moisture content less than 20% and a weight ratio of liquid ammonia to lignocellulosic biomass is 3:1 to 8:1, wherein the pretreated lignocellulosic biomass contains lignin and/or hemicellulose; and digesting the pretreated biomass with a combination of enzymes to produce fermentable sugars, wherein the combination of enzymes comprises at least one exocellulase, at least one endocellulase and/or beta-glucosidase.

27. The method of claim 1 wherein the pretreated biomass product comprises a cellulose-rich solids fraction and a liquid fraction.

28. The method of claim 27 wherein the plant biomass also contains hemicellulose and the cellulose rich solids fraction in the pretreated biomass product is separated from the hemicellulose and the lignin.

* * * * *

UNITED STATES PATENT AND TRADEMARK OFFICE
CERTIFICATE OF CORRECTION

PATENT NO. : 9,650,657 B2
APPLICATION NO. : 13/642052
DATED : May 16, 2017
INVENTOR(S) : Shishir Chundawat et al.

It is certified that error appears in the above-identified patent and that said Letters Patent is hereby corrected as shown below:

On the Title Page

Page 4/Other Publications/Column 1/Sheridan: Error reads as "Odorous Exhause" and should read as "Odorous Exhaust"
Page 7/Other Publications/Column 1/Tolan: Error reads as ""logen's Demonstration" and should read as ""Logan's Demonstration"
Page 7/Other Publications/Column 2/Zhang: Error reads as ""Effect Effect" and should read as ""The Effect"
Page 7/Other Publications/Column 2/Kim: Error reads as "Biotechnolology" and should read as "Biotechnology"
Page 8/Other Publications/Column 2/Lewin: Error reads as ""Effect Effect" and should read as ""The Effect"

In the Specification

Column 2/Line 15-16: Error reads as "*Acidothermus cellullolyticum*," and should read as "*Acidothermus cellulolyticum*,"
Column 4/Line 52: Error reads as "Accelerase 1500" and should read as "Accellerase 1500"
Column 5/Line 9-10: Error reads as "Acellerase 1500" and should read as "Accellerase 1500"
Column 12/Line 28: Error reads as "at the these higher temperatures." and should read as "at these higher temperatures."
Column 30/Line 11: Error reads as "indicate that that ammonia" and should read as "indicate that ammonia"
Column 30/Line 25: Error reads as "Accelerase 1500" and should read as "Accellerase 1500"
Column 31/Table 5/Line 47: Error reads as "Acellerase 1500" and should read as "Accellerase 1500"
Column 31/Line 65: Error reads as "Acellerase 1500" and should read as "Accellerase 1500"

Signed and Sealed this
Eighth Day of August, 2017

Joseph Matal
*Performing the Functions and Duties of the
Under Secretary of Commerce for Intellectual Property and
Director of the United States Patent and Trademark Office*